United States Patent
Mansbach et al.

(10) Patent No.: US 11,427,623 B1
(45) Date of Patent: *Aug. 30, 2022

(54) METHODS OF TREATMENT USING MUTANT FGF-21 PEPTIDE CONJUGATES

(71) Applicant: 89bio Ltd., Herzliya (IL)

(72) Inventors: Hank Mansbach, Herzliya (IL); Chih-Ming Tseng, Herzliya (IL)

(73) Assignee: 89BIO LTD., Herzliya (IL)

( * ) Notice: Subject to any disclaimer, the term of this patent is extended or adjusted under 35 U.S.C. 154(b) by 91 days.

This patent is subject to a terminal disclaimer.

(21) Appl. No.: 16/885,353

(22) Filed: May 28, 2020

Related U.S. Application Data

(60) Provisional application No. 63/006,902, filed on Apr. 8, 2020, provisional application No. 62/853,645, filed on May 28, 2019.

(51) Int. Cl.
| | |
|---|---|
| *C07K 14/50* | (2006.01) |
| *A61K 38/18* | (2006.01) |
| *A61K 47/60* | (2017.01) |
| *A61K 9/00* | (2006.01) |
| *A61K 38/00* | (2006.01) |

(52) U.S. Cl.
CPC .......... *C07K 14/50* (2013.01); *A61K 38/1825* (2013.01); *A61K 47/60* (2017.08); *A61K 9/0019* (2013.01); *A61K 38/00* (2013.01)

(58) Field of Classification Search
CPC .................. A61K 38/1825; C07K 14/50
See application file for complete search history.

(56) References Cited

U.S. PATENT DOCUMENTS

| | | |
|---|---|---|
| 7,622,445 B2 | 11/2009 | Frye et al. |
| 8,034,770 B2 | 10/2011 | Belouski et al. |
| 9,187,532 B2 | 11/2015 | DeFrees |
| 9,200,049 B2 | 12/2015 | DeFrees |
| 9,631,004 B2 | 4/2017 | Morin et al. |
| 9,975,936 B2 | 5/2018 | Cujec et al. |
| 10,189,883 B2 | 1/2019 | Morin et al. |
| 10,407,479 B2 * | 9/2019 | Kopec ............... A61P 3/10 |
| 2004/0082038 A1 | 4/2004 | Lee et al. |
| 2007/0265200 A1 | 11/2007 | Glaesner et al. |
| 2007/0299007 A1 | 12/2007 | Frye et al. |
| 2008/0176790 A1 | 7/2008 | DeFrees |
| 2012/0172300 A1 | 7/2012 | DeFrees |
| 2018/0280474 A1 | 10/2018 | Xu et al. |
| 2019/0389921 A1 * | 12/2019 | Kopec ............... C07K 14/50 |
| 2021/0355183 A1 * | 11/2021 | Kopec ............... A61K 47/549 |

FOREIGN PATENT DOCUMENTS

| | | |
|---|---|---|
| CA | 2585758 A1 | 5/2006 |
| CN | 101516388 A | 8/2009 |
| CN | 103649127 A | 3/2014 |
| JP | 2008518601 A | 6/2008 |
| WO | 2008121563 A2 | 10/2008 |
| WO | 2010129600 A2 | 11/2010 |
| WO | 2016102562 A1 | 6/2016 |
| WO | 2019043457 A2 | 3/2019 |
| WO | WO-2019043457 A2 * | 3/2019 ............. A61K 47/60 |

OTHER PUBLICATIONS

Dozier et al., "Site-Specific PEGylation of Therapeutic Proteins," International Journal of Molecular Sciences, Oct. 28, 2015, vol. 16, No. 11, pp. 25831-25864.

Gimeno et al., "FGF21-based pharmacotherapy—potential utility for metabolic disorders," Trends in Endocrinology and Metabolism, Jun. 1, 2014, vol. 25, No. 6, pp. 303-311.

Meifei, Lu, "Site-directed chemical modification of FGF21 with polyethylene glycol and the function effect of PEGylated FGF21," Master Dissertation of Wenzhou Medical College.

Xu et al., "Polyethylene Glycol Modified FGF21 Engineered to Maximize Potency and Minimize Vacuole Formation," Bioconjugate Chemistry, Jun. 19, 2013, vol. 24, No. 6, pp. 915-925.

Sanyal, Arun et al., "Pegbelfermin (BMS-9860), a PEGylated Fibroblast growth factor 21 analogue, in patients with non-alcoholic steathohepatitis: a randomised, double-bline, placebo-controlled, phase 2a trial," www.thelancet.com; Dec. 13, 2018, pp. 1-13, http://dx.doi.org/10,1016/2014-6736(18)31785-9.

Charles, Edgar D., et al., "Pegbelfermin (BMS-986036), PEGylated FGF21, in Pateitns with Obesity and Type 2 Diabetes: Results from a Randomized Phase 2 Study," www.obesityjournal.org, Obesity, vol. 27, No. 11, Jan. 2019, pp. 41-19.

Molecular Cell Biology—NCBI Bookshelf, "Protein Glycosylation in the ER and Golgi Complex," https://www.ncbi.nlm.nih.gov/books/NBK21744[Apr. 18, 2019 4:38:49PM] (10 pages).

Camacho, Raul C., et al., "Pegylated Fgf21 rapidly normalizes insulin-stimulated glucose utilization in diet-induced insulin resistant mice," European Journal of Pharmacology 715 (2013) pp. 41-45.

(Continued)

*Primary Examiner* — Lianko G Garyu

(74) *Attorney, Agent, or Firm* — Greenberg Traurig, LLP

(57) ABSTRACT

Therapeutic regimens and uses of mutant Fibroblast Growth Factor-21 (FGF-21) peptide conjugates comprising a polyethylene glycol (PEG) moiety attached to a mutant FGF-21 peptide via a glycosyl moiety thereof in the treatment of nonalcoholic steatohepatitis are provided.

32 Claims, 37 Drawing Sheets
Specification includes a Sequence Listing.

(56) References Cited

OTHER PUBLICATIONS

Ye, Xianlong, et al., "Long-lasting hypaglycemic effect of modified FGF-21 analog with polyethylene glycol in type 1 diabetic mice and its systematic toxicity," European Journal of Pharmacology, 781 (2016) pp. 198-208.
Huang, Zhifeng et al., "A Better Anti-Diabetic Recombinant Human Fibroblast Growth Factor 21 (rhFGF21) Modified with Polyethylene Glycol," PLos ONE, Jun. 2011, vol. 1, issue 6, e20669, www.plosone.org, pp. 1-13.
Xu, Jing, et al., Polyethylene Glycol Modified FGF21 Engineered to Maximize Potency and Minimize Vecuole Formation, Bioconjugate Chemistry, American Chemical Society, pubs.acs.org/bc (Apr. 16, 2013), 11 pages.

* cited by examiner

FIG. 2

| Mean (SD) or % | Pooled BIO89-100 (n=43) | Placebo (n=15) |
|---|---|---|
| Age (years) | 39.3 (10.0) | 39.4 (9.3) |
| Male (%) | 86% | 87% |
| White (%) | 67% | 53% |
| Hispanic/Latino (%) | 44% | 40% |
| Weight (kg) | 79.9 (11.1) | 83.0 (14.9) |
| BMI (kg/m$^2$) | 26.5 (3.1) | 27.3 (3.0) |

FIG. 3

| Parameter Mean (SD) | Pooled BIO89-100 (n=43) | Placebo (n=15) |
|---|---|---|
| Triglycerides (mg/dL) | 92.1 (33.9) | 99.3 (42.0) |
| Total Cholesterol (mg/dL) | 182.2 (28.8) | 197.5 (31.8) |
| HDL (mg/dL) | 46.6 (9.2) | 50.8 (12.3) |
| LDL (mg/dL) | 122.2 (26.9) | 129.6 (26.6) |
| Glucose (mg/dL) | 87.8 (7.3) | 89.3 (6.1) |
| Insulin (uIU/mL) | 7.3 (3.1) | 7.3 (2.9) |
| ALT (U/L) | 21.0 (7.9) | 22.3 (5.7) |
| AST (U/L) | 20.3 (4.5) | 19.5 (4.0) |
| GGT (U/L) | 25.2 (10.7) | 25.4 (8.7) |

FIG. 4: Safety Summary: BIO89-100 Was Well-Tolerated

Treatment-Related TEAE Reported in ≥ 2 Subjects in Pooled BIO89-100 Treatment Group

| | Placebo | BIO89-100 | | | | | | Pooled BIO89-100 |
|---|---|---|---|---|---|---|---|---|
| ANY | 3 (20.0) | 0 | 0 | 1 (14.3) | 3 (50.0) | 6 (100) | 3 (50.0) | 13 (30.2) |
| Injection site induration | 1 (6.7) | 0 | 0 | 1 (14.3) | 0 | 5 (83.3) | 1 (16.7) | 7 (16.3) |
| Injection site erythema | 1 (6.7) | 0 | 0 | 0 | 0 | 3 (50.0) | 2 (33.3) | 5 (11.6) |
| Injection site pain | 0 | 0 | 0 | 0 | 0 | 2 (33.3) | 0 | 2 (4.7) |
| Headache | 1 (6.7) | 0 | 0 | 0 | 2 (33.3) | 0 | 0 | 2 (4.7) |

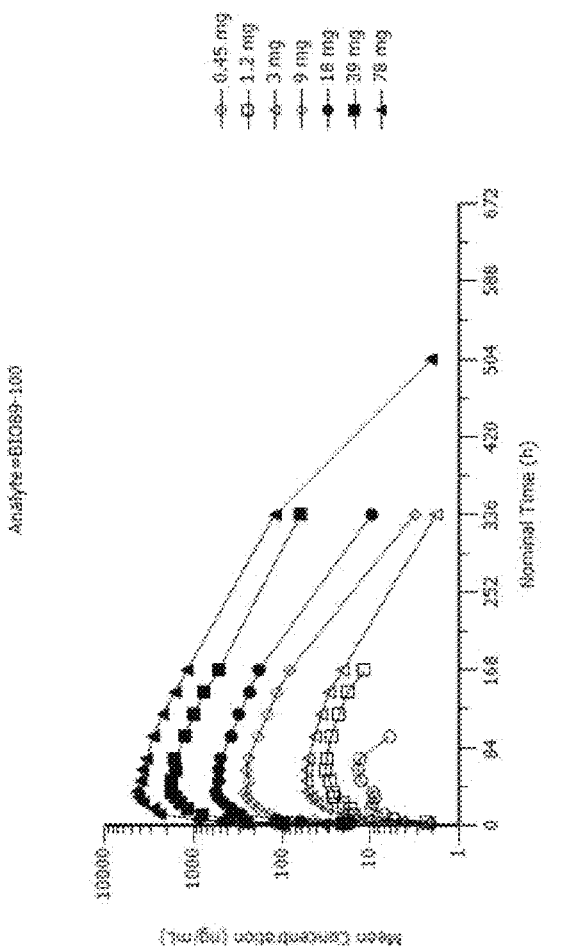

FIG. 11

| Parameter (mean) | 89bio Overall | BMS | | Akero |
|---|---|---|---|---|
| Study Population | Healthy Volunteers | Healthy obese | | Type 2 diabetics |
| Age (yr) | 39.3 | 40.4 | | 53.3 |
| Weight (kg) | 80.7 | 101.9 | | -- |
| BMI (kg/m$^2$) | 26.7 | 33.6 | | -- |
| Fasting glucose (mg/dL) | 88.2 | -- | | -- |
| ALT (U/L) | 21.3 | -- | | -- |
| Triglycerides (mg/dL) | 94.0 | -- | | -- |
| HgA1c (%) | -- | -- | | >6.5% |

BMS: Charles et al. AASLD 2016
Akero: AMG 876 20100015 Clinical Study Report Synopsis

FIG. 12

| | BIO89-100 Max % change (Day 8 or Day 15)* SAD Healthy Volunteer | | | | BMS# Day 14 % change MAD Healthy Obese | | Akcea^ % change SAD Type 2 diabetics |
|---|---|---|---|---|---|---|---|
| | 9.1 mg | 18.2 mg | 39 mg | 78 mg | 10 mg QD | 21 mg QW | 210 mg dose |
| TRIG | -33% | -41% | -45% | -51% | -35% | -25% | "up to -50%" |
| LDL | -23% | -21% | -37% | -25% | -25% | -20% | "up to -40%" |
| HDL | 16% | 21% | 36% | 34% | -8% | -9% | "up to 50%" |

Note: separate studies, not head-to-head comparison
* % change is calculated based on baseline mean and change from baseline mean; max % change is the max between D8 or D15
Charles et al. AASLD 2016; BMS data read from figure so not precise.
^ AMG 876 20100015 Clinical Study Report Synopsis; data stated as "compared to placebo"

FIG. 13

| | BIO89-100 | | | BMS | | Akero |
|---|---|---|---|---|---|---|
| | Max % change (Day 8 or Day 15)* SAD Healthy Volunteer | | | Day 14 % change MAD Healthy Obese | | % change SAD Type 2 diabetics |
| | 9.1 mg | 18.2 mg | 39 mg | 78 mg | 10 mg QD | 21 mg QW | |
| TRIG | -33% | -41% | -45% | -51% | -35% | -25% | "up to -50%" Day 11 at 70 mg |
| LDL | -23% | -21% | -37% | -25% | -25% | -20% | "up to -40%" at 210 mg |
| HDL | 16% | 21% | 36% | 34% | -8% | -9% | "up to 50%" Day 14 at 70 mg |

Note: separate studies, not head-to-head comparison
* % change is calculated based on baseline mean and change from baseline mean; max % change is the max between D8 or D15
& Charles et al. AASLD 2016; BMS data read from figure so not precise.
^ AMG 876 20100015 Clinical Study Report Synopsis; Akero S-1; data stated as "compared to placebo"

FIG. 14

| | BIOS-9100 | | | Madrigal | | Viking | | Intercept |
|---|---|---|---|---|---|---|---|---|
| | Max % chg (D8 or D15) SAD | | | % chg at D14 ** MAD | | % chg at D14 MAD | | % chg at W12 Phase 2 72W |
| | Healthy Volunteers | | | Healthy with LDL > 110 | | Healthy with ↑ cholesterol | | NASH patients |
| | 9.1 mg | 18.2 mg | 39 mg | 78 mg | 80mg | 100mg | 5mg | 10mg | 25mg |
| TRIG | -33% | -41% | -45% | -51% | -60% | -44% | -10% | -30% | -6% |
| LDL | -23% | -21% | -37% | -25% | -28% | -22% | -32% | -45% | 21% |
| HDL | 16% | 21% | 36% | 34% | no apparent change; data not presented | | "no meaningful trends" | | -9% |

Note: separate studies, not head-to-head comparison
* % change is calculated based on baseline mean and change from baseline mean; max % change is the max between D8 or D15
Taub et al; Atherosclerosis 2013; Madrigal corporate deck Sept 2017 & Lian et al; ACC 2016; read from figures
^FLINT study; Neuschwander-Tetri et al; Lancet 2015; read from figures   ** placebo subtracted

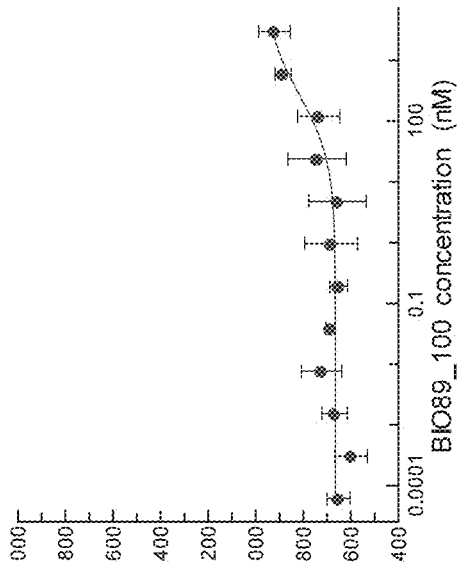
FIG. 16A
FIG. 16B
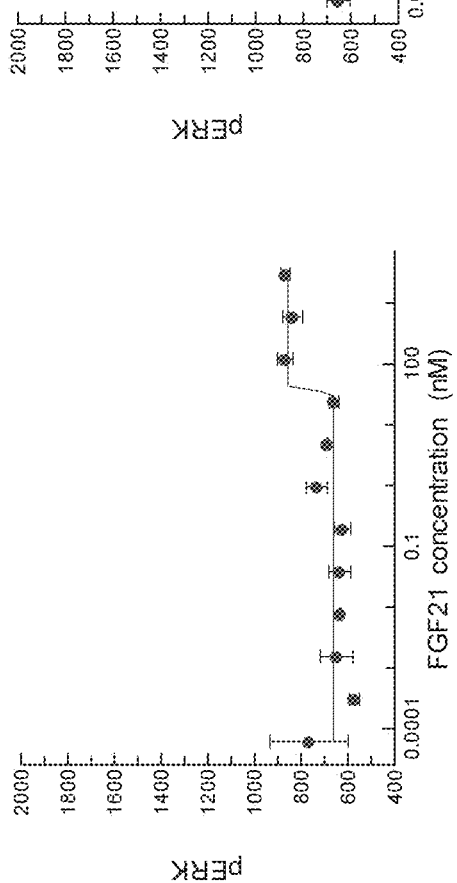
FIG. 16C
FIG. 16D

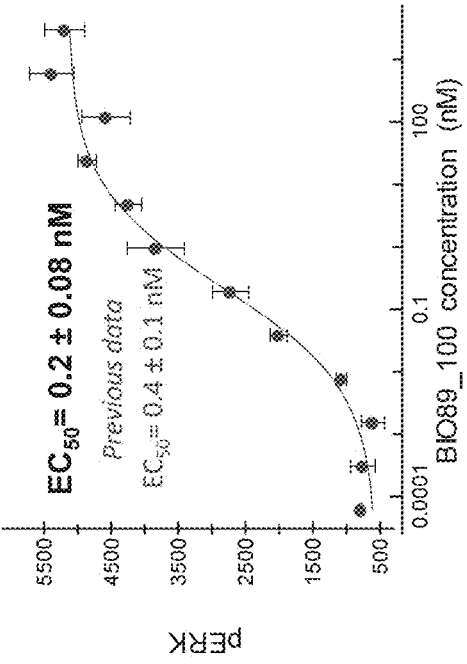
FIG. 17A
FIG. 17B
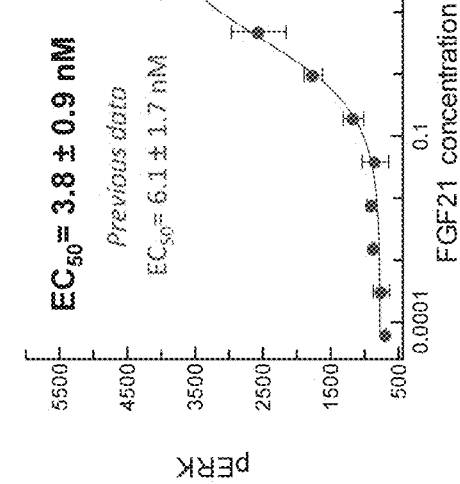
FIG. 17C
FIG. 17D

FIG. 19A
| FGF21 (nM) | pERK | | | |
|---|---|---|---|---|
| | Rep1 | Rep2 | Mean | StDev |
| 3000 | 2367 | 2358 | 2362.5 | 6.4 |
| 600 | 2317 | 2279 | 2298.0 | 26.9 |
| 120 | 2468 | 2294 | 2381.0 | 123.0 |
| 24 | 2268 | 2106 | 2187.0 | 114.6 |
| 4.8 | 1549 | 1678 | 1613.5 | 91.2 |
| 0.96 | 1558 | 1248 | 1403.0 | 219.2 |
| 0.192 | 997 | 1006 | 1001.5 | 6.4 |
| 0.0384 | 950 | 947 | 948.5 | 2.1 |
| 0.00768 | 831 | 803 | 817.0 | 19.8 |
| 0.00154 | 605 | 667 | 636.0 | 43.8 |
| 0.00031 | 768 | 668 | 718.0 | 70.7 |
| 0.00006 | 711 | 694 | 702.5 | 12.0 |
| vehicle | 658 | 701 | 679.5 | 30.4 |
FGF21
FIG. 19B
| BIO89-100 (nM) | pERK | | | |
|---|---|---|---|---|
| | Rep1 | Rep2 | Rep3 | Mean | StDev |
| 3000 | 2897 | 2678 | 2880 | 2818.3 | 121.3 |
| 600 | 2748 | 2779 | 2791 | 2772.7 | 22.2 |
| 120 | 2576 | 2874 | 2883 | 2777.7 | 174.7 |
| 24 | 2436 | 2247 | 2463 | 2382.0 | 117.7 |
| 4.8 | 1985 | 1859 | 1947 | 1930.3 | 64.6 |
| 0.96 | 1673 | 1772 | 1688 | 1711.0 | 53.4 |
| 0.192 | 1258 | 1168 | 1357 | 1261.0 | 94.5 |
| 0.0384 | 1011 | 997 | 857 | 955.0 | 85.2 |
| 0.00768 | 998 | 904 | 1113 | 1005.0 | 104.7 |
| 0.00154 | 701 | 803 | 736 | 746.7 | 51.8 |
| 0.00031 | 724 | 774 | 654 | 717.3 | 60.3 |
| 0.00006 | 687 | 753 | 802 | 747.3 | 57.7 |
| vehicle | 703 | 648 | 771 | 707.3 | 61.6 |
BIO89-100
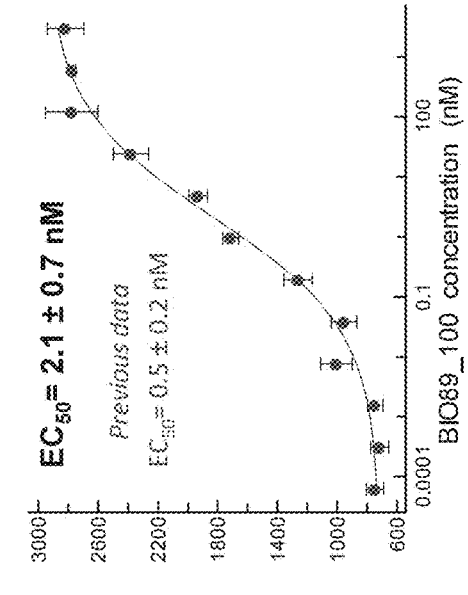
FIG. 19C
$EC_{50} = 2.2 \pm 0.8$ nM
Previous data
$EC_{50} = 1.2 \pm 0.2$ nM
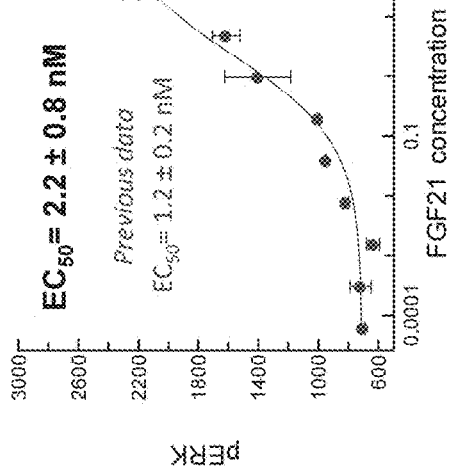
FIG. 19D
$EC_{50} = 2.1 \pm 0.7$ nM
Previous data
$EC_{50} = 0.5 \pm 0.2$ nM
In KLB-FGFR3 expressing cells BIO89-100 showed a comparable potency to FGF21

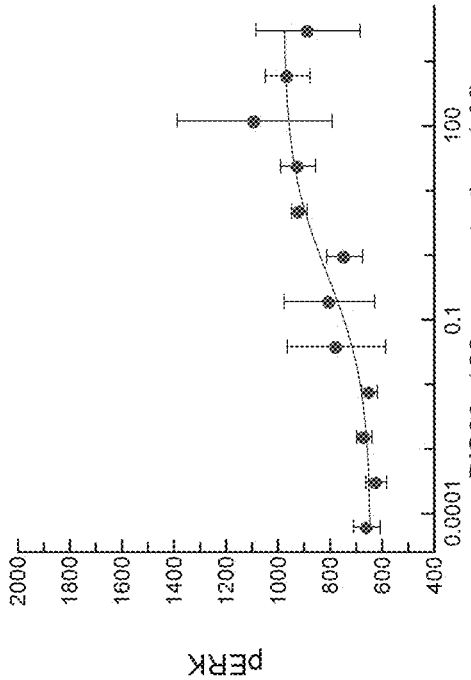
FIG. 20A
FIG. 20B
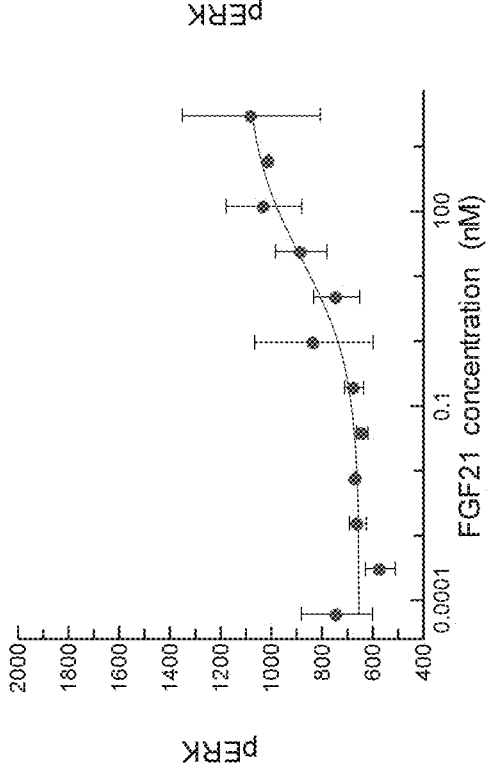
FIG. 20C
FIG. 20D

FIG. 21

| Cells | FGF21 | | BIO89_100 | |
|---|---|---|---|---|
| | EC$_{50}$ (nM) Mean ± StDev | Emax (pERK) Mean | EC$_{50}$ (nM) Mean ± StDev | Emax (pERK) Mean |
| KLB | nd | 726 | nd | 1089 |
| KLB/FGFR1 | 4,5 ± 1 | 4277 | 0,3 ± 0,07 | 4966 |
| KLB/FGFR2 | 4,5 ± 0,9 | 2058 | 1,1 ± 0,4 | 2471 |
| KLB/FGFR3 | 1,8 ± 0,3 | 2214 | 1,2 ± 0,4 | 2770 |
| KLB/FGFR4 | nd | 969 | nd | 995 | pERK Functional Assay in KLB/FGFR1 expressing cells-
FGF19
| FGF19 (nM) | pERK Rep1 | Rep2 | Rep3 | Mean | StDev |
|---|---|---|---|---|---|
| 3000 | 10034 | 10002 | 10831 | 10299.0 | 469.7 |
| 600 | 9884 | 10332 | 10147 | 10121.0 | 225.1 |
| 120 | 6541 | 9551 | 9531 | 8541.0 | 1732.0 |
| 24 | 6573 | 6431 | 6307 | 6437.0 | 133.1 |
| 4.8 | 3573 | 3415 | 3307 | 3431.7 | 133.8 |
| 0.96 | 1575 | 1554 | 1698 | 1609.3 | 77.6 |
| 0.192 | 1446 | 1498 | 1532 | 1492.0 | 43.3 |
| 0.0384 | 798 | 801 | 732 | 777.0 | 39.0 |
| 0.00768 | 549 | 667 | 598 | 604.7 | 59.1 |
| 0.00154 | 665 | 687 | 556 | 636.0 | 70.1 |
| 0.00031 | 637 | 746 | 539 | 640.7 | 103.5 |
| 0.00006 | 674 | 726 | 648 | 682.7 | 39.7 |
| vehicle | 632 | 661 | 588 | 627.0 | 36.8 |
FIG. 23A
FGF21
| FGF21 (nM) | pERK Rep1 | Rep2 | Rep3 | Mean | StDev |
|---|---|---|---|---|---|
| 3000 | 4223 | 4229 | 3994 | 4148.7 | 134.0 |
| 600 | 4286 | 3947 | 4166 | 4133.0 | 171.9 |
| 120 | 3844 | 3668 | 3948 | 3820.0 | 141.5 |
| 24 | 3317 | 3086 | 2997 | 3133.3 | 165.2 |
| 4.8 | 2501 | 2188 | 2384 | 2357.7 | 158.2 |
| 0.96 | 1555 | 1368 | 1429 | 1450.7 | 95.4 |
| 0.192 | 1338 | 1376 | 1509 | 1407.7 | 89.8 |
| 0.0384 | 760 | 658 | 501 | 639.7 | 130.5 |
| 0.00768 | 779 | 901 | 632 | 770.7 | 134.7 |
| 0.00154 | 602 | 548 | 632 | 594.0 | 42.6 |
| 0.00031 | 668 | 613 | 499 | 593.3 | 86.2 |
| 0.00006 | 426 | 638 | 754 | 606.0 | 166.3 |
| vehicle | 632 | 661 | 588 | 627.0 | 36.8 |
FIG. 23B
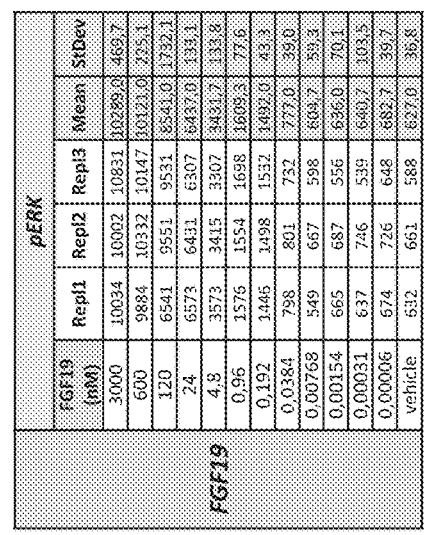
FIG. 23C
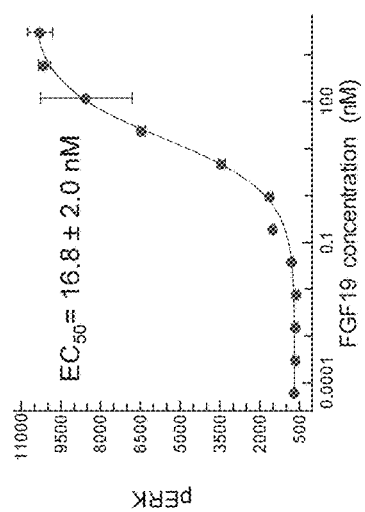
FIG. 23D
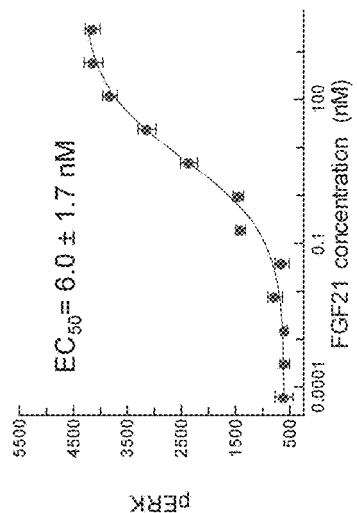
*Previous data on FGF21*
$EC_{50} = 4.2 \pm 2.0$ nM

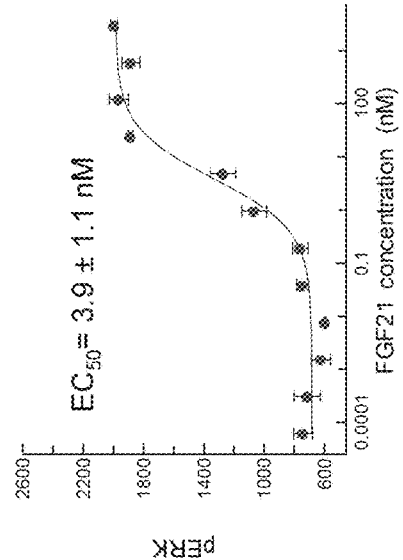
FIG. 24B
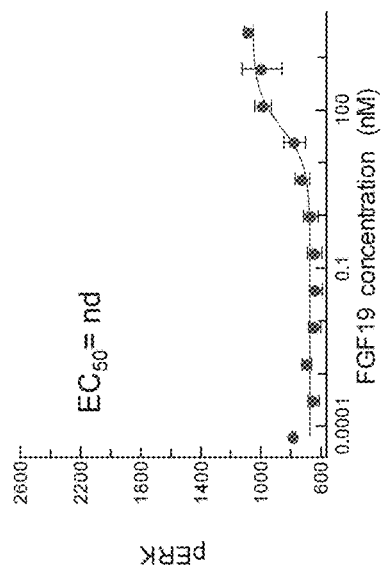
FIG. 24D
FIG. 24A
FIG. 24C

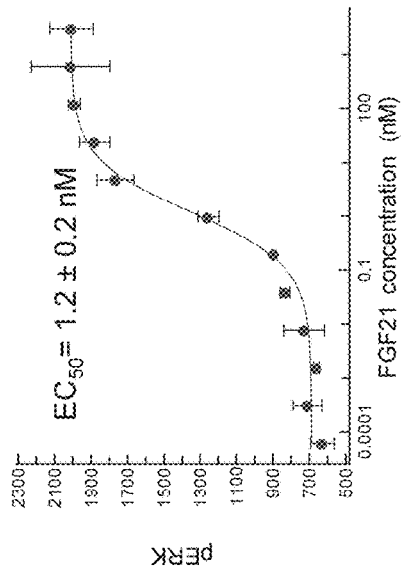
FIG. 25B
FIG. 25D
*Previous data on FGF21*
$EC_{50} = 2.4 \pm 0.6$ nM
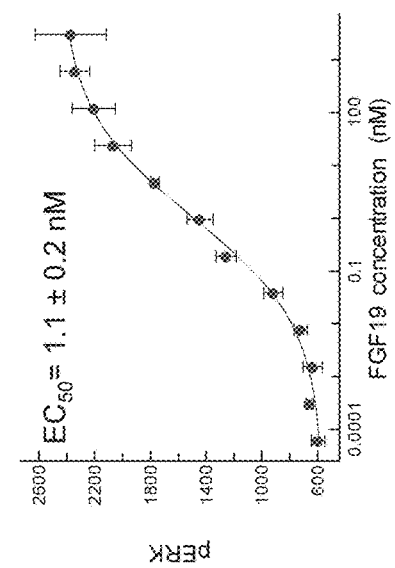
FIG. 25A
FIG. 25C

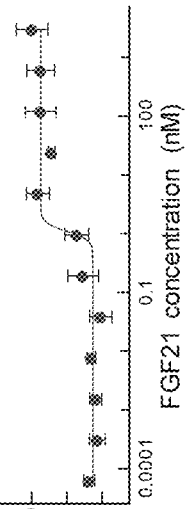
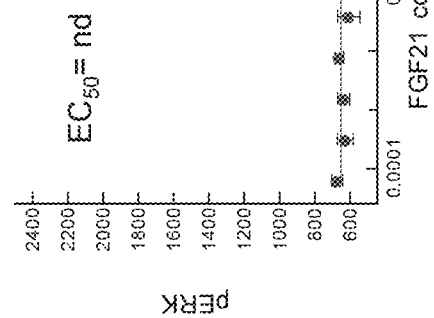
FIG. 26B
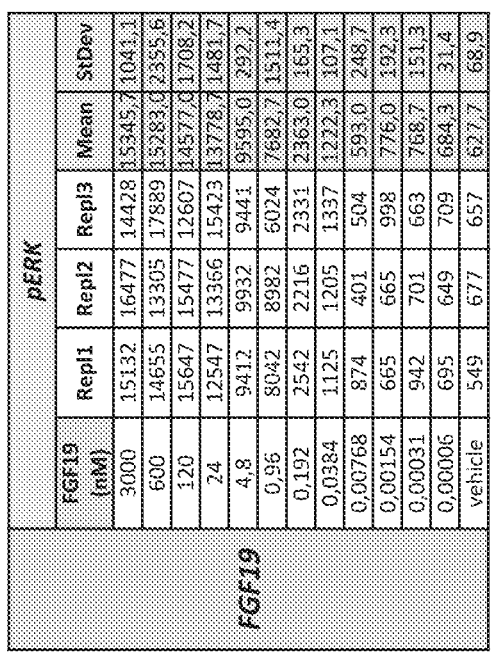
FIG. 26A
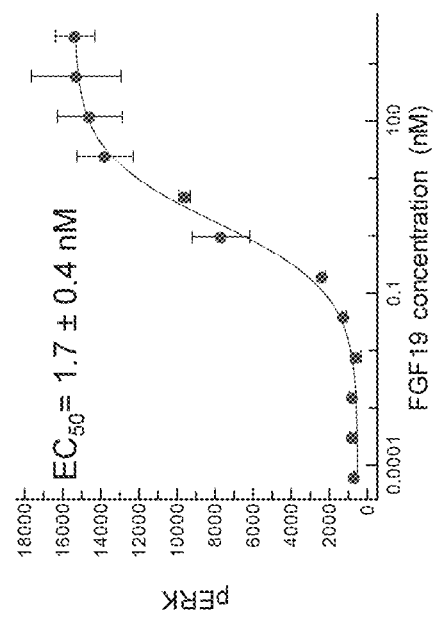
FIG. 26D
FIG. 26C

| EGF | EGF (nM) | pERK | | | | |
|---|---|---|---|---|---|---|
| | | Rep1 | Rep2 | Rep3 | Mean | StDev |
| | 3000 | 2230 | 2342 | 2300 | 2290.7 | 27.3 |
| | 600 | 2554 | 2065 | 2520 | 2379.7 | 233.0 |
| | 120 | 1861 | 1971 | 2433 | 2088.3 | 240.1 |
| | 24 | 1987 | 2013 | 1804 | 1934.7 | 105.6 |
| | 4.8 | 1360 | 1150 | 1254 | 1254.7 | 60.2 |
| | 0.96 | 1098 | 1080 | 1044 | 1074.0 | 19.3 |
| | 0.192 | 910 | 801 | 805 | 838.7 | 20.7 |
| | 0.0384 | 630 | 692 | 976 | 766.0 | 147.3 |
| | 0.00768 | 858 | 840 | 864 | 854.0 | 12.1 |
| | 0.001536 | 734 | 706 | 392 | 610.7 | 161.0 |
| | 0.0003072 | 766 | 850 | 808 | 808.0 | 24.2 |
| | 0.00006 | 570 | 858 | 578 | 668.7 | 142.9 |
| | vehicle | 816 | 588 | 688 | 697.3 | 60.6 |

| FGF21 | FGF21 (nM) | pERK | | | | |
|---|---|---|---|---|---|---|
| | | Rep1 | Rep2 | Rep3 | Mean | StDev |
| | 3000 | 3856 | 3412 | 4033 | 3767.0 | 311.6 |
| | 600 | 3624 | 4034 | 4974 | 4210.7 | 499.6 |
| | 120 | 4892 | 4060 | 3702 | 4218.0 | 264.4 |
| | 24 | 2812 | 3234 | 3690 | 3245.3 | 260.1 |
| | 4.8 | 2454 | 2176 | 2226 | 2285.3 | 54.7 |
| | 0.96 | 1630 | 1566 | 1370 | 1522.0 | 102.8 |
| | 0.192 | 1590 | 1708 | 1172 | 1490.0 | 269.6 |
| | 0.0384 | 560 | 468 | 614 | 547.3 | 73.1 |
| | 0.00768 | 706 | 672 | 516 | 631.3 | 80.9 |
| | 0.001536 | 604 | 600 | 590 | 598.0 | 5.3 |
| | 0.0003072 | 722 | 588 | 622 | 644.0 | 28.2 |
| | 0.00006 | 494 | 390 | 664 | 516.0 | 137.1 |
| | vehicle | 614 | 846 | 836 | 765.3 | 44.0 |

| FGF23 | FGF23 (nM) | pERK | | | |
|---|---|---|---|---|---|
| | | Rep1 | Rep2 | Mean | StDev |
| | 3000 | 1331 | 655 | 993.0 | 239.0 |
| | 600 | 1266 | 1222 | 1244.0 | 15.6 |
| | 120 | 1370 | 1120 | 1245.0 | 83.4 |
| | 24 | 896 | 818 | 857.0 | 27.6 |
| | 4.8 | 1082 | 1078 | 1080.0 | 1.4 |
| | 0.96 | 1098 | 1074 | 1086.0 | 8.5 |
| | 0.192 | 942 | 1123 | 1032.5 | 64.0 |
| | 0.0384 | 864 | 896 | 880.0 | 11.3 |
| | 0.00768 | 742 | 950 | 846.0 | 73.5 |
| | 0.001536 | 670 | 642 | 656.0 | 9.9 |
| | 0.0003072 | 846 | 654 | 750.0 | 67.9 |
| | 0.00006 | 632 | 948 | 790.0 | 111.7 |
| | vehicle | 620 | 888 | 754.0 | 94.8 |

$EC_{50} = 8.9 \pm 2.8$ nM $EC_{50} = 4.2 \pm 2.0$ nM $EC_{50}$ nd

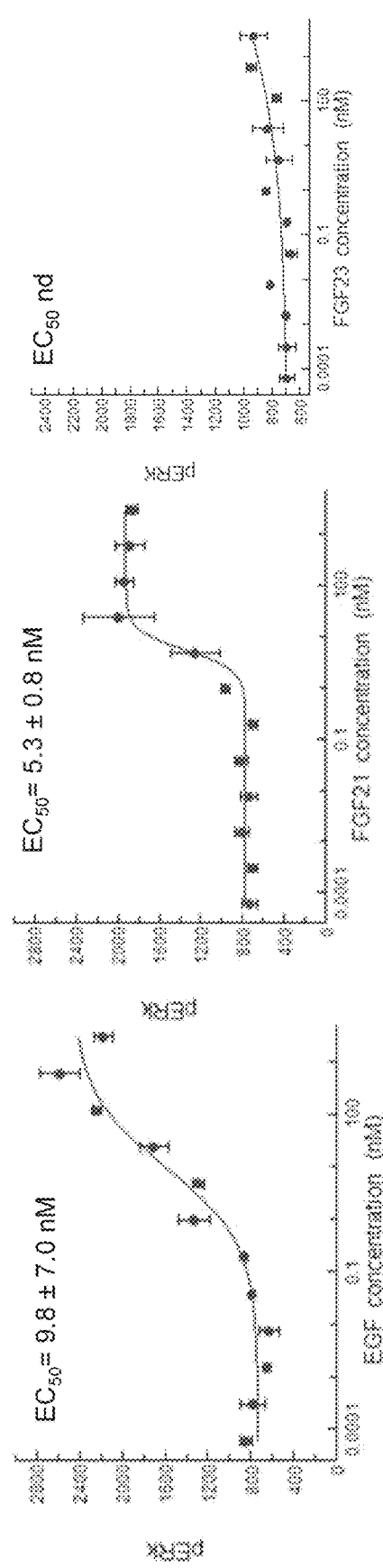
FIG. 29A | FIG. 29B | FIG. 29C
FIG. 29D | FIG. 29E | FIG. 29F

| EGF (nM) | Repl1 | Repl2 | Repl3 | Mean | StDev |
|---|---|---|---|---|---|
| 3000 | 2231 | 2099 | 2322 | 2217.3 | 111.6 |
| 600 | 2011 | 2183 | 2210 | 2134.7 | 38.2 |
| 120 | 2550 | 2435 | 2591 | 2525.3 | 78.3 |
| 24 | 1811 | 1788 | 1891 | 1830.0 | 51.8 |
| 4.8 | 1432 | 1401 | 1392 | 1408.3 | 8.2 |
| 0.96 | 1109 | 1022 | 1022 | 1051.0 | 16.7 |
| 0.192 | 861 | 1012 | 804 | 892.3 | 104.4 |
| 0.0384 | 701 | 990 | 783 | 824.7 | 109.5 |
| 0.00768 | 771 | 671 | 772 | 738.0 | 51.4 |
| 0.001536 | 563 | 810 | 671 | 681.3 | 77.4 |
| 0.0003072 | 801 | 735 | 677 | 737.7 | 34.3 |
| 0.00006 | 694 | 621 | 551 | 622.0 | 40.7 |
| vehicle | 667 | 788 | 580 | 678.3 | 104.1 |
FIG. 30A
| FGF21 (nM) | Repl1 | Repl2 | Repl3 | Mean | StDev |
|---|---|---|---|---|---|
| 3000 | 1838 | 2521 | 2088 | 2149.0 | 234.4 |
| 600 | 2281 | 2133 | 2219 | 2211.0 | 47.5 |
| 120 | 2311 | 2012 | 2192 | 2171.7 | 98.6 |
| 24 | 2109 | 2067 | 1921 | 2032.3 | 76.3 |
| 4.8 | 1677 | 1886 | 1621 | 1728.0 | 133.3 |
| 0.96 | 1191 | 1033 | 1088 | 1104.0 | 37.2 |
| 0.192 | 920 | 901 | 1161 | 994.0 | 131.7 |
| 0.0384 | 810 | 811 | 991 | 870.7 | 91.7 |
| 0.00768 | 689 | 701 | 718 | 702.7 | 9.4 |
| 0.001536 | 656 | 691 | 661 | 672.7 | 15.1 |
| 0.0003072 | 781 | 711 | 504 | 665.3 | 108.8 |
| 0.00006 | 788 | 842 | 801 | 810.3 | 21.5 |
| vehicle | 667 | 788 | 580 | 678.3 | 104.1 |
FIG. 30B
| FGF23 (nM) | Repl1 | Repl2 | Mean | StDev |
|---|---|---|---|---|
| 3000 | 1066 | 788 | 927.0 | 98.3 |
| 600 | 899 | 991 | 945.0 | 32.5 |
| 120 | 719 | 810 | 764.5 | 32.2 |
| 24 | 981 | 677 | 829.0 | 107.5 |
| 4.8 | 877 | 620 | 748.5 | 90.9 |
| 0.96 | 801 | 881 | 841.0 | 28.3 |
| 0.192 | 671 | 705 | 688.0 | 12.0 |
| 0.0384 | 609 | 712 | 660.5 | 36.4 |
| 0.00768 | 817 | 800 | 808.5 | 6.0 |
| 0.001536 | 721 | 671 | 696.0 | 17.7 |
| 0.0003072 | 781 | 604 | 692.5 | 62.6 |
| 0.00006 | 622 | 763 | 692.5 | 49.9 |
| vehicle | 667 | 788 | 727.5 | 42.8 |
FIG. 30C
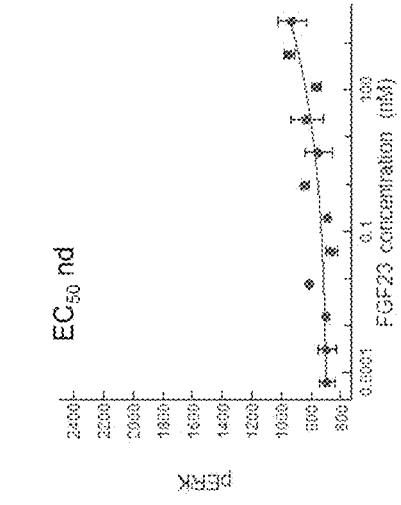
FIG. 30D
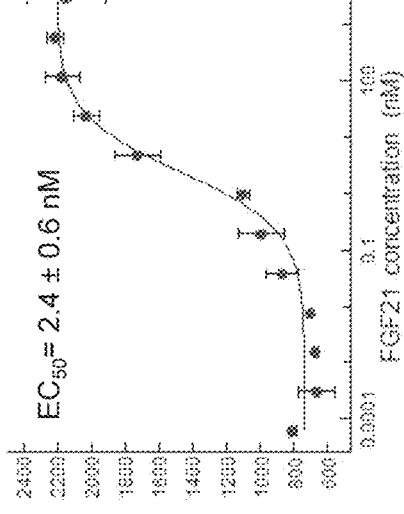
FIG. 30E
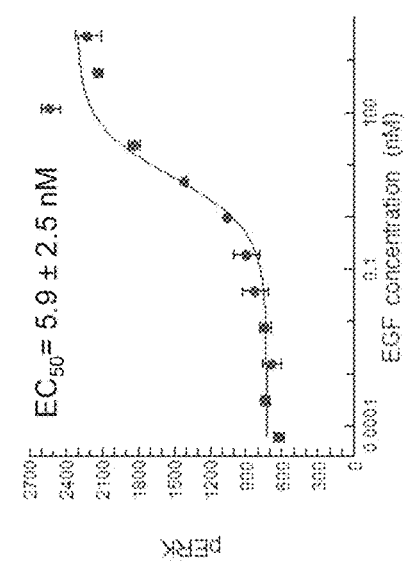
FIG. 30F

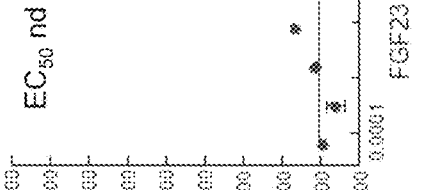
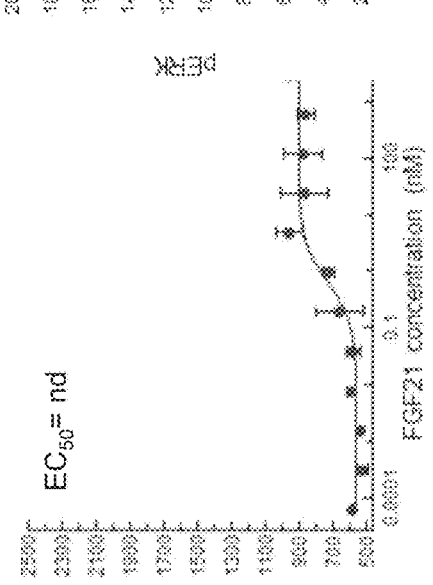
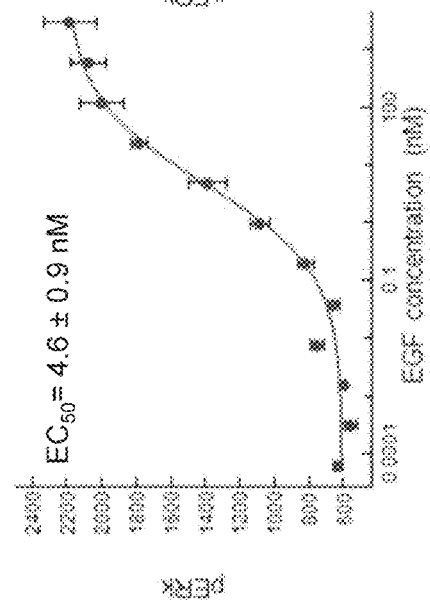
FIG. 31A  FIG. 31B  FIG. 31C
FIG. 31D  FIG. 31E  FIG. 31F

*Low $E_{max}$ less than 2-fold of basal level

| Receptor | FGF21 | | EGF | |
| --- | --- | --- | --- | --- |
| | $EC_{50}$ (nM) Mean ± sd | Emax (pERK) | EC50 (nM) | Emax (pERK) |
| KLB | nd | *602.1 | 8.8 | 1331 |
| FGFR1 | 4.2 ± 2.0 | 4192 | 8.9 | 2364 |
| FGFR2 | 5.3 ± 0.8 | 1923 | 9.8 | 2461 |
| FGFR3 | 2.4 ± 0.6 | 2203 | 5.9 | 2307 |
| FGFR4 | nd | *901 | 4.6 | 2198 |

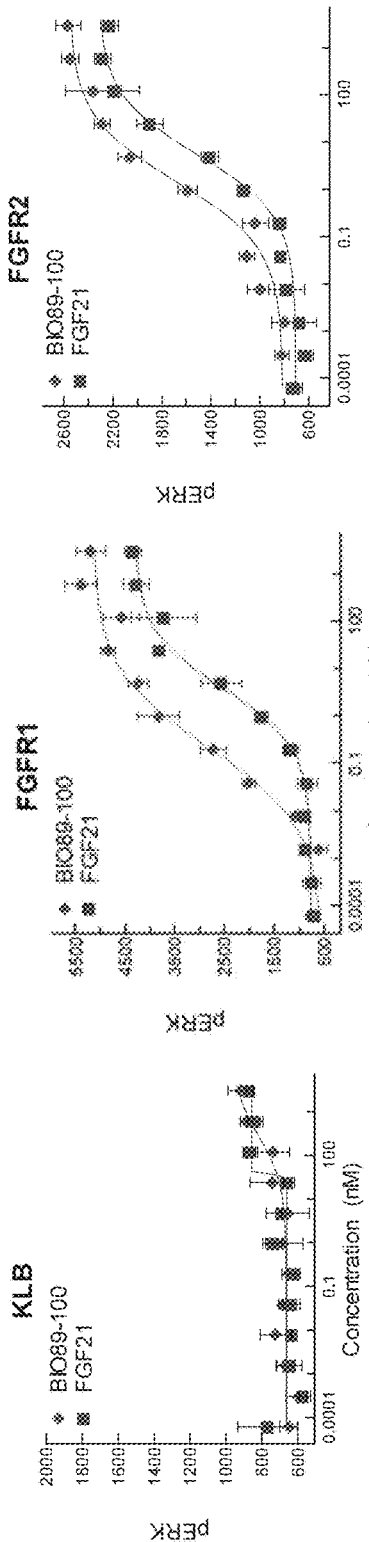
FIG. 33A
FIG. 33B
FIG. 33C
FIG. 33D
FIG. 33E
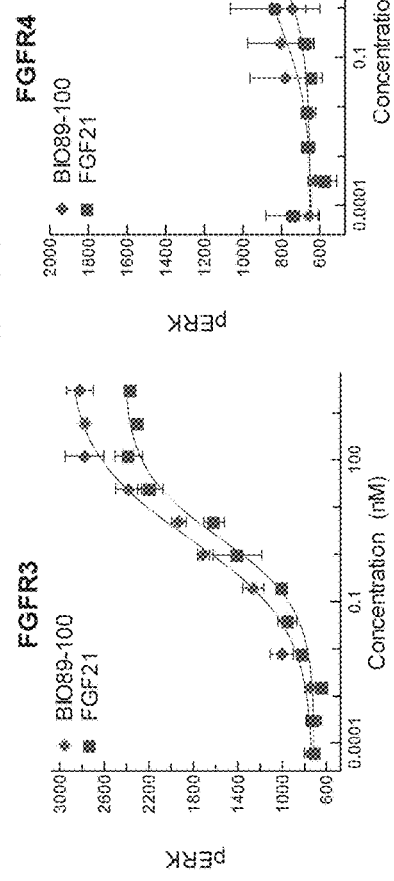
| Receptor | FGF21 | | BIO89-100 | |
|---|---|---|---|---|
| | EC$_{50}$ (nM) Mean ± StDev | Emax (pERK) | EC$_{50}$ (nM) Mean ± StDev | Emax (pERK) |
| KLB | nd | 857 | nd | 968 |
| FGFR1 | 3.8 ± 0.9 | 4313 | 0.2 ± 0.1 | 5145 |
| FGFR2 | 5.5 ± 1.8 | 2316 | 1.5 ± 0.5 | 2553 |
| FGFR3 | 2.2 ± 0.8 | 2426 | 2.1 ± 0.7 | 2942 |
| FGFR4 | nd | 1106 | nd | 980 |
FIG. 33F

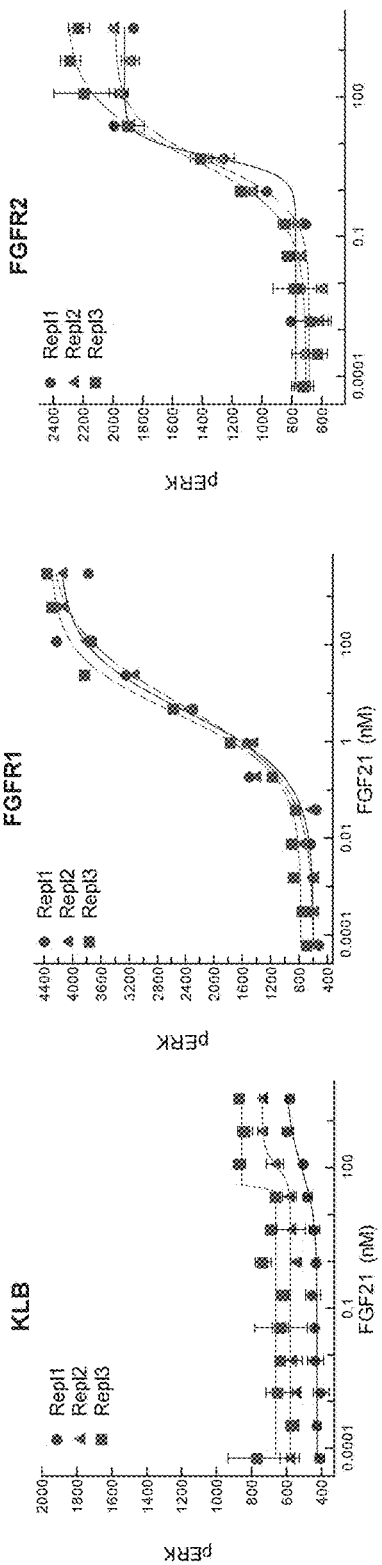
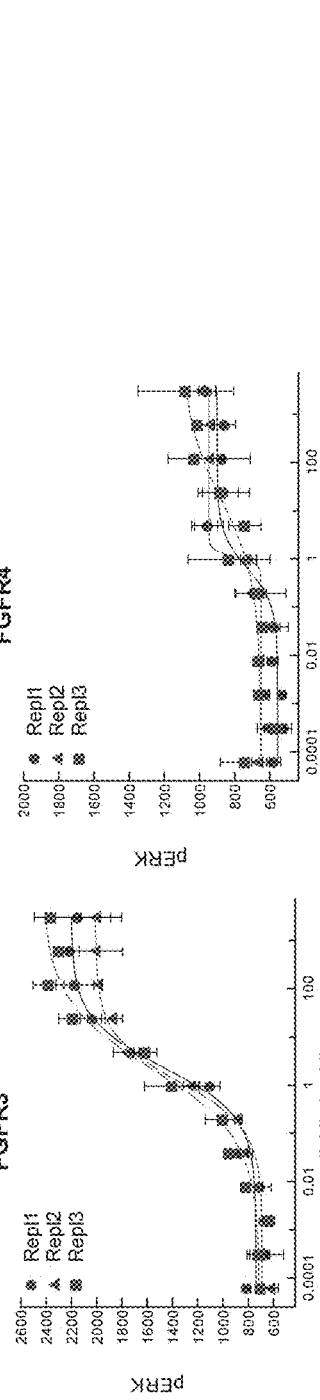
FIG. 34A  FIG. 34B  FIG. 34C  FIG. 34D  FIG. 34E
| Receptor | FGF21 (Exp1) | | FGF21 (Exp2) | | FGF21 (Exp3) | |
|---|---|---|---|---|---|---|
| | EC$_{50}$ (nM) Mean ± StDev | Emax (pERK) | EC$_{50}$ (nM) Mean ± StDev | Emax (pERK) | EC$_{50}$ (nM) Mean ± StDev | Emax (pERK) |
| KLB | nd | 602 | nd | 737 | nd | 857 |
| FGFR1 | 4.2 ± 1.9 | 4192 | 6.0 ± 1.7 | 4355 | 3.8 ± 0.9 | 4313 |
| FGFR2 | 5.3 ± 0.8 | 1923 | 3.9 ± 1.1 | 1987 | 5.5 ± 1.8 | 2316 |
| FGFR3 | 2.3 ± 0.6 | 2203 | 1.2 ± 0.2 | 2010 | 2.2 ± 0.8 | 2426 |
| FGFR4 | 0.6 ± 0.3 | 901 | nd | 948 | nd | 1106 |
FIG. 34F

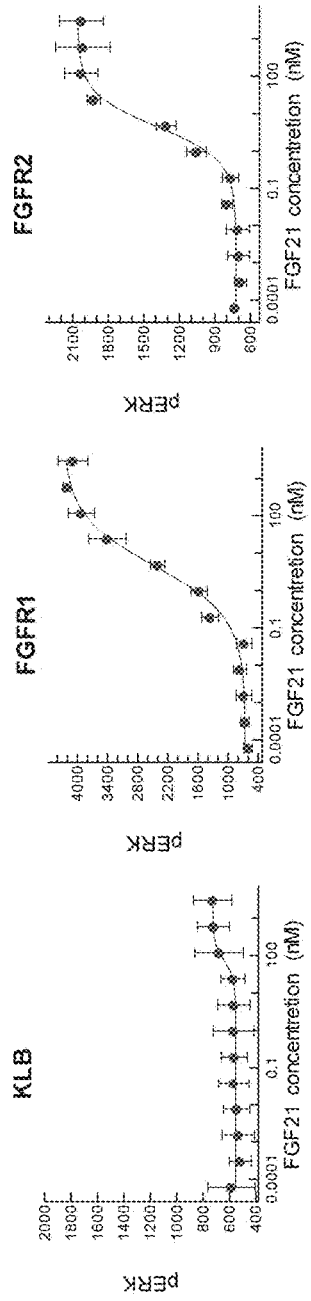
FIG. 35A
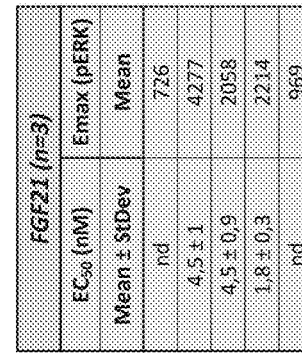
FIG. 35G
FIG. 35B
FIG. 35C
FIG. 35D
FIG. 35E
FIG. 35F

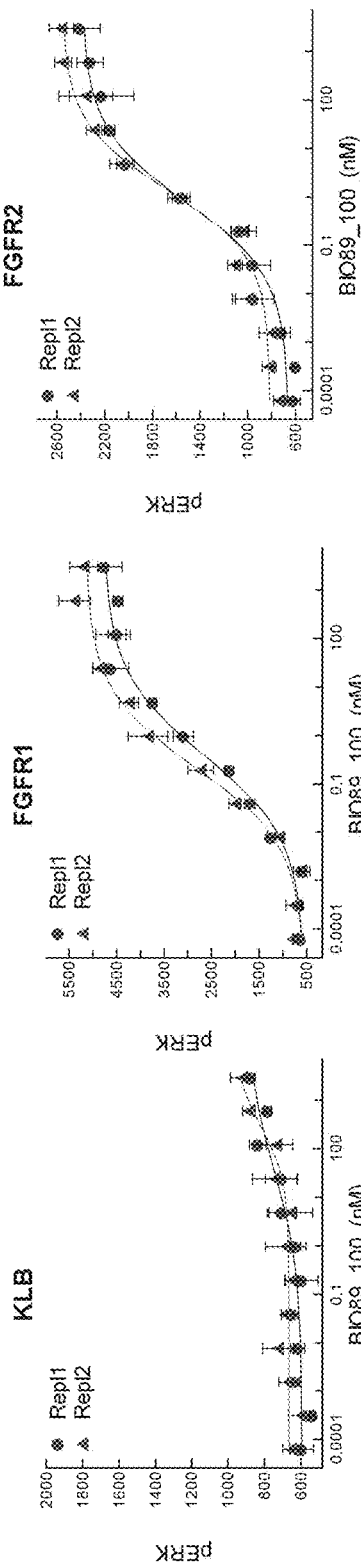
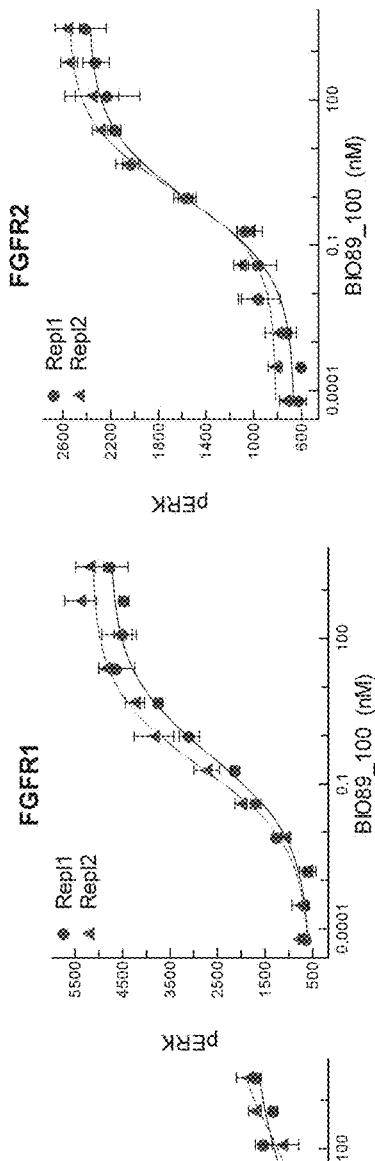
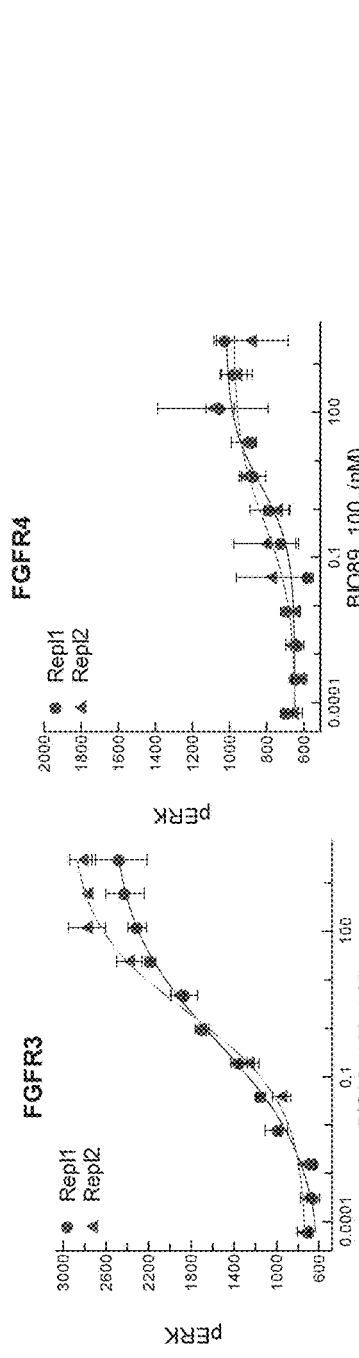
FIG. 36A  FIG. 36B  FIG. 36C  FIG. 36D  FIG. 36E
| Receptor | BIO89_100 (Exp1) | | BIO89_100 (Exp2) | |
|---|---|---|---|---|
| | EC$_{50}$ (nM) Mean ± StDev | Emax (pERK) | EC$_{50}$ (nM) Mean ± StDev | Emax (pERK) |
| KLB | nd | 899 | nd | 968 |
| FGFR1 | 0.4 ± 0.1 | 4765 | 0.2 ± 0.1 | 5145 |
| FGFR2 | 0.8 ± 0.3 | 2386 | 1.5 ± 0.5 | 2553 |
| FGFR3 | 0.5 ± 0.2 | 2569 | 2.1 ± 0.7 | 2942 |
| FGFR4 | nd | 1020 | nd | 980 |
FIG. 36F

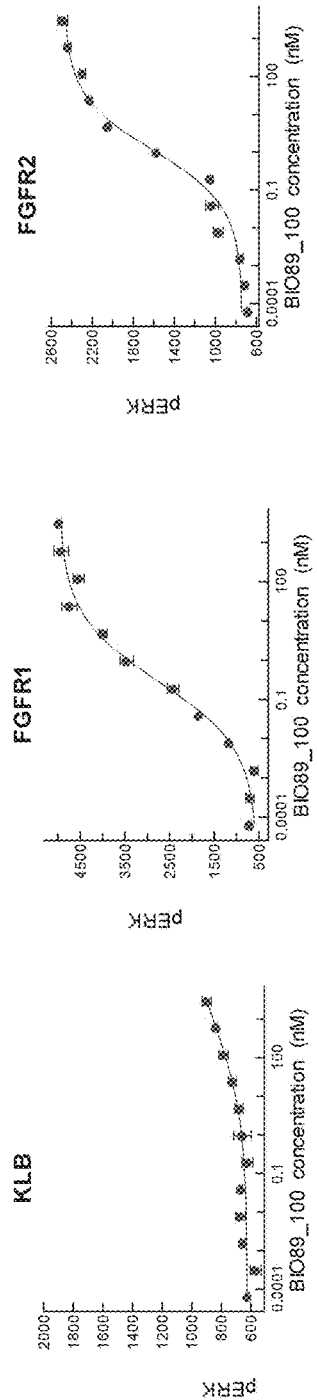
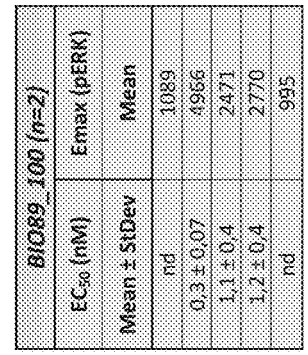
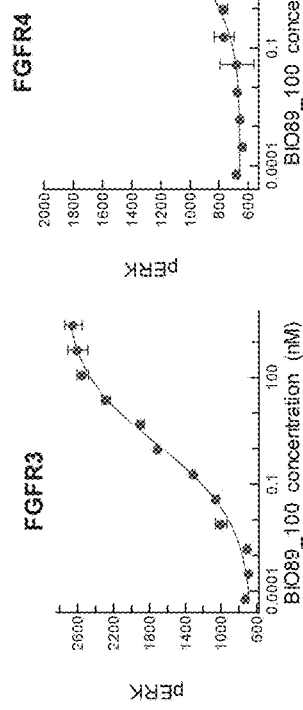

SEQUENCE LISTING

```
<160> NUMBER OF SEQ ID NOS: 28

<210> SEQ ID NO 1
<211> LENGTH: 182
<212> TYPE: PRT
<213> ORGANISM: Homo sapiens

<400> SEQUENCE: 1

Met His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95
```

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
            115                 120                 125

Pro Ala Pro Arg Gly Pro Ala Arg Phe Leu Pro Leu Pro Gly Leu Pro
            130                 135                 140

Pro Ala Leu Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
            180

<210> SEQ ID NO 2
<211> LENGTH: 182
<212> TYPE: PRT
<213> ORGANISM: Artificial
<220> FEATURE:
<223> OTHER INFORMATION: mutant

<400> SEQUENCE: 2

Met His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
            35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
            115                 120                 125

Pro Ala Pro Arg Gly Pro Ala Arg Phe Leu Pro Leu Pro Gly Leu Pro
            130                 135                 140

Pro Ala Leu Pro Glu Pro Pro Gly Ile Leu Ala Pro Gln Pro Pro Asp
145                 150                 155                 160

Val Gly Ser Ser Asp Pro Leu Ser Met Val Gly Pro Thr Gln Gly Ala
                165                 170                 175

Ser Pro Ser Tyr Ala Ser
            180

<210> SEQ ID NO 3
<211> LENGTH: 182
<212> TYPE: PRT
<213> ORGANISM: Artificial
<220> FEATURE:
<223> OTHER INFORMATION: mutant

<400> SEQUENCE: 3

Met His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
             35                  40                  45

Ser Pro Glu Ser Leu Leu Gln Leu Lys Ala Leu Lys Pro Gly Val Ile
 50                  55                  60

Gln Ile Leu Gly Val Lys Thr Ser Arg Phe Leu Cys Gln Arg Pro Asp
 65                  70                  75                  80

Gly Ala Leu Tyr Gly Ser Leu His Phe Asp Pro Glu Ala Cys Ser Phe
                 85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
            115                 120                 125

Pro Ala Pro Arg Gly Pro Ala Arg Phe Leu Pro Leu Pro Gly Leu Pro
130                 135                 140

Pro Ala Leu Pro Glu Pro Pro Gly Ile Leu Ala Pro Gln Pro Pro Asp
145                 150                 155                 160

Val Gly Ser Ser Asp Pro Leu Ser Met Val Gly Pro Thr Gln Gly Ala
                165                 170                 175

Met Pro Ser Tyr Ala Ser
            180

<210> SEQ ID NO 4
<211> LENGTH: 182
<212> TYPE: PRT
<213> ORGANISM: Artificial
<220> FEATURE:
<223> OTHER INFORMATION: mutant

<400> SEQUENCE: 4

Met His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
             35                  40                  45

Ser Pro Glu Ser Leu Leu Gln Leu Lys Ala Leu Lys Pro Gly Val Ile
 50                  55                  60

Gln Ile Leu Gly Val Lys Thr Ser Arg Phe Leu Cys Gln Arg Pro Asp
 65                  70                  75                  80

Gly Ala Leu Tyr Gly Ser Leu His Phe Asp Pro Glu Ala Cys Ser Phe
                 85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
            115                 120                 125

Pro Ala Pro Arg Gly Pro Ala Arg Phe Leu Pro Leu Pro Gly Leu Pro
130                 135                 140

Pro Ala Leu Pro Glu Pro Pro Gly Ile Leu Ala Pro Thr Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
            180

```
<210> SEQ ID NO 5
<211> LENGTH: 182
<212> TYPE: PRT
<213> ORGANISM: Artificial
<220> FEATURE:
<223> OTHER INFORMATION: mutant

<400> SEQUENCE: 5

Met His Pro Ile Pro Thr Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
        115                 120                 125

Pro Ala Pro Arg Gly Pro Ala Arg Phe Leu Pro Leu Pro Gly Leu Pro
    130                 135                 140

Pro Ala Leu Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
            180

<210> SEQ ID NO 6
<211> LENGTH: 182
<212> TYPE: PRT
<213> ORGANISM: Artificial
<220> FEATURE:
<223> OTHER INFORMATION: mutant

<400> SEQUENCE: 6

Met His Pro Thr Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110
```

-continued

```
His Gly Leu Pro Leu His Leu Pro Gly Asn Lys Ser Pro His Arg Asp
        115                 120                 125

Pro Ala Pro Arg Gly Pro Ala Arg Phe Leu Pro Leu Pro Gly Leu Pro
    130                 135                 140

Pro Ala Leu Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
        180

<210> SEQ ID NO 7
<211> LENGTH: 182
<212> TYPE: PRT
<213> ORGANISM: Artificial
<220> FEATURE:
<223> OTHER INFORMATION: mutant

<400> SEQUENCE: 7

Met His Pro Ile Pro Asp Ser Ser Pro Thr Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
        115                 120                 125

Pro Ala Pro Arg Gly Pro Ala Arg Phe Leu Pro Leu Pro Gly Leu Pro
    130                 135                 140

Pro Ala Leu Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
        180

<210> SEQ ID NO 8
<211> LENGTH: 182
<212> TYPE: PRT
<213> ORGANISM: Artificial
<220> FEATURE:
<223> OTHER INFORMATION: mutant

<400> SEQUENCE: 8

Met His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30
```

```
His Leu Glu Ile Arg Glu Asp Gly Thr Val Gly Gly Ala Ala Asp Gln
            35                  40                  45

Ser Pro Thr Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
                100                 105                 110

His Gly Leu Pro Leu His Leu Pro Gly Asn Lys Ser Pro His Arg Asp
            115                 120                 125

Pro Ala Pro Arg Gly Pro Ala Arg Phe Leu Pro Leu Pro Gly Leu Pro
        130                 135                 140

Pro Ala Leu Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
            180

<210> SEQ ID NO 9
<211> LENGTH: 182
<212> TYPE: PRT
<213> ORGANISM: Artificial
<220> FEATURE:
<223> OTHER INFORMATION: mutant

<400> SEQUENCE: 9

Met His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
                20                  25                  30

His Leu Glu Ile Arg Glu Asp Gly Thr Val Gly Gly Ala Ala Asp Gln
            35                  40                  45

Ser Pro Glu Ser Leu Leu Gln Leu Lys Ala Leu Lys Pro Thr Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
                100                 105                 110

His Gly Leu Pro Leu His Leu Pro Gly Asn Lys Ser Pro His Arg Asp
            115                 120                 125

Pro Ala Pro Arg Gly Pro Ala Arg Phe Leu Pro Leu Pro Gly Leu Pro
        130                 135                 140

Pro Ala Leu Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
            180
```

<210> SEQ ID NO 10
<211> LENGTH: 182
<212> TYPE: PRT
<213> ORGANISM: Artificial
<220> FEATURE:
<223> OTHER INFORMATION: mutant

<400> SEQUENCE: 10

```
Met His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Thr
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
        115                 120                 125

Pro Ala Pro Arg Gly Pro Ala Arg Phe Leu Pro Leu Pro Gly Leu Pro
    130                 135                 140

Pro Ala Leu Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
            180
```

<210> SEQ ID NO 11
<211> LENGTH: 182
<212> TYPE: PRT
<213> ORGANISM: Artificial
<220> FEATURE:
<223> OTHER INFORMATION: mutant

<400> SEQUENCE: 11

```
Met His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Thr Ala Cys Ser Phe
                85                  90                  95

Arg Glu Leu Leu Leu Glu Asp Gly Tyr Asn Val Tyr Gln Ser Glu Ala
            100                 105                 110
```

```
His Gly Leu Pro Leu His Leu Pro Gly Asn Lys Ser Pro His Arg Asp
        115                 120                 125

Pro Ala Pro Arg Gly Pro Ala Arg Phe Leu Pro Leu Pro Gly Leu Pro
        130                 135                 140

Pro Ala Leu Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
        180

<210> SEQ ID NO 12
<211> LENGTH: 182
<212> TYPE: PRT
<213> ORGANISM: Artificial
<220> FEATURE:
<223> OTHER INFORMATION: mutant

<400> SEQUENCE: 12

Met His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
                20                  25                  30

His Leu Glu Ile Arg Glu Asp Gly Thr Val Gly Gly Ala Ala Asp Gln
            35                  40                  45

Ser Pro Glu Ser Leu Leu Gln Leu Lys Ala Leu Lys Pro Gly Val Ile
        50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Thr His Leu Pro Gly Asn Lys Ser Pro His Arg Asp
        115                 120                 125

Pro Ala Pro Arg Gly Pro Ala Arg Phe Leu Pro Leu Pro Gly Leu Pro
        130                 135                 140

Pro Ala Leu Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
        180

<210> SEQ ID NO 13
<211> LENGTH: 182
<212> TYPE: PRT
<213> ORGANISM: Artificial
<220> FEATURE:
<223> OTHER INFORMATION: mutant

<400> SEQUENCE: 13

Met His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
                20                  25                  30
```

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
 50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
                100                 105                 110

His Gly Leu Pro Leu His Leu Pro Thr Asn Lys Ser Pro His Arg Asp
                115                 120                 125

Pro Ala Pro Arg Gly Pro Ala Arg Phe Leu Pro Leu Pro Gly Leu Pro
130                 135                 140

Pro Ala Leu Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
                180

<210> SEQ ID NO 14
<211> LENGTH: 182
<212> TYPE: PRT
<213> ORGANISM: Artificial
<220> FEATURE:
<223> OTHER INFORMATION: mutant

<400> SEQUENCE: 14

Met His Pro Ile Pro Asp Ser Ser Pro Leu Leu Gln Phe Gly Gly Gln
1                5                  10                  15

Val Arg Gln Arg Tyr Leu Tyr Thr Asp Asp Ala Gln Gln Thr Glu Ala
                20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
 50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
                100                 105                 110

His Gly Leu Pro Leu His Leu Pro Gly Asn Lys Ser Pro Thr Arg Asp
                115                 120                 125

Pro Ala Pro Arg Gly Pro Ala Arg Phe Leu Pro Leu Pro Gly Leu Pro
130                 135                 140

Pro Ala Leu Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
                180

<210> SEQ ID NO 15

```
<211> LENGTH: 182
<212> TYPE: PRT
<213> ORGANISM: Artificial
<220> FEATURE:
<223> OTHER INFORMATION: mutant

<400> SEQUENCE: 15

Met His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
        115                 120                 125

Pro Thr Pro Arg Gly Pro Ala Arg Phe Leu Pro Leu Pro Gly Leu Pro
    130                 135                 140

Pro Ala Leu Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
            180

<210> SEQ ID NO 16
<211> LENGTH: 182
<212> TYPE: PRT
<213> ORGANISM: Artificial
<220> FEATURE:
<223> OTHER INFORMATION: mutant

<400> SEQUENCE: 16

Met His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
        115                 120                 125
```

```
Pro Ala Pro Thr Gly Pro Ala Arg Phe Leu Pro Leu Pro Gly Leu Pro
        130                 135                 140

Pro Ala Leu Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
            180

<210> SEQ ID NO 17
<211> LENGTH: 182
<212> TYPE: PRT
<213> ORGANISM: Artificial
<220> FEATURE:
<223> OTHER INFORMATION: mutant

<400> SEQUENCE: 17

Met His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
        115                 120                 125

Pro Ala Pro Arg Gly Pro Thr Arg Phe Leu Pro Leu Pro Gly Leu Pro
    130                 135                 140

Pro Ala Leu Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
            180

<210> SEQ ID NO 18
<211> LENGTH: 182
<212> TYPE: PRT
<213> ORGANISM: Artificial
<220> FEATURE:
<223> OTHER INFORMATION: mutant

<400> SEQUENCE: 18

Met His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45
```

```
Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
 65                  70                  75                  80

Gly Ala Leu Tyr Gly Ser Leu His Phe Asp Pro Glu Ala Cys Ser Phe
                 85                  90                  95

Arg Glu Leu Leu Leu Glu Asp Gly Tyr Asn Val Tyr Gln Ser Glu Ala
                100                 105                 110

His Gly Leu Pro Leu His Leu Pro Gly Asn Lys Ser Pro His Arg Asp
            115                 120                 125

Pro Ala Pro Arg Gly Pro Ala Arg Phe Leu Pro Thr Pro Gly Leu Pro
        130                 135                 140

Pro Ala Leu Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
            180

<210> SEQ ID NO 19
<211> LENGTH: 182
<212> TYPE: PRT
<213> ORGANISM: Artificial
<220> FEATURE:
<223> OTHER INFORMATION: mutant

<400> SEQUENCE: 19

Met His Pro Ile Pro Asp Ser Ser Pro Leu Leu Gln Phe Gly Gly Gln
 1               5                  10                  15

Val Arg Gln Arg Tyr Leu Tyr Thr Asp Asp Ala Gln Gln Thr Glu Ala
                20                  25                  30

His Leu Glu Ile Arg Glu Asp Gly Thr Val Gly Gly Ala Ala Asp Gln
            35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
 65                  70                  75                  80

Gly Ala Leu Tyr Gly Ser Leu His Phe Asp Pro Glu Ala Cys Ser Phe
                 85                  90                  95

Arg Glu Leu Leu Leu Glu Asp Gly Tyr Asn Val Tyr Gln Ser Glu Ala
                100                 105                 110

His Gly Leu Pro Leu His Leu Pro Gly Asn Lys Ser Pro His Arg Asp
            115                 120                 125

Pro Ala Pro Arg Gly Pro Ala Arg Phe Leu Pro Leu Pro Thr Leu Pro
        130                 135                 140

Pro Ala Leu Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
            180

<210> SEQ ID NO 20
<211> LENGTH: 183
<212> TYPE: PRT
<213> ORGANISM: Artificial
```

<220> FEATURE:
<223> OTHER INFORMATION: mutant

<400> SEQUENCE: 20

```
Met His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
        115                 120                 125

Pro Ala Pro Arg Gly Pro Ala Arg Phe Leu Pro Leu Pro Gly Leu Pro
    130                 135                 140

Thr Pro Ala Leu Pro Glu Pro Gly Ile Leu Ala Pro Gln Pro Pro
145                 150                 155                 160

Asp Val Gly Ser Ser Asp Pro Leu Ser Met Val Gly Pro Ser Gln Gly
                165                 170                 175

Arg Ser Pro Ser Tyr Ala Ser
            180
```

<210> SEQ ID NO 21
<211> LENGTH: 182
<212> TYPE: PRT
<213> ORGANISM: Artificial
<220> FEATURE:
<223> OTHER INFORMATION: mutant

<400> SEQUENCE: 21

```
Met His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
        115                 120                 125

Pro Ala Pro Arg Gly Pro Ala Arg Phe Leu Pro Leu Pro Gly Leu Pro
    130                 135                 140
```

```
Pro Thr Leu Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
            180

<210> SEQ ID NO 22
<211> LENGTH: 182
<212> TYPE: PRT
<213> ORGANISM: Artificial
<220> FEATURE:
<223> OTHER INFORMATION: mutant

<400> SEQUENCE: 22

Met His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
                20                  25                  30

His Leu Glu Ile Arg Glu Asp Gly Thr Val Gly Gly Ala Ala Asp Gln
            35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
        115                 120                 125

Pro Ala Pro Arg Gly Pro Ala Arg Phe Leu Pro Leu Pro Gly Leu Pro
130                 135                 140

Pro Ala Leu Pro Thr Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
            180

<210> SEQ ID NO 23
<211> LENGTH: 183
<212> TYPE: PRT
<213> ORGANISM: Artificial
<220> FEATURE:
<223> OTHER INFORMATION: mutant

<400> SEQUENCE: 23

Met His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
                20                  25                  30

His Leu Glu Ile Arg Glu Asp Gly Thr Val Gly Gly Ala Ala Asp Gln
            35                  40                  45

Ser Pro Glu Ser Leu Leu Gln Leu Lys Ala Leu Lys Pro Gly Val Ile
    50                  55                  60
```

```
Gln Ile Leu Gly Val Lys Thr Ser Arg Phe Leu Cys Gln Arg Pro Asp
 65                  70                  75                  80

Gly Ala Leu Tyr Gly Ser Leu His Phe Asp Pro Glu Ala Cys Ser Phe
                 85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
            115                 120                 125

Pro Ala Pro Arg Gly Pro Ala Arg Phe Leu Pro Leu Pro Gly Leu Pro
        130                 135                 140

Pro Ala Leu Pro Glu Pro Thr Pro Gly Ile Leu Ala Pro Gln Pro Pro
145                 150                 155                 160

Asp Val Gly Ser Ser Asp Pro Leu Ser Met Val Gly Pro Ser Gln Gly
                165                 170                 175

Arg Ser Pro Ser Tyr Ala Ser
            180

<210> SEQ ID NO 24
<211> LENGTH: 182
<212> TYPE: PRT
<213> ORGANISM: Artificial
<220> FEATURE:
<223> OTHER INFORMATION: mutant

<400> SEQUENCE: 24

Met His Pro Ile Pro Asp Ser Ser Pro Leu Leu Gln Phe Gly Gly Gln
  1               5                  10                  15

Val Arg Gln Arg Tyr Leu Tyr Thr Asp Asp Ala Gln Gln Thr Glu Ala
                 20                  25                  30

His Leu Glu Ile Arg Glu Asp Gly Thr Val Gly Gly Ala Ala Asp Gln
             35                  40                  45

Ser Pro Glu Ser Leu Leu Gln Leu Lys Ala Leu Lys Pro Gly Val Ile
 50                  55                  60

Gln Ile Leu Gly Val Lys Thr Ser Arg Phe Leu Cys Gln Arg Pro Asp
 65                  70                  75                  80

Gly Ala Leu Tyr Gly Ser Leu His Phe Asp Pro Glu Ala Cys Ser Phe
                 85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
            115                 120                 125

Pro Ala Pro Arg Gly Pro Ala Arg Phe Leu Pro Leu Pro Gly Leu Pro
        130                 135                 140

Pro Ala Leu Pro Glu Pro Pro Thr Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser
            180
```

<210> SEQ ID NO 25
<211> LENGTH: 183
<212> TYPE: PRT
<213> ORGANISM: Artificial
<220> FEATURE:
<223> OTHER INFORMATION: mutant

<400> SEQUENCE: 25

```
Met His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
        115                 120                 125

Pro Ala Pro Arg Gly Pro Ala Arg Phe Leu Pro Leu Pro Gly Leu Pro
    130                 135                 140

Pro Ala Leu Pro Glu Pro Pro Gly Ile Leu Ala Pro Gln Pro Thr Pro
145                 150                 155                 160

Asp Val Gly Ser Ser Asp Pro Leu Ser Met Val Gly Pro Ser Gln Gly
                165                 170                 175

Arg Ser Pro Ser Tyr Ala Ser
            180
```

<210> SEQ ID NO 26
<211> LENGTH: 182
<212> TYPE: PRT
<213> ORGANISM: Artificial
<220> FEATURE:
<223> OTHER INFORMATION: mutant

<400> SEQUENCE: 26

```
Met His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110
```

```
His Gly Leu Pro Leu His Leu Pro Gly Asn Lys Ser Pro His Arg Asp
        115                 120                 125

Pro Ala Pro Arg Gly Pro Ala Arg Phe Leu Pro Leu Pro Gly Leu Pro
    130                 135                 140

Pro Ala Leu Pro Glu Pro Pro Gly Ile Leu Ala Pro Gln Pro Pro Thr
145                 150                 155                 160

Val Gly Ser Ser Asp Pro Leu Ser Met Val Gly Pro Ser Gln Gly Arg
                165                 170                 175

Ser Pro Ser Tyr Ala Ser
            180

<210> SEQ ID NO 27
<211> LENGTH: 182
<212> TYPE: PRT
<213> ORGANISM: Artificial
<220> FEATURE:
<223> OTHER INFORMATION: mutant

<400> SEQUENCE: 27

Met His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
                20                  25                  30

His Leu Glu Ile Arg Glu Asp Gly Thr Val Gly Gly Ala Ala Asp Gln
            35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
                100                 105                 110

His Gly Leu Pro Leu His Leu Pro Gly Asn Lys Ser Pro His Arg Asp
        115                 120                 125

Pro Ala Pro Arg Gly Pro Ala Arg Phe Leu Pro Leu Pro Gly Leu Pro
    130                 135                 140

Pro Ala Leu Pro Glu Pro Pro Gly Ile Leu Ala Pro Gln Pro Pro Asp
145                 150                 155                 160

Val Gly Ser Ser Asp Pro Thr Ser Met Val Gly Pro Ser Gln Gly Arg
                165                 170                 175

Ser Pro Ser Tyr Ala Ser
            180

<210> SEQ ID NO 28
<211> LENGTH: 182
<212> TYPE: PRT
<213> ORGANISM: Artificial
<220> FEATURE:
<223> OTHER INFORMATION: mutant

<400> SEQUENCE: 28

Met His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
                20                  25                  30
```

```
His Leu Glu Ile Arg Glu Asp Gly Thr Val Gly Gly Ala Ala Asp Gln
    35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
            115                 120                 125

Pro Ala Pro Arg Gly Pro Ala Arg Phe Leu Pro Leu Pro Gly Leu Pro
    130                 135                 140

Pro Ala Leu Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Thr Tyr Ala Ser
                180
```

METHODS OF TREATMENT USING MUTANT FGF-21 PEPTIDE CONJUGATES

RELATED APPLICATIONS

This application claims the benefit of and priority to U.S. provisional Application Ser. No. 62/853,645, filed May 28, 2019, and U.S. provisional Application Ser. No. 63/006,902, filed Apr. 8, 2020, the entire disclosure of each of which is incorporated herein by reference in their entireties.

SEQUENCE LISTING

The instant application contains a Sequence Listing which has been submitted electronically in ASCII format and is hereby incorporated in reference in its entirety. Said ASCII copy, created on May 19, 2020 is named 180234-010802US_ST25.txt and is 46,336 bytes in size.

FIELD OF THE INVENTION

Therapeutic regimens and uses of mutant Fibroblast Growth Factor-21 (FGF-21) peptide conjugates comprising a polyethylene glycol (PEG) moiety attached to a mutant FGF-21 peptide via a glycosyl moiety thereof are provided.

BACKGROUND OF THE INVENTION

FGF-21 is an endocrine hormone that is naturally found as a monomeric non-glycosylated protein. Together with FGF-19 and FGF-23, FGF-21 belongs to the endocrine-acting sub-family while the remaining of the 18 mammalian FGF ligands are grouped into five paracrine-acting sub-families.

SUMMARY OF THE INVENTION

In some embodiments, provided herein are methods of treating nonalcoholic steatohepatitis (NASH) in a subject in need thereof, comprising administering once a week to the subject in need thereof a pharmaceutical composition comprising from about 3 mg to about 27 mg of a mutant Fibroblast Growth Factor-21 (FGF-21) peptide conjugate and a pharmaceutically acceptable carrier, wherein the pharmaceutical composition is administered once a week, wherein the mutant FGF-21 peptide conjugate comprises i) a mutant FGF-21 peptide comprising the amino acid sequence of SEQ ID NO: 2, ii) a glycosyl moiety, and iii) a 20 kDa polyethylene glycol (PEG), wherein the mutant FGF-21 peptide is attached to the glycosyl moiety by a covalent bond between a threonine at amino acid position 173 of SEQ ID NO: 2 and a first site of the glycosyl moiety and wherein the glycosyl moiety is attached to the 20 kDa PEG by a covalent bond between a second site of the glycosyl moiety and the 20 kDa PEG, wherein administration of the pharmaceutical composition results in at least one of: a reduction of the liver size as assessed by Magnetic resonance imaging—Proton density fat fraction, a reduction of the levels of one or more biomarkers comprising Pro-C3, alanine transaminase (ALT), Enhanced LiverFibrosis (ELF) panel, Adiponectin, CK-18, inflammation marker high-sensitivity C-reactive protein (hs-CRP), Hemoglobin A1c (HbA1c), and Triglycerides, and an increase of the levels of HDL-c.

In some embodiments, provided herein are methods of treating nonalcoholic steatohepatitis (NASH) in a subject in need thereof, comprising: administering once every two weeks to the subject in need thereof a pharmaceutical composition comprising from about 18 mg to about 36 mg of a mutant Fibroblast Growth Factor-21 (FGF-21) peptide conjugate and a pharmaceutically acceptable carrier, wherein the pharmaceutical composition is administered once a week, wherein the mutant FGF-21 peptide conjugate comprises i) a mutant FGF-21 peptide comprising the amino acid sequence of SEQ ID NO: 2, ii) a glycosyl moiety, and iii) a 20 kDa polyethylene glycol (PEG), wherein the mutant FGF-21 peptide is attached to the glycosyl moiety by a covalent bond between a threonine at amino acid position 173 of SEQ ID NO: 2 and a first site of the glycosyl moiety and wherein the glycosyl moiety is attached to the 20 kDa PEG by a covalent bond between a second site of the glycosyl moiety and the 20 kDa PEG, wherein administration of the pharmaceutical composition results in at least one of: a reduction of the liver size as assessed by Magnetic resonance imaging—Proton density fat fraction, a reduction of the levels of one or more biomarkers comprising Pro-C3, alanine transaminase (ALT), Enhanced LiverFibrosis (ELF) panel, Adiponectin, CK-18, inflammation marker high-sensitivity C-reactive protein (hs-CRP), Hemoglobin A1c (HbA1c), Triglycerides, LDL-c, and an increase of the levels of HDL-c.

In some embodiments, the subject is a human subject.

In some embodiments, the pharmaceutical composition is administered sub-subcutaneously.

In some embodiments, the glycosyl moiety comprises at least one of an N-acetylgalactosamine (GalNAc) residue, a galactose (Gal) residue, a sialic acid (Sia) residue, a 5-amine analogue of a Sia residue, a mannose (Man) residue, mannosamine, a glucose (Glc) residue, an N-acetylglucosamine (GlcNAc) residue, a fucose residue, a xylose residue, or a combination thereof. In some embodiments, the glycosyl moiety comprises at least one of an N-acetylgalactosamine (GalNAc) residue, a galactose (Gal) residue, a sialic acid (Sia), or a combination thereof. In some embodiments, the at least one Sia residue is a nine-carbon carboxylated sugar. In some embodiments, the at least one Sia residue is N-acetyl-neuraminic acid (2-keto-5-acetamido-3,5-dideoxy-D-glycero-D-galactononulopyranos-1-onic acid (Neu5Ac), N-glycolylneuraminic acid (Neu5Gc), 2-keto-3-deoxy-nonulosonic acid (KDN), or a 9-substituted sialic acid. In some embodiments, the 9-substituted sialic acid is 9-O-lactyl-Neu5Ac, 9-O-acetyl-Neu5Ac, 9-deoxy-9-fluoro-Neu5Ac, or 9-azido-9-deoxy-Neu5Ac. In some embodiments, the glycosyl moiety comprises the structure -GalNAc-Sia-. In some embodiments, the 20 kDa PEG moiety is attached to the glycosyl moiety by a covalent bond to a linker, wherein the linker comprises at least one amino acid residue. In some embodiments, the at least one amino acid residue is a glycine (Gly). In some embodiments, the mutant FGF-21 comprises the structure -GalNAc-Sia-Gly-PEG (20 kDa).

In some embodiments, the mutant FGF-21 comprises the structure:

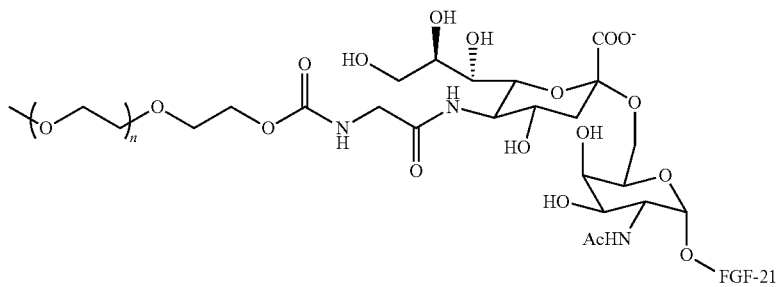

wherein n is an integer selected from 450 to 460.

In some embodiments, the 20 kDa PEG is a linear or branched PEG. In some embodiments, the 20 kDa PEG is a 20 kDa methoxy-PEG.

In some embodiments, the mutant FGF-21 displays an equal or higher potency than wild type FGF-21 when tested in vitro in KLB-FGFR1, KLB-FGFR2 and KLB-FGFR3 expressing cells.

In some embodiments, mutant Fibroblast Growth Factor-21 (FGF-21) peptide conjugates comprising a mutant FGF-21 peptide are described comprising at least one threonine residue adjacent to at least one proline (P) residue on the C-terminal side of the at least one proline residue, thereby forming at least one O-linked glycosylation site which does not exist in the corresponding native FGF-21, wherein the corresponding native FGF-21 has an amino acid sequence that is at least 95% identical to SEQ ID NO: 1, and a 20 kDa polyethylene glycol (PEG), wherein the 20 kDa PEG is covalently attached to the mutant FGF-21 peptide at the at least one threonine residue via a glycosyl moiety.

In some embodiments, compositions comprising mutant Fibroblast Growth Factor-21 (FGF-21) peptide conjugates, methods for producing the mutant FGF-21 peptide conjugate and uses thereof in the treatment of at least one of diabetes and related diseases, particularly diabetes type 2, non-alcoholic steatohepatitis (NASH), nonalcoholic fatty liver disease (NAFLD), or metabolic syndrome are provided. In some embodiments, the diabetes type 2, NAFLD, NASH, or metabolic syndrome are treated in a human subject. In some embodiments, provided is a method for treating diabetes and related diseases in a subject in need of such treatment, particularly diabetes type 2, non-alcoholic NASH and/or metabolic syndrome, and more particularly diabetes type 2, NAFLD, NASH, and/or metabolic syndrome in a human subject.

In some embodiments, encompassed herein is the mutant FGF-21 peptide conjugate for use in treating diabetes type 2, NAFLD, NASH and/or metabolic syndrome, and more particularly diabetes type 2, NASH, NAFLD, and/or metabolic syndrome in a human subject. In some embodiments, the mutant FGF-21 peptide conjugate is used in the preparation of a medicament for the treatment of diabetes type 2, NAFLD, NASH and/or metabolic syndrome, and more particularly diabetes type 2, NAFLD, NASH, and/or metabolic syndrome in a human subject.

In some embodiments, the mutant FGF-21 peptide conjugate has surprising therapeutic properties including an improved half-life, which is estimated to be ~80 hours in humans, and the ability to reduce at least one of HbA1c (a stable indicator of glycemic index), serum triglyceride levels, or serum insulin levels in a subject in need thereof. Such subjects include, without limitation, a subject who is suspected of having diabetes and/or a related disease/s (e.g., diabetes type 2, NAFLD, NASH, and/or metabolic syndrome) or who has diabetes and/or a related disease/s (e.g., diabetes type 2, NAFLD, NASH, and/or metabolic syndrome). Mutant FGF-21 peptide conjugates comprising a 20 kDa PEG residue also exhibit high bioavailability as reflected by 38% bioavailability in mice and rats, and 56% bioavailability in monkeys.

In some embodiments, a mutant Fibroblast Growth Factor-21 (FGF-21) peptide conjugate is described herein comprising
i) a mutant FGF-21 peptide comprising the amino acid sequence of SEQ ID NO: 2,
ii) a glycosyl moiety, and
iii) a 20 kDa polyethylene glycol (PEG),
wherein the mutant FGF-21 peptide is attached to the glycosyl moiety by a covalent bond between a threonine at amino acid position 173 of SEQ ID NO: 2 and a first site of the glycosyl moiety and wherein the glycosyl moiety is attached to the 20 kDa PEG by a covalent bond between a second site of the glycosyl moiety and the 20 kDa PEG. In a particular embodiment thereof, the glycosyl moiety comprises at least one of an N-acetylgalactosamine (GalNAc) residue, a galactose (Gal) residue, a sialic acid (Sia) residue, a 5-amine analogue of a Sia residue, a mannose (Man) residue, mannosamine, a glucose (Glc) residue, an N-acetylglucosamine (GlcNAc) residue, a fucose residue, a xylose residue, or a combination thereof. In another particular embodiment, the glycosyl moiety comprises at least one of an N-acetylgalactosamine (GalNAc) residue, a galactose (Gal) residue, a sialic acid (Sia), or a combination thereof.

In a more particular embodiment thereof, the at least one Sia residue is a nine-carbon carboxylated sugar. Still more particularly, the at least one Sia residue is N-acetylneuraminic acid (2-keto-5-acetamido-3,5-dideoxy-D-glycero-D-galactononulopyranos-1-onic acid (Neu5Ac), N-glycolylneuraminic acid (Neu5Gc), 2-keto-3-deoxy-nonulosonic acid (KDN), or a 9-substituted sialic acid. In a more particular embodiment, the 9-substituted sialic acid is 9-O-lactyl-Neu5Ac, 9-O-acetyl-Neu5Ac, 9-deoxy-9-fluoro-Neu5Ac, or 9-azido-9-deoxy-Neu5Ac. In an even more particular embodiment, the glycosyl moiety comprises the structure -GalNAc-Sia-.

In some embodiments, the mutant FGF-21 peptide conjugate described herein comprises the 20 kDa PEG moiety attached to the glycosyl moiety by a covalent bond to a linker, wherein the linker comprises at least one amino acid residue. Exemplary amino acids include: polar, but neutral amino acids (e.g., serine, threonine, cysteine, tyrosine, asparagine, and glutamine) and non-polar amino acids with relatively simple side chains (e.g. glycine, alanine, valine, leucine). In a particular embodiment, the at least one amino acid residue is at least one glycine (Gly). In a still more particular embodiment, the mutant FGF-21 peptide conjugate comprises the structure -GalNAc-Sia-Gly-PEG (20 kDa).

In some embodiments, the mutant FGF-21 peptide conjugate comprises the structure:

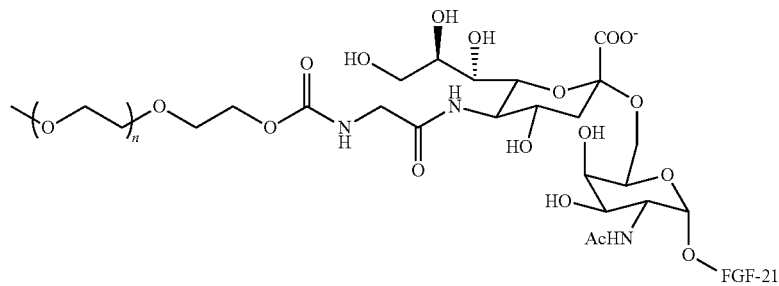

wherein n is an integer selected from 450 to 460.

A mutant FGF-21 peptide conjugate described herein may comprise a 20 kDa PEG which is a linear or branched PEG. In a more particular embodiment, the 20 kDa PEG is a linear PEG. In a still more particular embodiment, the 20 kDa PEG is a 20 kDa methoxy-PEG.

In a particular embodiment, the mutant FGF-21 peptide conjugate comprises:
- a mutant FGF-21 peptide comprising a threonine at amino acid position 173 of SEQ ID NO: 2 to which a glycosyl moiety is attached by a covalent bond;
- wherein the glycosyl comprises the structure GalNAc-Sia;
- a glycine attached to the Sia;
- and a linear 20 kDa PEG, wherein the 20 kDa PEG is a 20 kDa methoxy-PEG. The structure for which is presented below:

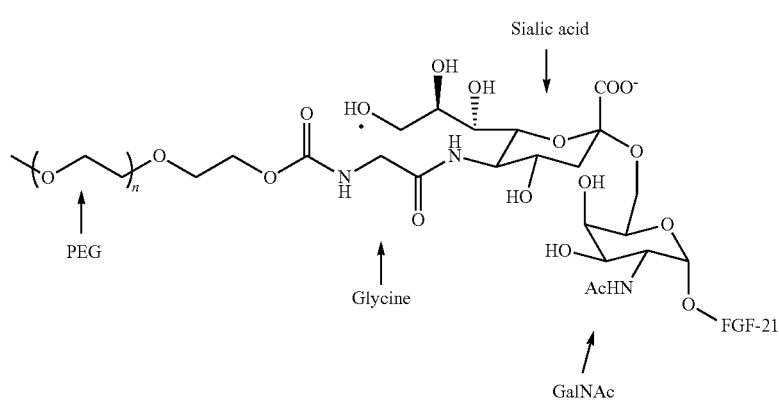

FIG. 4 is a table showing the safety summary according to some embodiments.

FIGS. 5A and 5B show the pharmacokinetics of the compounds described herein as single dose according to some embodiments. PK profiles are generally dose proportional with $T_{1/2}$ range from about 53 hours to 100 hours.

FIGS. 6A and 6B are graphs showing the mean percentage change at day 8 and day 15 of rom baseline in triglycerides (%) according to some embodiments.

FIG. 7 is a graph showing the mean percentage change over time of from baseline in triglycerides (%) according to some embodiments.

FIGS. 8A and 8B are graphs showing the mean percentage change at day 8 and day 15 of rom baseline in total cholesterol (%) according to some embodiments.

FIGS. 9A and 9B are graphs showing the mean percentage change at day 8 and day 15 of rom baseline in LDL cholesterol (%) according to some embodiments.

FIGS. 10A and 10B are graphs showing the mean percentage change at day 8 and day 15 of rom baseline in HDL cholesterol (%) according to some embodiments.

FIG. 11 is a table showing comparison of study population to other FGF-21 SAD studies.

FIG. 12 is a table showing the phase 1 study comparison vs other FGF-21 products.

FIG. 13 is a table showing the phase 1 study comparison vs other FGF-21 products.

FIG. 14 is a table showing the phase 1 study comparison vs thyroid hormone receptor beta agonists and FXR.

FIG. 15 shows the pERK Functional Assay standard procedure according to some embodiments.

BRIEF DESCRIPTION OF THE DRAWINGS

FIG. 2 is a table showing the baseline demographics design according to some embodiments.

FIG. 3 is a table showing the baseline laboratory parameters according to some embodiments.

FIGS. 16A and 16C show the results of the pERK functional assay in KLB only expressing cells using FGF-21. FIGS. 16B and 16D show the results of the pERK functional assay in KLB only expressing cells using BIO89-100 according to some embodiments. In KLB expressing cells, FGF-21 and BIO89-100 were not active in ERK phosphorylation (pERK).

FIGS. 17A and 17C show the results of the pERK functional assay in KLB/FGFR1 expressing cells using FGF-21. FIGS. 17B and 17D show the results of the pERK functional assay in KLB/FGFR1 expressing cells using BIO89-100 according to some embodiments. Both FGF-21 and and BIO89-100 activate KLB-FGFR1 cells. BIO89-100 showed 15 to 20 fold increase in potency sensitivity over FGF-21 in pERK assay.

FIGS. 19A and 19C show the results of the pERK functional assay in KLB/FGFR3 expressing cells using FGF-21. FIGS. 19B and 19D show the results of the pERK functional assay in KLB/FGFR3 expressing cells using BIO89-100 according to some embodiments. In KLB/FGFR3 expressing cells, BIO89-100 showed a comparable potency to FGF-21.

FIGS. 20A and 20C show the results of the pERK functional assay in KLB/FGFR4 expressing cells using FGF-21. FIGS. 20B and 20D show the results of the pERK functional assay in KLB/FGFR4 expressing cells using BIO89-100 according to some embodiments. In KLB/FGFR4 expressing cells, FGF-21 and BIO89-100 were almost not active, with less than 2-fold increase in pERK at the highest concentration of 3000 nM.

FIG. 21 shows a summary of FGF-21 vs BIO89-100 according to some embodiments showing that BIO89-100 was more potent than FGF-21 but with similar activity.

FIGS. 23A and 23C show the results of the pERK functional assay in KLB/FGFR1 expressing cells using FGF-19. FIGS. 23B and 23D show the results of the pERK functional assay in KLB/FGFR1 expressing cells using FGF-21 according to some embodiments.

FIGS. 24A and 24C show the results of the pERK functional assay in KLB/FGFR2 expressing cells using FGF-19. FIGS. 24B and 24D show the results of the pERK functional assay in KLB/FGFR2 expressing cells using FGF-21 according to some embodiments.

FIGS. 25A and 25C show the results of the pERK functional assay in KLB/FGFR3 expressing cells using FGF-19. FIGS. 25B and 25D show the results of the pERK functional assay in KLB/FGFR3 expressing cells using FGF-21 according to some embodiments.

FIGS. 26A and 26C show the results of the pERK functional assay in KLB/FGFR4 expressing cells using FGF-19. FIGS. 26B and 26D show the results of the pERK functional assay in KLB/FGFR4 expressing cells using FGF-21 according to some embodiments. There was no activity of FGF-21 while activity and potency for FGF-19.

FIGS. 29A and 29D show the results of the pERK functional assay in KLB/FGFR2 expressing cells using EGF. FIGS. 29B and 29E show the results of the pERK functional assay in KLB/FGFR2 expressing cells using FGF-21. FIGS. 29C and 29F show the results of the pERK functional assay in in KLB/FGFR2 expressing cells using FGF-23.

FIGS. 30A and 30D show the results of the pERK functional assay in KLB/FGFR3 expressing cells using EGF. FIGS. 30B and 30E show the results of the pERK functional assay in KLB/FGFR3 expressing cells using FGF-21. FIGS. 30C and 30F show the results of the pERK functional assay in in KLB/FGFR3 expressing cells using FGF-23.

FIGS. 31A and 31D show the results of the pERK functional assay in KLB/FGFR4 expressing cells using EGF. FIGS. 31CB and 31E show the results of the pERK functional assay in KLB/FGFR4 expressing cells using FGF-21. FIGS. 31C and 31F show the results of the pERK functional assay in in KLB/FGFR4 expressing cells using FGF-23.

FIGS. 33A-33F show the comparison of FGF-21 and BIO89-100 potency.

FIGS. 34A-34F show the potency of FGF-21 in FGFR expressing cells (dose response curve of 3 independent experiments).

FIGS. 35A-35G show the potency of FGF-21 in FGFR expressing cells (mean of 3 independent experiments).

FIGS. 36A-36F show the potency of BIO89-100 in FGFR expressing cell (dose response curve of 2 independent experiments)s.

FIGS. 37A-37G show the potency of BIO89-100 in FGFR expressing cells (mean of 2 independent experiments).

Figure 1:
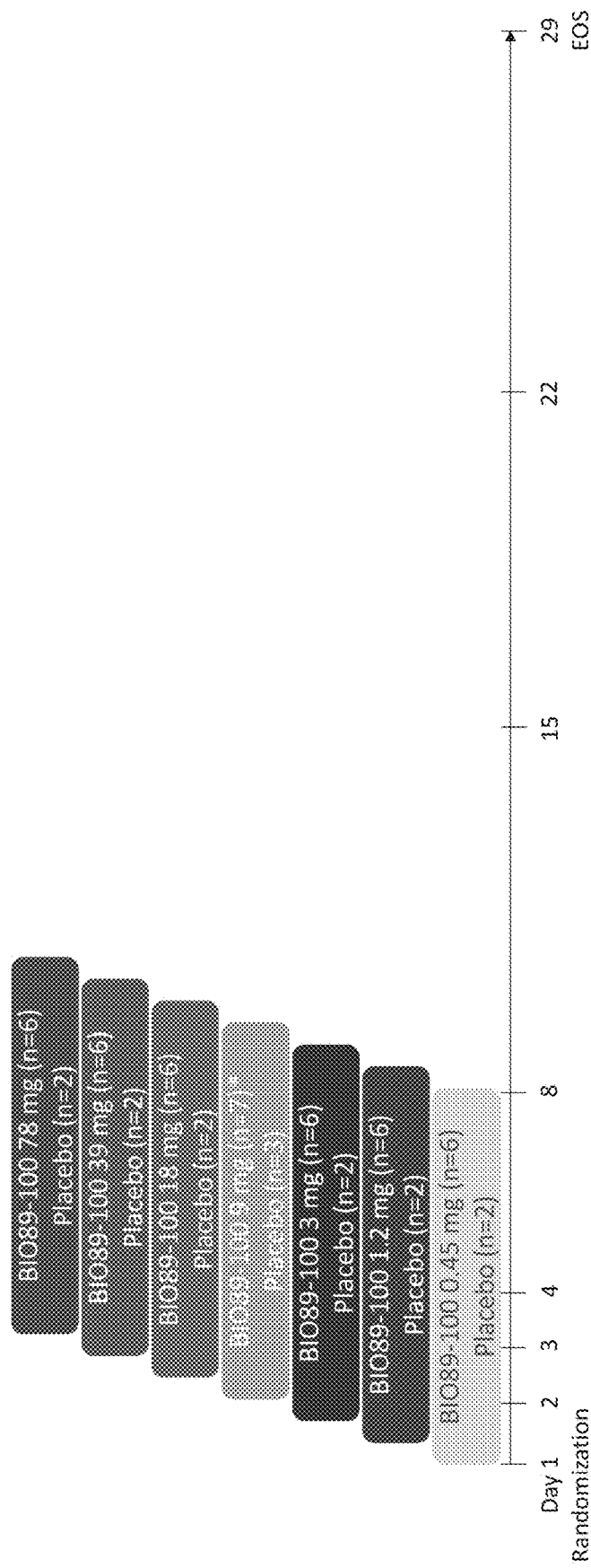
FIG. 1 represents the single ascending dose (SAD) study design according to some embodiments.

Among those benefits and improvements that have been disclosed, other objects and advantages of this invention will become apparent from the following description taken in conjunction with the accompanying figures. Detailed embodiments of the present invention are disclosed herein; however, it is to be understood that the disclosed embodiments are merely illustrative of the invention that may be embodied in various forms. In addition, each of the examples given in connection with the various embodiments of the invention are intended to be illustrative, and not restrictive.

Definitions

For the sake of clarity and readability, the following definitions are provided. Any technical feature mentioned for these definitions may be read on each and every embodiment of the invention. Additional definitions and explanations may be specifically provided in the context of these embodiments. Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and nucleic acid chemistry and hybridization are those well-known and commonly employed in the art. Standard techniques are used for nucleic acid and peptide synthesis. The techniques and procedures are generally performed according to conventional methods in the art and various general references (e.g., Sambrook et al., 1989, Molecular Cloning: A Laboratory Manual, 2d ed. Cold Spring Harbor Laboratory Press, Cold Spring Harbor, N.Y.), which are provided throughout this document.

Enzyme: Enzymes are catalytically active biomolecules that perform biochemical reactions such as the transfer of glycosyl moieties or modified glycosyl moieties from the respective glycosyl donors to an amino acid of FGF-21 or to another glycosyl moiety attached to the peptide.

Protein: A protein typically comprises one or more peptides or polypeptides. A protein is typically folded into a 3-dimensional form, which may be required for the protein to exert its biological function. The sequence of a protein or peptide is typically understood to be in the order, i.e. the succession of its amino acids.

Recombinant protein: The term "recombinant protein" refers to proteins produced in a heterologous system, that is, in an organism that naturally does not produce such a protein, or a variant of such a protein, i.e. the protein or peptide is "recombinantly produced". Typically, the heterologous systems used in the art to produce recombinant proteins are bacteria (e.g., *Escherichia* (*E.*) *coli*), yeast (e.g., *Saccharomyces* (*S.*) *cerevisiae*) or certain mammalian cell culture lines.

Expression host: An expression host denotes an organism which is used for recombinant protein production. General expression hosts are bacteria, such as *E. coli*, yeasts, such as *Saccharomyces cerevisiae* or *Pichia pastoris*, or also mammal cells, such as human cells.

RNA, mRNA: RNA is the usual abbreviation for ribonucleic acid. It is a nucleic acid molecule, i.e. a polymer consisting of nucleotides. These nucleotides are usually adenosine-monophosphate, uridine-monophosphate, guanosine-monophosphate and cytidine-monophosphate monomers which are connected to each other along a so-called backbone. The backbone is formed by phosphodiester bonds between the sugar, i.e. ribose, of a first and a phosphate moiety of a second, adjacent monomer. The specific succession of the monomers is called the RNA sequence.

DNA: DNA is the usual abbreviation for deoxyribonucleic acid. It is a nucleic acid molecule, i.e. a polymer consisting of nucleotide monomers. These nucleotides are usually deoxy-adenosine-monophosphate, deoxy-thymidine-monophosphate, deoxy-guanosine-monophosphate and deoxy-cytidine-monophosphate monomers which are—by themselves—composed of a sugar moiety (deoxyribose), a base moiety and a phosphate moiety, and polymerized by a characteristic backbone structure. The backbone structure is, typically, formed by phosphodiester bonds between the sugar moiety of the nucleotide, i.e. deoxyribose, of a first and a phosphate moiety of a second, adjacent monomer. The specific order of the monomers, i.e. the order of the bases linked to the sugar/phosphate-backbone, is called the DNA-sequence. DNA may be single-stranded or double-stranded. In the double stranded form, the nucleotides of the first strand typically hybridize with the nucleotides of the second strand, e.g. by A/T-base-pairing and G/C-base-pairing.

Sequence of a nucleic acid molecule/nucleic acid sequence: The sequence of a nucleic acid molecule is typically understood to be in the particular and individual order, i.e. the succession of its nucleotides.

Sequence of amino acid molecules/amino acid sequence: The sequence of a protein or peptide is typically understood to be in the order, i.e. the succession of its amino acids.

Sequence identity: Two or more sequences are identical if they exhibit the same length and order of nucleotides or amino acids. The percentage of identity typically describes the extent, to which two sequences are identical, i.e. it typically describes the percentage of nucleotides that correspond in their sequence position to identical nucleotides of a reference sequence, such as a native or wild type sequence. For the determination of the degree of identity, the sequences to be compared are considered to exhibit the same length, i.e. the length of the longest sequence of the sequences to be compared. This means that a first sequence consisting of 8 nucleotides/amino acids is 80% identical to a second sequence consisting of 10 nucleotides/amino acids comprising the first sequence. In other words, in the context of the present invention, identity of sequences particularly relates to the percentage of nucleotides/amino acids of a sequence, which have the same position in two or more sequences having the same length. Gaps are usually regarded as non-identical positions, irrespective of their actual position in an alignment.

Newly introduced amino acids: "Newly introduced amino acids" denote amino acids which are newly introduced into an amino acid sequence in comparison to a native/wild type amino acid sequence. Usually by mutagenesis, the native amino acid sequence is changed in order to have a certain amino acid side chain at a desired position within the amino acid sequence. In the present invention, in particular the amino acid threonine is newly introduced into the amino acid sequence on the C-terminal side adjacent to a proline residue.

Functional group: The term is to be understood according to the skilled person's general understanding in the art and denotes a chemical moiety which is present on a molecule, in particular on the peptide or amino acid of the peptide or glycosyl residue attached to the peptide, and which may participate in a covalent or non-covalent bond to another chemical molecule, i.e. which allows e.g. the attachment of a glycosyl residue or PEG.

Native amino acid sequence: The term is to be understood according to the skilled person's general understanding in the art and denotes the amino acid sequence in the form of its occurrence in nature without any mutation or amino acid amendment by man. It is also called "wild-type sequence". "Native FGF-21" or "wild-type FGF-21" denotes FGF-21 having the amino acid sequence as it occurs in nature, such as the (not mutated) amino acid sequence of human FGF-21 as depicted in SEQ ID NO: 1. The presence or absence of an N-terminal methionine, which depends on the used expression host, usually does not change the status of a protein being considered as having its natural or native/wild-type sequence.

Mutated: The term is to be understood according to the skilled person's general understanding in the art. An amino acid sequence is called "mutated" if it contains at least one additional, deleted or exchanged amino acid in its amino acid sequence in comparison to its natural or native amino acid sequence, i.e. if it contains an amino acid mutation. Mutated proteins are also called mutants. In the present invention, a mutated FGF-21 peptide is particularly a peptide having an amino acid exchange adjacent to a proline residue on the C-terminal side of the proline residue. Thereby a consensus sequence for O-linked glycosylation is introduced into FGF-21 such that the mutant FGF-21 peptide comprises a newly introduced O-linked glycosylation side. Amino acid exchanges are typically denoted as follows: $S^{172}T$ which means that the amino acid serine at position 172, such as in the amino acid sequence of SEQ ID NO: 1, is exchanged by the amino acid threonine.

Pharmaceutically effective amount: A pharmaceutically effective amount in the context of the invention is typically understood to be an amount that is sufficient to induce a pharmaceutical effect.

Therapy/treatment: The term "therapy" refers to "treating" or "treatment" of a disease or condition, inhibiting the disease (slowing or arresting its development), providing relief from the symptoms or side-effects of the disease (including palliative treatment), and relieving the disease (causing regression of the disease).

Therapeutically effective amount: is an amount of a compound that is sufficient to treat a disease or condition, inhibit the disease or condition, provide relief from symptoms or side-effects of the disease, and/or cause regression of the disease or condition.

Half-life: The term "half-life", as used herein in the context of administering a mutant FGF-21 peptide and/or conjugate thereof, is defined as the time required for the plasma concentration of a drug, i.e. of the mutant FGF-21 peptide and/or conjugate, in a subject to be reduced by one half.

O-linked glycosvlation: "O-linked glycosylation" takes place at serine or threonine residues (Tanner et al., Biochim. Biophys. Acta. 906:81-91 (1987); and Hounsell et al, Glycoconj. J. 13:19-26 (1996)). In the present invention, O-linked glycosylation sites, which are amino acid motifs in the amino acid sequence of a peptide which are recognized by glycosyl transferases as attachment points for glycosyl residues, include the amino acid motif proline-threonine (PT) not present in the native/wild-type amino acid sequence. In particular, the threonine residue is newly introduced adjacent to a proline and on the C-terminal side of a proline residue. The glycosyl moiety is then attached to the —OH group of the threonine residue by the glycosyl transferase.

Newly introduced O-linked glycosylation side: "Newly introduced O-linked glycosylation side" denotes an O-linked glycosylation side which did not exist in the native or wild-type FGF-21 before introducing a threonine adjacent to and on the C-terminal side of a proline residue as described herein.

Adjacent: Adjacent denotes the amino acid immediately next to another amino acid in the amino acid sequence, either on the N-terminal or on the C-terminal side of the respective amino acid. In the present invention, e.g. the newly introduced threonine residue is adjacent to a proline residue on the C-terminal side of a proline residue.

Glycosyl moiety: A glycosyl moiety is a moiety consisting of one or more, identical or different glycosyl residues which links the mutant FGF-21 peptide to a polyethylene glycol (PEG), thereby forming a conjugate comprising a peptide, glycosyl moiety and PEG. The glycosyl moiety can be a mono-, di-, tri-, or oligoglycosyl moiety. The glycosyl moiety may comprise one or more sialic acid residues, one or more N-acetylgalactosamine (GalNAc) residues, one or more galactose (Gal) residues and others. The glycosyl moiety may be modified, such as with a PEG or methoxy-PEG (m-PEG), an alkyl derivative of PEG.

Glycoconjugation: "Glycoconjugation", as used herein, refers to the enzymatically mediated conjugation of a PEG-modified glycosyl moiety to an amino acid or glycosyl residue of a (poly)peptide, e.g. a mutant FGF-21 of the present invention. A subgenus of "glycoconjugation" is "glyco-PEGylation" in which the modifying group of the modified glycosyl moiety is PEG or m-PEG. The PEG may be linear or branched. Typically, a branched PEG has a central branch core moiety and a plurality of linear polymer chains linked to the central branch core. PEG is commonly used in branched forms that can be prepared by addition of ethylene oxide to various polyols, such as glycerol, pentaerythritol and sorbitol. The central branch moiety can also be derived from several amino acids, such as lysine. The branched PEG can be represented in general form as $R(\text{-PEG-OX})_m$ in which R represents the core moiety, such as glycerol or pentaerythritol, X represents a capping group or an end group, and m represents the number of arms. The terms "glyco-PEG" and "glycosyl-PEG" are used interchangeably and denote a chemical moiety consisting of PEG or methoxy-PEG (mPEG or m-PEG), one or more glycosyl residues (or glycosyl moieties), and optionally a linker between PEG/methoxy-PEG and the glycosyl moieties, such as an amino acid, e.g. glycine. An example of a glycosyl-PEG/glyco-PEG moiety is PEG-sialic acid (PEG-Sia). It should be noted that the terms "glyco-PEG" and "glycosyl-PEG" as well as "PEG-sialic acid" and "PEG-Sia" as well as similar terms for glyco-PEG moieties may or may not include a linker between PEG and the glycosyl moiety or moieties, i.e. "PEG-sialic acid" encompasses e.g. PEG-sialic acid as well as PEG-Gly-sialic acid as well as mPEG-Gly-sialic acid.

Sequence motif: A sequence motif denotes a short amino acid sequence, such as that comprising only two amino acids, which is present at any possible position in a longer amino acid sequence, such as in the amino acid sequence of human FGF-21. Sequence motifs are e.g. denoted as $P^{172}T$ which means that the proline at position 172 is followed C-terminally immediately by a threonine residue.

Sialic acid: The term "sialic acid" or "Sia" refers to any member of a family of nine-carbon carboxylated sugars. The most common member of the sialic acid family is N-acetylneuraminic acid (2-keto-5-acetamido-3,5-dideoxy-D-glycero-D-galacto-nonulopyranos-1-onic acid (often abbreviated as Neu5Ac, NeuAc, or NANA). A second member of the family is N-glycolylneuraminic acid (Neu5Gc or NeuGc), in which the N-acetyl group of NeuAc is hydroxylated. A third sialic acid family member is 2-keto-3-deoxy-nonulosonic acid (KDN) (Nadano et al. (1986) J. Biol. Chem. 261:11550-11557). Also included are 9-substituted sialic acids such as a 9-O-C1-C6 acyl-Neu5Ac like 9-O-lactyl-Neu5Ac or 9-O-acetyl-Neu5Ac, 9-deoxy-9-fluoro-Neu5Ac and 9-azido-9-deoxy-Neu5Ac. For review of the sialic acid family, see e.g. Varki, Glycobiology 2:25-40 (1992)).

Pharmaceutically acceptable excipient: "Pharmaceutically acceptable" excipient includes any material, which when combined with the mutant FGF-21 peptide conjugate of the invention retains the conjugates' activity and is non-reactive with a subject's immune systems. Examples include, but are not limited to, any of the standard pharmaceutical excipients such as a phosphate buffered saline solution, water, salts, emulsions such as oil/water emulsion, and various types of wetting agents.

Pharmaceutical container: A "pharmaceutical container" is a container which is suitable for carrying a pharmaceutical composition and typically made of an inert material and sterile.

Administering: The term "administering" means oral administration, inhalation, administration as a suppository, topical contact, intravenous, intraperitoneal, intramuscular, intralesional, intranasal or subcutaneous administration, or the implantation of a slow-release device e.g., a mini-osmotic pump, to the subject. Administration is by any route including parenteral, and transmucosal (e.g. oral, nasal, vaginal, rectal, or transdermal). Parenteral administration includes e.g. intravenous, intramuscular, intraarteriole, intradermal, subcutaneous, intraperitoneal, intraventricular and intracranial. Other modes of delivery include, but are not limited to, the use of liposomal formulations, intravenous infusion, transdermal patches, etc.

Diabetes and diabetes related diseases: "Diabetes" is a well-known and well-characterized disease often referred to as diabetes mellitus. The term describes a group of metabolic diseases in which the person has high blood glucose levels (blood sugar), either because insulin production is inadequate, or because the body's cells do not respond properly to insulin, or both. Patients with high blood sugar will typically experience polyuria (frequent urination), they will become increasingly thirsty (polydipsia) and hungry (polyphagia). "Diabetes related diseases" are diseases characterized by the same symptoms such as obesity, polyuria, polydipsia and polyphagia.

Diabetes type 2: "Diabetes type 2" is the most common form of diabetes/diabetes mellitus. Diabetes type 2 most commonly develops in adulthood and is more likely to occur in people who are overweight and physically inactive. Unlike type 1 diabetes, which currently cannot be prevented, many of the risk factors for type 2 diabetes can be modified. The International Diabetes Foundation lists four symptoms that signal the need for diabetes testing: a) frequent urination, b) weight loss, c) lack of energy and d) excessive thirst. Insulin resistance is usually the precursor to diabetes type 2 a condition in which more insulin than usual is needed for glucose to enter the cells. Insulin resistance in the liver results in more glucose production while resistance in peripheral tissues means glucose uptake is impaired.

Nonalcoholic fatty liver disease (NAFLD) and Nonalcoholic steatohepatitis (NASH): are a condition where fat is deposited in the liver with subsequent liver damage and inflammation.

Metabolic syndrome: a defined cluster of risk factors (biochemical and physiological changes) that are associated with the development of type 2 diabetes and cardiovascular disease.

DETAILED DESCRIPTION OF THE INVENTION

Nonalcoholic fatty liver disease (NAFLD) and Nonalcoholic steatohepatitis (NASH) are chronic conditions where fat is deposited in the liver with subsequent liver damage and inflammation. To date there are no specific therapies for these disorders. Natural FGF-21 has a comparatively short half-life in vivo, with a reported circulating half-life ranging from 0.5 to 4 hours in rodents and non-human primates, which limits its clinical applicability. The half-life of recombinant human FGF-21 is 1-2 hours. To improve pharmacokinetic properties of FGF-21, various half-life extension strategies have been developed.

See also WO2019/043457, the entire content of which is incorporated herein in its entirety.

Abbreviations used herein include: PEG, poly(ethyleneglycol); PPG, poly(propyleneglycol); Ara, arabinosyl; Fru, fructosyl; Fuc, fucosyl; Gal, galactosyl; GalNAc, N-acetylgalactosaminyl; Glc, glucosyl; GlcNAc, N-acetylglucosaminyl; Man, mannosyl; ManAc, mannosaminyl acetate; Xyl, xylosyl; NeuAc, sialyl or N-acetylneuraminyl; Sia, sialyl or N-acetylneuraminyl; and derivatives and analogues thereof.

PEGylation

In glycoPEGylation, a PEG moiety may be transferred to an amino acid or glycosyl residue attached to an amino acid of the protein or peptide using a glycosyltransferase. The general final structure is protein-glycosyl moiety-optional further linker-PEG. A more particular final structure is protein-(N-, C- or internal) amino acid of the protein-one or more glycosyl residues-optional linker (e.g., amino acid linker)-linear or branched PEG moiety of various lengths, wherein the glycosyl moiety may comprise one or more glycosyl residues. The one or more glycosyl residues comprising at least part of the structure linking the protein to the PEG moiety may be any possible glycosyl residue. A diverse array of methods for glycoPEGylating proteins are known in the art and are described in detail herein below.

In some embodiments, Fibroblast Growth Factor-21 (FGF-21) peptide conjugates comprise:
i) a mutant FGF-21 peptide comprising at least one threonine (T) residue adjacent to at least one proline (P) residue on the C-terminal side of said at least one proline residue, thereby forming at least one O-linked glycosylation site which does not exist in the corresponding native FGF-21, wherein the corresponding native FGF-21 has an amino acid sequence that is at least 95% identical to SEQ ID NO: 1, and
ii) a 20 kDa polyethylene glycol (PEG), wherein said 20 kDa PEG is covalently attached to said mutant FGF-21 peptide at said at least one threonine residue via at least one glycosyl moiety.

In a particular embodiment, the mutant FGF-21 peptide conjugate comprises a mutant FGF-21 peptide comprising the amino acid sequence PT. In particular embodiments thereof, the mutant FGF-21 peptide comprises at least one amino acid sequence selected from the group consisting of P172T, P156T, P5T, P3T, P9T, P50T, P61T, P79T, P91T, P116T, P129T, P131T, P134T, P139T, P141T, P144T, P145T, P148T, P150T, P151T, P158T, P159T, P166T, P178T and combinations thereof, wherein the positions of proline and threonine are based on the amino acid sequence as depicted in SEQ ID NO: 1. In a more particular embodiment, the mutant FGF-21 peptide comprises at least one amino acid sequence selected from the group consisting of P172T, P156T, P5T and combinations thereof, particularly consisting of P172T, P156T and combinations thereof, wherein the positions of proline and threonine are based on the amino acid sequence as depicted in SEQ ID NO: 1. In a still more particular embodiment, the proline residue is located between amino acid 145 and the C-terminus of the mutant FGF-21 peptide, wherein the position of amino acid 145 is based on the amino acid sequence as depicted in SEQ ID NO: 1.

In another particular embodiment, the mutant FGF-21 peptide comprises the amino acid sequence P172T, wherein the positions of proline and threonine are based on the amino acid sequence as depicted in SEQ ID NO: 1.

In another particular embodiment, the mutant FGF-21 peptide comprises the mutations S173T and R176A, wherein the positions of the amino acids S and R are based on the amino acid sequence as depicted in SEQ ID NO: 1, particularly the mutant FGF-21 peptide comprises the amino acid sequence as depicted in SEQ ID NO: 2.

In another particular embodiment, the mutant FGF-21 peptide comprises the mutation Q157T, wherein the position of the amino acid Q is based on the amino acid sequence as depicted in SEQ ID NO: 1, particularly the mutant FGF-21 peptide comprises the amino acid sequence as depicted in SEQ ID NO: 4.

In another particular embodiment, the mutant FGF-21 peptide comprises the mutation D6T, wherein the position of the amino acid D is based on the amino acid sequence as depicted in SEQ ID NO: 1, particularly the mutant FGF-21 peptide comprises the amino acid sequence as depicted in SEQ ID NO: 5.

In other particular embodiments, the mutant FGF-21 peptide comprises an amino acid sequence selected from the group consisting of SEQ ID NOs: 2 to 28, particularly an amino acid sequence selected from the group consisting of SEQ ID NOs: 2 to 5, more particularly an amino acid sequence selected from the group consisting of SEQ ID NOs: 2 to 4, and most particularly the mutant FGF-21 peptide comprises the amino acid sequence as depicted in SEQ ID NO: 2.

In other particular embodiments, the mutant FGF-21 peptide conjugate comprises at least one glycosyl moiety comprising N-acetylgalactosamine (GalNAc), galactose (Gal) and/or sialic acid (Sia). In a particular embodiment thereof, the at least one glycosyl moiety comprises the structure -GalNAc-Sia-.

In other particular embodiments, the mutant FGF-21 peptide conjugate comprises a 20 kDa PEG moiety which is attached to the at least one glycosyl moiety via an amino acid residue, particularly glycine (Gly). In an even more particular embodiment, the mutant FGF-21 peptide conjugate comprises the structure -GalNAc-Sia-Gly-PEG (20 kDa). Still more particularly, the mutant FGF-21 peptide conjugate comprises the structure:

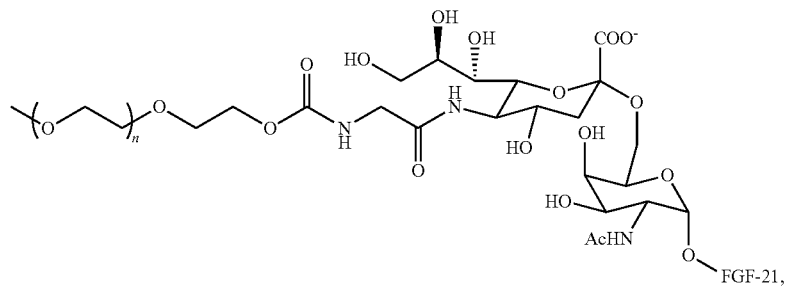

wherein n is an integer selected from 450 to 460.

In other particular embodiments, the mutant FGF-21 peptide conjugate comprises a 20 kDa PEG which is a linear or branched PEG, particularly a linear PEG. Still more particularly, the 20 kDa PEG is a 20 kDa methoxy-PEG.

In some embodiments, encompassed herein is a pharmaceutical composition comprising at least one mutant FGF-21 peptide conjugate described herein and a pharmaceutically acceptable carrier. In a particular embodiment, the mutant FGF-21 peptide conjugate is present in a concentration in the range from 0.1 mg/mL to 50 mg/mL, particularly from 1 mg/mL to 45 mg/mL, more particularly from 10 mg/mL to 40 mg/mL, most particularly in a concentration of 26±4 mg/mL. The buffering agent may be a Tris buffer. The buffering agent may be present in a concentration from 1 mM to 100 mM, particularly from 2 mM to 75 mM, more particularly from 5 mM to 50 mM, even more particularly from 10 mM to 25 mM, most particularly of 16±2 mM. The pH may be in the range from 6.0 to 8.5, particularly from 6.5 to 8.0, more particularly from 6.75 to 8.0, and most particularly is 7.5±0.3. The pharmaceutical composition may further comprise a salt, particularly an inorganic salt, more particularly NaCl. The pharmaceutical composition may comprise a salt which is present in a concentration from 30 mM to 200 mM, particularly from 40 mM to 150 mM, more particularly from 50 mM to 100 mM, most particularly of 56±2 mM. The pharmaceutical composition may further comprise a tonicity modifying agent. Suitable tonicity modifying agents include glycerol, amino acids, sodium chloride, proteins, or sugars and sugar alcohols, particularly the tonicity modifying agent is a sugar, and more particularly the tonicity modifying agent is sucrose. The tonicity modifying agent is present in a concentration of 50 mM to 200 mM, more particularly in a concentration of 100 mM to 175 mM, even more particularly is present in a concentration of 135 mM to 160 mM, and most particularly in a concentration of 150±2 mM. The pharmaceutical composition may further comprise a surfactant, particularly a non-ionic surfactant. The surfactant or non-ionic surfactant may be a polysorbate-based non-ionic surfactant, particularly polysorbate 20 or polysorbate 80, and more particularly polysorbate 20. The surfactant or non-ionic surfactant may be present in a concentration of 0.01 mg/mL to 1 mg/mL, particularly in a concentration of 0.05 to 0.5 mg/mL and more particularly in a concentration of 0.2±0.02 mg/mL. In a particular embodiment, the pharmaceutical composition comprises 0.1 mg/mL to 50 mg/mL of mutant FGF-21 peptide conjugate, 1 mM to 100 mM buffering agent, particularly Tris buffer, 30 mM to 200 mM salt, particularly NaCl, 50 mM to 200 mM tonicity modifying agent, particularly sucrose, and 0.01 mg/mL to 1 mg/mL surfactant or non-ionic surfactant, particularly polysorbate 20, and has a pH of 6.0 to 8.5.

A pharmaceutical container comprising at least one of the mutant FGF-21 peptide conjugates described herein and/or a pharmaceutical composition comprising same are also encompassed herein. Suitable pharmaceutical containers include, without limitation, a syringe, vial, infusion bottle, ampoule, carpoule, a syringe equipped with a needle protection system, and a carpoule within an injection pen.

In some embodiments, also encompassed herein is a method of producing the mutant FGF-21 peptide conjugate, comprising the steps of:

(1) recombinantly producing the mutant FGF-21 peptide in an expression host; and (2) enzymatically attaching to the mutant FGF-21 peptide of step (1) a PEG-glycosyl moiety, wherein the PEG has 20 kDa, thereby forming the mutant FGF-21 peptide conjugate. In a particular embodiment, the expression host is *Escherichia coli*. In a more particular embodiment, step (2) comprises a step (2a) of contacting the mutant FGF-21 peptide with a GalNAc donor and a GalNAc transferase under conditions suitable to transfer GalNAc from the GalNAc donor to the at least one threonine residue of the mutant FGF-21 peptide. In a still more particular embodiment, the GalNAc donor is UDP-GalNAc. In another particular embodiment, the GalNAc transferase is MBP-GalNAcT2. In another particular embodiment, step (2) further comprises a step (2b) of contacting the product of step (1) or of step (2a), if present, with a 20 kDa PEG-Sia donor and a sialyltransferase under conditions suitable to transfer 20 kDa PEG-Sia from the 20 kDa PEG-Sia donor to the at least one threonine residue of the mutant FGF-21 peptide or to the GalNAc at the mutant FGF-21 peptide if step (2a) is present. In a more particular embodiment, the 20 kDa PEG-Sia donor is 20 kDa PEG-Sia-CMP. In a still more particular embodiment, the sialyltransferase is ST6GalNAc1. In a still further particular embodiment, the 20 kDa PEG-Sia donor comprises the structure steps are performed, two quaternary ammonium (Q) strong anion exchange chromatography steps are performed. More particularly, wherein arginine is added in step (2) and/or, if present, in step (3), it is particularly at least 400 mM arginine. In a more particular embodiment, the method may further comprise a step (5), after step (3) and prior to step (2), of endotoxin removal, wherein the product of step (3) is filtered using an endotoxin removal filter.

In some embodiments, a mutant FGF-21 peptide conjugate obtainable by the above methods is encompassed, as are pharmaceutical compositions thereof that further comprise a pharmaceutically acceptable excipient or carrier.

Methods for Glycosylation and Glycoconjugation of FGF-21 Peptides

Post-expression in vitro modification of peptides and proteins is used to produce glycopeptides and glycoproteins. A diverse array of enzymes that transfer saccharide donor moieties is available, thereby making in vitro enzymatic synthesis of glycoconjugates with custom designed glycosylation patterns and glycosyl structures possible. See, for example, U.S. Pat. Nos. 5,876,980; 6,030,815; 5,728,554; 5,922,577; and published patent applications WO 98/31826; WO 01/88117; WO 03/031464; WO 03/046150; WO 03/045980; WO 03/093448; WO 04/009838; WO

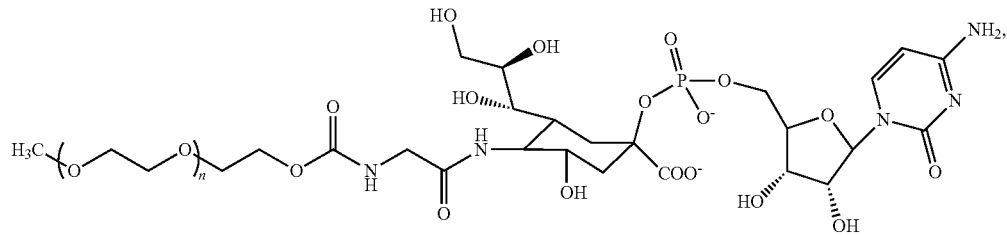

wherein n is an integer selected from 450 to 460.

In another particular embodiment, the method further comprises a step (3), after step (1) and prior to step (2), of purifying the mutant FGF-21 peptide after recombinant production. In a more particular embodiment, the method further comprises a step (4), after step (2), of purifying the mutant FGF-21 peptide conjugate formed in step (2). In another particular embodiment, the method, wherein step (3) comprises subjecting the mutant FGF-21 peptide and/or step (4) comprises subjecting the mutant FGF-21 peptide conjugate, the method may comprise ion exchange chromatography, affinity chromatography, filtration or combinations thereof. More particularly, wherein the step of purifying comprises one or more steps of ion exchange chromatography, it particularly comprises two steps of ion exchange chromatography. In another particular embodiment, wherein the ion exchange chromatography is an anion exchange chromatography, it is more particularly a strong anion exchange chromatography. More particularly, wherein the anion exchange chromatography employs a member, it is selected from the group consisting of a hydrophilic polyvinyl ether base matrix, polystyrene/divinyl benzene polymer matrix, trimethylammoniumethyl (TEAE), diethylaminoethanol (DEAE), agarose, a quaternary ammonium (Q) strong anion exchange chromatography and combinations thereof. In another particular embodiment, wherein in step (3) two anion exchange chromatography steps are performed, such steps use a hydrophilic polyvinyl ether base matrix. Still more particularly, wherein in step (4) quaternary ammonium (Q) strong anion exchange chromatography 05/089102; WO 06/050247; WO 12/016984; US2002/142370; US2003/040037; US2003/180835; US2004/063911; US2003/207406; and US2003/124645, each of which is incorporated herein by reference.

Glycosyl linking groups can comprise virtually any mono- or oligo-saccharide. The glycosyl linking groups can be attached to an amino acid either through the side chain or through the peptide backbone. Alternatively, the glycosyl linking groups can be attached to the peptide through a saccharyl moiety, which moiety can be a portion of an O-linked or N-linked glycan structure on the peptide.

In some embodiments, conjugates of glycosylated mutant FGF-21, which have glycosylation sites that do not exist in the corresponding wild-type FGF-21 sequence are produced. Such conjugates were formed by the enzymatic attachment of a modified sugar to the glycosylated FGF-21 peptide. The modified sugar, when interposed between the peptide and the modifying group on the sugar may be referred to herein as "a glycosyl linking group." In some embodiments, the generated mutant FGF-21 peptides have a desired group at one or more specific locations. More particularly, in some embodiments, glycosyltransferases are used to attach modified sugars to carbohydrate moieties on mutant FGF-21 glycopeptides.

FGF-21 Conjugates

In some embodiments, exemplary conjugates of a modified sugar and a mutant FGF-21 peptide are presented. More particularly, mutant FGF-21 peptide conjugates were made comprising a mutant FGF peptide and at least one modified sugar, wherein a first of the at least one modified sugar is linked to an amino acid of the peptide through a glycosyl linking group. As described herein, the amino acid to which the glycosyl linking group is attached is mutated to create a site recognized by the glycosyltransferase. In another exemplary embodiment, a mutant FGF-21 peptide conjugate can comprise a mutant FGF-21 peptide and a glycosyl group attached to the mutated amino acid residue of the mutant FGF-21 peptide.

In an exemplary embodiment, the glycosyl group is an intact glycosyl linking group. In another exemplary embodiment, the glycosyl group further comprises a modifying group. In another exemplary embodiment, the modifying group is a non-glycosidic modifying group. In another exemplary embodiment, the modifying group does not include a naturally occurring saccharide moiety.

Modified Sugars

In an exemplary embodiment, mutant FGF-21 peptides are reacted with a modified sugar, thus forming a peptide conjugate. A modified sugar comprises a "sugar donor moiety" as well as a "sugar transfer moiety". The sugar donor moiety is any portion of the modified sugar that will be attached to the peptide, either through a glycosyl moiety or amino acid moiety, as a conjugate described herein. The sugar donor moiety includes those atoms that are chemically altered during their conversion from the modified sugar to the glycosyl linking group of the mutant FGF-21 peptide conjugate. The sugar transfer moiety is any portion of the modified sugar that will be not be attached to the peptide as a conjugate described herein.

For modified sugars described herein, the saccharyl moiety may be a saccharide, a deoxy-saccharide, an amino-saccharide, or an N-acyl saccharide. The term "saccharide" and its equivalents, "saccharyl," "sugar," and "glycosyl" refer to monomers, dimers, oligomers and polymers. The sugar moiety is also functionalized with a modifying group. The modifying group is conjugated to the saccharyl moiety, typically, through conjugation with an amine, sulfhydryl or hydroxyl, e.g., primary hydroxyl, moiety on the sugar. In an exemplary embodiment, the modifying group is attached through an amine moiety on the sugar, e.g., through an amide, a urethane or a urea that is formed through the reaction of the amine with a reactive derivative of the modifying group.

Any saccharyl moiety can be utilized as the sugar donor moiety of the modified sugar. The saccharyl moiety can be a known sugar, such as mannose, galactose or glucose, or a species having the stereochemistry of a known sugar. The general formulae of these modified sugars are:

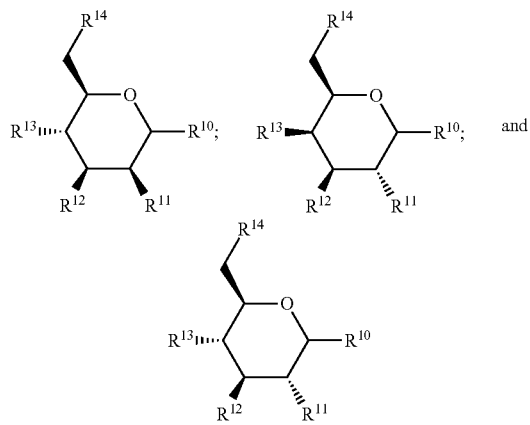

Other saccharyl moieties that are useful in methods described herein include, but are not limited to fucose and sialic acid, as well as amino sugars such as glucosamine, galactosamine, mannosamine, the 5-amine analogue of sialic acid and the like. The saccharyl moiety can be a structure found in nature or it can be modified to provide a site for conjugating the modifying group. For example, in one embodiment, the modified sugar provides a sialic acid derivative in which the 9-hydroxy moiety is replaced with an amine. The amine is readily derivatized with an activated analogue of a selected modifying group. Examples of modified sugars useful in methods described herein are presented in PCT Patent Application No. PCT/US05/002522, which is incorporated herein by reference in its entirety.

In a further exemplary embodiment, the invention utilizes modified sugars in which the 6-hydroxyl position is converted to the corresponding amine moiety, which bears a linker-modifying group cassette such as those set forth above. Exemplary glycosyl groups that can be used as the core of these modified sugars include Gal, GalNAc, Glc, GlcNAc, Fuc, Xyl, Man, and the like. A representative modified sugar according to this embodiment is set forth below:

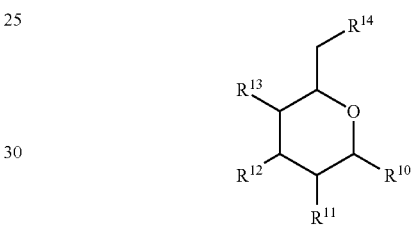

in which $R^{11}$-$R^{14}$ are members independently selected from H, OH, C(O)CH$_3$, NH, and NH C(O)CH$_3$. $R^{10}$ is a link to, e.g., another glycosyl residue (—O-glycosyl). $R^{14}$ is OR$^1$, NHR$^1$ or NH-L-R$^1$. $R^1$ and NH-L-R$^1$ are as described herein.

In a still further exemplary embodiment, the glycosyl groups used as the core of modified sugars in which the 6-hydroxyl position is converted to the corresponding amine moiety include Gal and/or GalNAc.

Glycosyl Linking Groups

In an exemplary embodiment, mutant FGF-21 peptide conjugates comprising a modified sugar described herein and a mutant FGF peptide are presented. In this embodiment, the sugar donor moiety (such as the saccharyl moiety and the modifying group) of the modified sugar becomes a "glycosyl linking group". The "glycosyl linking group" can alternatively refer to the glycosyl moiety which is interposed between the peptide and the modifying group.

In the exemplary embodiments that follow, the invention is illustrated by reference to the use of selected derivatives of furanose and pyranose. Those of skill in the art will appreciate that the structures and compositions set forth are generally applicable across the genus of glycosyl linking groups and modified sugars. The glycosyl linking group can, therefore, comprise virtually any mono- or oligo-saccharide.

In an exemplary embodiment, methods described herein utilize a glycosyl linking group that has the formula:

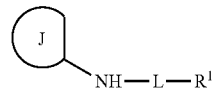

in which J is a glycosyl moiety, L is a bond or a linker and R¹ is a modifying group, e.g., a polymeric modifying group. Exemplary bonds are those that are formed between an NH₂ moiety on the glycosyl moiety and a group of complementary reactivity on the modifying group. For example, when R¹ includes a carboxylic acid moiety, this moiety may be activated and coupled with the NH² moiety on the glycosyl residue affording a bond having the structure NHC(O)R¹. J is preferably a glycosyl moiety that is "intact", not having been degraded by exposure to conditions that cleave the pyranose or furanose structure, e.g. oxidative conditions, e.g., sodium periodate.

Exemplary linkers include alkyl and heteroalkyl moieties. The linkers include linking groups, for example acyl-based linking groups, e.g., —C(O)NH—, —OC(O)NH—, and the like. The linking groups are bonds formed between components of the conjugates, e.g., between the glycosyl moiety and the linker (L), or between the linker and the modifying group (R'). Other exemplary linking groups are ethers, thioethers and amines. For example, in one embodiment, the linker is an amino acid residue, such as a glycine residue. The carboxylic acid moiety of the glycine is converted to the corresponding amide by reaction with an amine on the glycosyl residue, and the amine of the glycine is converted to the corresponding amide or urethane by reaction with an activated carboxylic acid or carbonate of the modifying group.

An exemplary species of NH-L-R¹ has the formula: —NH{C(O)(CH₂)$_a$NH}$_s${C(O)(CH₂)$_b$(OCH₂CH₂)$_c$O (CH₂)$_d$NH}$_t$R¹, in which the indices s and t are independently 0 or 1. The indices a, b and d are independently integers from 0 to 20, and c is an integer from 1 to 2500. Other similar linkers are based on species in which an —NH moiety is replaced by another group, for example, —S, —O or —CH₂.

As is understood in the art, one or more of the bracketed moieties corresponding to indices s and t can be replaced with a substituted or unsubstituted alkyl or heteroalkyl moiety.

More particularly, compounds described herein may comprise NH-L-R', wherein NH-L-R' is: NHC(O)(CH₂)$_a$NHC (O)(CH₂)$_b$(OCH₂CH₂)$_c$O(CH₂)$_d$NHR¹, NHC(O)(CH₂)$_b$ (OCH₂CH₂)$_c$O(CH₂)$_d$NHR¹, NHC(O)O(CH₂)$_b$(OCH₂ CH₂)$_c$O(CH₂)$_d$NHR¹, NH(CH₂)$_a$NHC(O)(CH₂)$_b$ (OCH₂CH₂)$_c$O(CH₂)$_d$NHR¹, NHC(O)(CH₂)$_a$NHR¹, NH(CH₂)$_a$NHR¹, and NHR¹. In these formulae, the indices a, b and d are independently selected from the integers from 0 to 20, preferably from 1 to 5. The index c is an integer from 1 to about 2500.

In an exemplary embodiment, c is selected such that the PEG moiety is approximately 1 kD, 5 kD, 10, kD, 15 kD, 20 kD, 25 kD, 30 kD, 35 kD, 40 kD, 45 kD, 50 kD, 55 kD, 60 kD or 65 kD.

In a more particular embodiment, the c is selected such that the PEG moiety ranges from 15-25 kD, 16-25 kD, 17-25 kD, 18-25 kD, 19-25 kD, 20-25 kD, 21-25 kD, 22-25 kD, 23-25 kD, 24-25 kD, 15-20 kD, 16-20 kD, 17-20 kD, 18-20 kD, 19-20 kD, 20-30 kD, 21-30 kD, 22-30 kD, 23-30 kD, 24-30 kD, 25-30 kD, 26-30 kD, 27-30 kD, 28-30 kD, 29-30 kD. In a still more particular embodiment, the c is selected such that the PEG moiety is 20 kD, 22 kD, 23 kD, 24 kD, 25 kD, 26 kD, 27 kD, 28 kD, 29 kD, or 30 kD.

For the purposes of clarity, the glycosyl linking groups in the remainder of this section are based on a sialyl moiety. However, one of skill in the art will recognize that another glycosyl moiety, such as mannosyl, galactosyl, glucosyl, or fucosyl, could be used in place of the sialyl moiety.

In an exemplary embodiment, the glycosyl linking group is an intact glycosyl linking group, in which the glycosyl moiety or moieties forming the linking group are not degraded by chemical (e.g., sodium metaperiodate) or enzymatic (e.g., oxidase) processes. Selected conjugates of the invention include a modifying group that is attached to the amine moiety of an amino-saccharide, e.g., mannosamine, glucosamine, galactosamine, sialic acid etc. In an exemplary embodiment, the invention provides a peptide conjugate comprising an intact glycosyl linking group having a formula that is selected from:

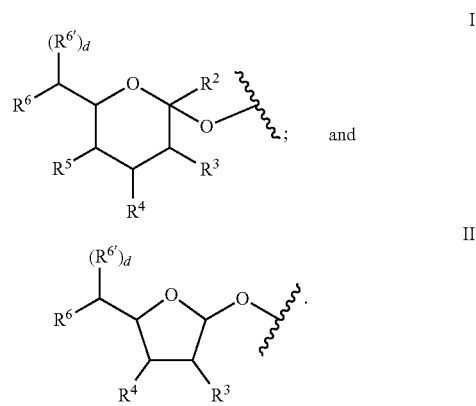

In Formulae I R² is H, CH₂OR⁷, COOR⁷ or OR⁷, in which R⁷ represents H, substituted or unsubstituted alkyl or substituted or unsubstituted heteroalkyl. When COOR⁷ is a carboxylic acid or carboxylate, both forms are represented by the designation of the single structure COO— or COOH. In Formulae I and II, the symbols R³, R⁴, R⁵, R⁶ and R⁶' independently represent H, substituted or unsubstituted alkyl, OR', NHC(O)R⁹. The index d is 0 or 1. R⁸ and R⁹ are independently selected from H, substituted or unsubstituted alkyl, substituted or unsubstituted heteroalkyl, sialic acid or polysialic acid. At least one of R³, R⁴, R⁵, R⁶ or R⁶' includes a modifying group. This modifying group can be a polymeric modifying moiety e.g., PEG, linked through a bond or a linking group. In an exemplary embodiment, R⁶ and R⁶', together with the carbon to which they are attached are components of the pyruvyl side chain of sialic acid. In a further exemplary embodiment, the pyruvyl side chain is functionalized with the polymeric modifying group. In another exemplary embodiment, R⁶ and R⁶', together with the carbon to which they are attached are components of the side chain of sialic acid and the polymeric modifying group is a component of R⁵.

Exemplary modifying group-intact glycosyl linking group cassettes according to this motif are based on a sialic acid structure, such as those having the formulae:

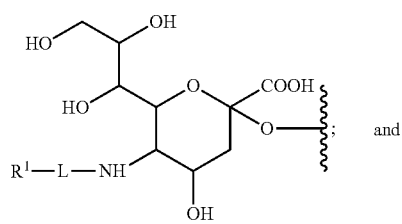

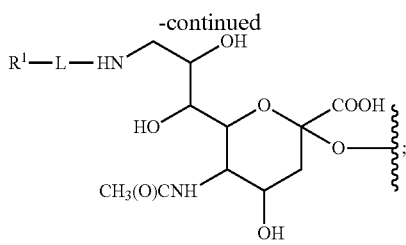

In the formulae above, $R^1$ and L are as described above. Further detail about the structure of exemplary $R^1$ groups is provided below.

In still a further exemplary embodiment, the conjugate is formed between a peptide and a modified sugar in which the modifying group is attached through a linker at the 6-carbon position of the modified sugar. Thus, illustrative glycosyl linking groups according to this embodiment have the formula:

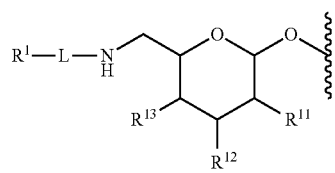

in which the radicals are as discussed above. Glycosyl linking groups include, without limitation, glucose, glucosamine, N-acetyl-glucosamine, galactose, galactosamine, N-acetylgalactosamine, mannose, mannosamine, N-acetyl-mannosamine, and the like.

In some embodiments, the present invention provides a mutant FGF-21 peptide conjugate comprising the following glycosyl linking group:

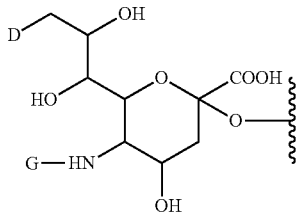

wherein D is a member selected from —OH and $R^1$-L-HN—; G is a member selected from H and $R^1$-L- and —C(O)(C$_1$-C$_6$)alkyl; $R^1$ is a moiety comprising a straight-chain or branched poly(ethylene glycol) residue; and L is a linker, e.g., a bond ("zero order"), substituted or unsubstituted alkyl and substituted or unsubstituted heteroalkyl. In exemplary embodiments, when D is OH, G is and when G is —C(O)(C$_1$-C$_6$)alkyl, D is $R^1$-L-NH—.

In some embodiments, the peptide conjugate includes a glycosyl linking group having the formula:

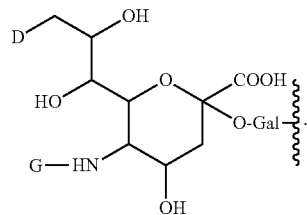

In some embodiments, the glycosyl linking group has the formula:

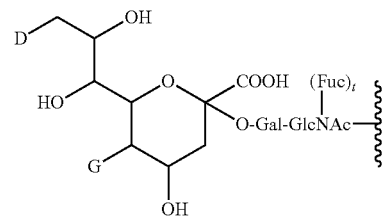

in which the index t is 0 or 1.

In some embodiments, the glycosyl linking group has the formula:

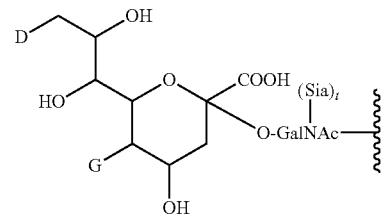

in which the index t is 0 or 1.

In some embodiments, the glycosyl linking group has the formula:

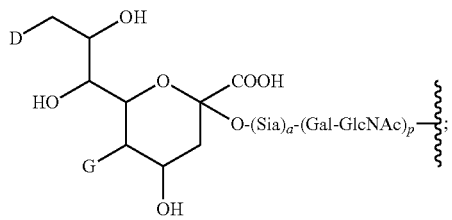

in which the index p represents and integer from 1 to 10; and a is either 0 or 1.

In some embodiments, a glycoPEGylated peptide conjugate is selected from the formulae set forth below:

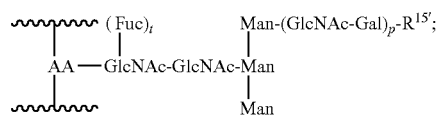

-continued

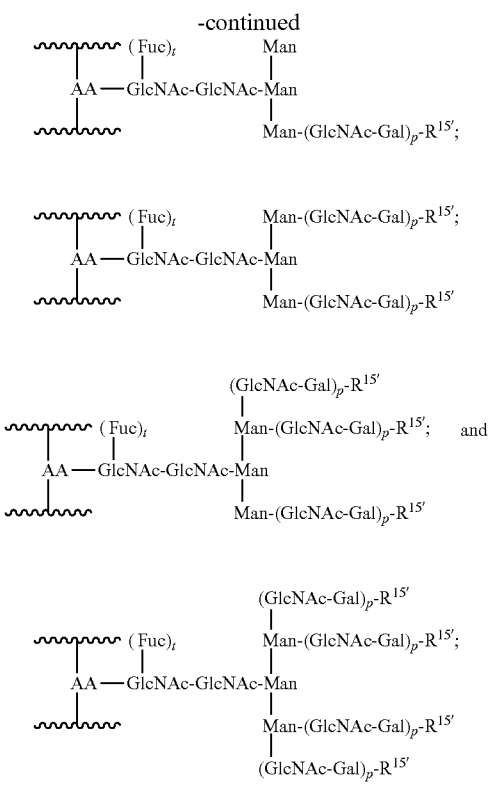

In the formulae above, the index t is an integer from 0 to 1 and the index p is an integer from 1 to 10. The symbol $R^{15'}$ represents H, OH (e.g., Gal-OH), a sialyl moiety, a sialyl linking group (i.e., sialyl linking group-polymeric modifying group (Sia-L-$R^1$), or a sialyl moiety to which is bound a polymer modified sialyl moiety (e.g., Sia-Sia-L-$R^1$) ("Sia-Sia$^{p'''}$")). Exemplary polymer modified saccharyl moieties have a structure according to Formulae I and II. An exemplary peptide conjugate of the invention will include at least one glycan having a $R^{15'}$ that includes a structure according to Formulae I or II. The oxygen, with the open valence, of Formulae I and II is preferably attached through a glycosidic linkage to a carbon of a Gal or GalNAc moiety. In a further exemplary embodiment, the oxygen is attached to the carbon at position 3 of a galactose residue. In an exemplary embodiment, the modified sialic acid is linked α2,3-to the galactose residue. In another exemplary embodiment, the sialic acid is linked α2,6-to the galactose residue.

In an exemplary embodiment, the sialyl linking group is a sialyl moiety to which is bound a polymer modified sialyl moiety (e.g., Sia-Sia-L-$R^1$) ("Sia-Sia$^{p'''}$"). Here, the glycosyl linking group is linked to a galactosyl moiety through a sialyl moiety:

An exemplary species according to this motif is prepared by conjugating Sia-L-$R^1$ to a terminal sialic acid of a glycan using an enzyme that forms Sia-Sia bonds, e.g., CST-11, ST8Sia-II, ST8Sia-III and ST8Sia-IV.

In another exemplary embodiment, the glycans on the peptide conjugates have a formula that is selected from the group:

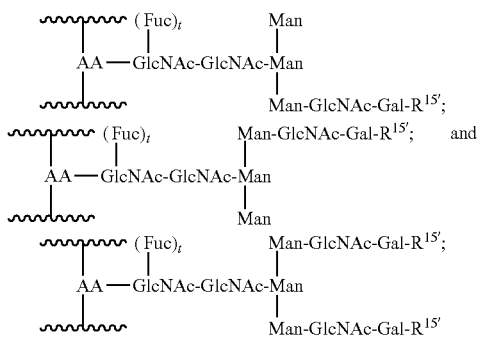

and combinations thereof.

In each of the formulae above, $R^{15'}$ is as discussed above. Moreover, an exemplary mutant FGF-21 peptide conjugate described herein will include at least one glycan with an $R^{15}$ moiety having a structure according to Formulae I or II.

In another exemplary embodiment, the glycosyl linking group comprises at least one glycosyl linking group having the formula:

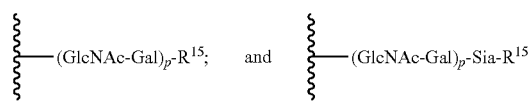

wherein $R^{15}$ is said sialyl linking group; and the index p is an integer selected from 1 to 10.

In an exemplary embodiment, the glycosyl linking moiety has the formula:

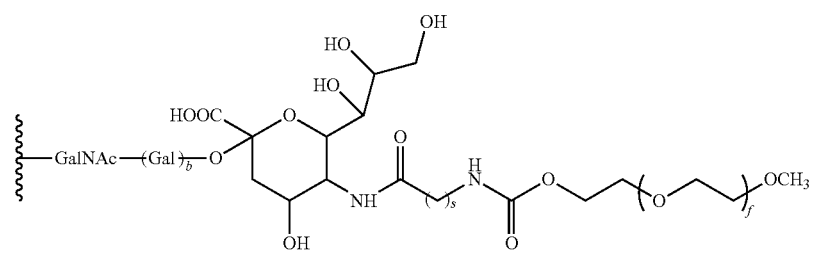

in which b is an integer from 0 to 1. The index s represents an integer from 1 to 10; and the index f represents an integer from 1 to 2500.

In an exemplary embodiment, the polymeric modifying group is PEG. In another exemplary embodiment, the PEG moiety has a molecular weight of 20-30 kDa. In exemplary embodiments, the PEG moiety has a molecular weight of 17 kDa, 18 kDa, 19 kDa, 20 kDa, 21 kDa, 22 kDa, 23 kDa, 24 kDa, 25 kDa, 26 kDa, 27 kDa, 28 kDa, 29 kDa, 30 kDa, 31 kDa, 32 kDa, or 33 kDa. In another exemplary embodiment, the PEG moiety has a molecular weight of 20 kDa. In another exemplary embodiment, the PEG moiety has a molecular weight of 30 kDa. In another exemplary embodiment, the PEG moiety has a molecular weight of about 5 kDa. In another exemplary embodiment, the PEG moiety has a molecular weight of about 10 kDa. In another exemplary embodiment, the PEG moiety has a molecular weight of about 40 kDa.

In an exemplary embodiment, the glycosyl linking group is a linear 10 kDa-PEG-sialyl, and one or two of these glycosyl linking groups are covalently attached to the peptide.

In an exemplary embodiment, the glycosyl linking group is a linear 20 kDa-PEG-sialyl, and one or two of these glycosyl linking groups are covalently attached to the peptide. In an exemplary embodiment, the glycosyl linking group is a linear 30 kDa-PEG-sialyl, and one or two of these glycosyl linking groups are covalently attached to the peptide. In an exemplary embodiment, the glycosyl linking group is a linear 5 kDa-PEG-sialyl, and one, two or three of these glycosyl linking groups are covalently attached to the peptide. In an exemplary embodiment, the glycosyl linking group is a linear 40 kDa-PEG-sialyl, and one or two of these glycosyl linking groups are covalently attached to the peptide.

In a still further exemplary embodiment, a mutant FGF-21 peptide is pegylated in accordance with methods described herein. In a particular embodiment, the mutant FGF-21 peptide comprises the mutations $S^{172}T$ and $R^{176}A$, wherein the positions of the amino acids S and R are based on the amino acid sequence as depicted in SEQ ID NO: 1. More particularly, the mutant FGF-21 peptide comprises the amino acid sequence as depicted in SEQ ID NO: 2. As detailed herein above, the at least one glycosyl moiety attached to the threonine residue and linking the newly introduced threonine residue to the PEG moiety may virtually be any possible glycosyl moiety. The only limitation is that it should be able to attach to threonine and that it should be able to be attached to PEG or m-PEG, more particularly via a linker, e.g. an amino acid residue, particularly glycine. In particular embodiment, the at least one glycosyl moiety comprises N-acetylgalactosamine (GalNAc), galactose (Gal) and/or sialic acid (Sia). In a more particular embodiment, the at least one glycosyl moiety comprises the structure -GalNAc-Sia-, i.e. two glycosyl moieties, namely GalNAc and Sia, wherein the PEG residue may be attached to GalNAc or Sia, particularly to Sia. The glycosyl moiety which is not attached to the PEG moiety may be attached to the newly introduced threonine residue.

In another particular embodiment, the 20 kDa PEG moiety is attached to the at least one glycosyl linker via a linker, e.g. an amino acid residue, particularly a small amino acid, such as alanine or glycine, more particularly via glycine (Gly). Hence, the PEG or m-PEG moiety is attached to the amino acid and the amino acid is attached to a glycosyl moiety, such as Sia. The glycosyl moiety is attached to the amino acid linker, if present, and to the newly introduced threonine residue in the mutant FGF-21 amino acid sequence. The amino acid residue is attached to PEG and the glycosyl residue via a method described in WO 03/031464 which is incorporated herein by reference.

In a particular embodiment, the mutant FGF-21 peptide (e.g., SEQ ID NO: 2) conjugate comprises the structure -GalNAc-Sia-Gly-PEG (20 kDa), wherein GalNAc is attached, e.g. to a newly introduced threonine residue and to Sia. Sia is further attached via a glycine residue to a PEG of 17 kDa, 18 kDa, 19 kDa, 20 kDa, 21 kDa, 22 kDa, 23 kDa, 24 kDa, 25 kDa, 26 kDa, 27 kDa, 28 kDa, 29 kDa, 30 kDa, 31 kDa, 32 kDa, or 33 kDa.

In a more particular embodiment, the mutant FGF-21 peptide (e.g., SEQ ID NO: 2) conjugate comprises the structure -GalNAc-Sia-Gly-PEG (20 kDa), wherein GalNAc is attached, e.g. to a newly introduced threonine residue and to Sia. Sia is further attached via a glycine residue to a PEG of 20 kDa, 21 kDa, 22 kDa, 23 kDa, 24 kDa, 25 kDa, 26 kDa, 27 kDa, 28 kDa, 29 kDa, or 30 kDa.

In a still more particular embodiment, the mutant FGF-21 peptide (e.g., SEQ ID NO: 2) conjugate comprises the structure -GalNAc-Sia-Gly-PEG (20 kDa), wherein GalNAc is attached, e.g. to a newly introduced threonine residue and to Sia. Sia is further attached via a glycine residue to a PEG of 20 kDa, 25 kDa, or 30 kDa. In a further particular embodiment, the mutant FGF-21 peptide (e.g., SEQ ID NO: 2) conjugate comprises the structure -GalNAc-Sia-Gly-PEG (20 kDa), wherein GalNAc is attached, e.g. to a newly introduced threonine residue and to Sia. Sia is further attached via a glycine residue to a PEG of 20 kDa or 30 kDa.

In a still further particular embodiment, the mutant FGF-21 peptide (e.g., SEQ ID NO: 2) conjugate comprises the structure -GalNAc-Sia-Gly-PEG (20 kDa), wherein GalNAc is attached, e.g. to a newly introduced threonine residue and to Sia. Sia is further attached via a glycine residue to a PEG of 20 kDa.

In a particular embodiment, the mutant FGF-21 peptide conjugate comprises the structure:

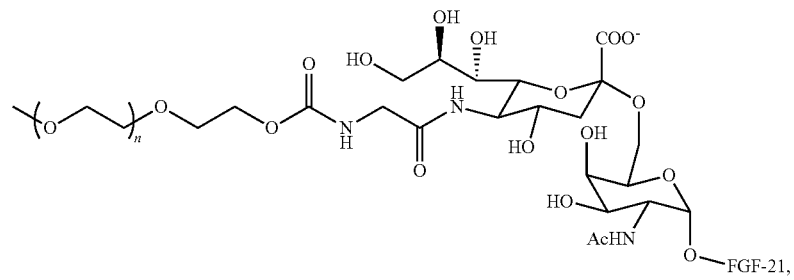

wherein n is an integer selected from 450 to 460.

The 20 kDa PEG may be linear or branched, more particularly the 20 kDa PEG, is a linear 20 kDa PEG. Further, the 20 kDa PEG is particularly a 20 kDa methoxy-PEG (mPEG, m-PEG). PEG and mPEG of different molecular weight can be obtained from various suppliers, such as from JenKem Technology USA, Plano, Tex., USA, or Merckle Biotec, Ulm, Germany. It is understood in the art that PEG 20 kDa means that the size of the PEG residues is 20 kDa in average and that the majority of the PEG residues are 20 kDa in size.

Mutant FGF-21 Peptides and Conjugates Thereof

As described herein, variants of Fibroblast Growth Factor-21 (FGF-21) having surprising properties, including variants having exceptionally long half-lives are produced, which variants are peptide conjugates comprising
i) a mutant FGF-21 peptide comprising at least one threonine (T) residue adjacent to at least one proline (P) residue on the C-terminal side of the at least one proline residue, thereby forming at least one O-linked glycosylation site which does not exist in the corresponding native FGF-21, wherein the corresponding native FGF-21 has an amino acid sequence that is at least 95% identical to SEQ ID NO: 1, and
ii) a 20-30 kDa polyethylene glycol (PEG), wherein said 20-30 kDa PEG is covalently attached to said mutant FGF-21 peptide at the at least one threonine residue via at least one glycosyl moiety.

For the attachment of the 20-30 kDa PEG residue, a threonine residue is introduced into the amino acid sequence of native FGF-21 adjacent to and on the C-terminal side of a proline residue which is already present in the amino acid sequence of native FGF-21, i.e. is a native proline residue. For this purpose, either (i) an additional threonine may be introduced immediately next to the native proline residue or (ii) the native amino acid which is present in the native amino acid sequence of FGF-21 adjacent to and located on the C-terminal side of a native proline residue is exchanged for a threonine residue. In the present invention, option (ii) is an exemplary embodiment. As described herein, more than one threonine residue may be introduced adjacent and C-terminal to a proline residue which is already present. A mutant FGF-21 of the present invention may thus comprise both threonine residues which have been additionally introduced and threonine residues which have been introduced instead of a native amino acid.

By the introduction of a new threonine residue on the C-terminal side and adjacent to a proline residue, a consensus sequence for O-glycosylation enzyme is formed. Because proline residues are typically found on the surface of proteins (in, e.g., turns, kinks, and/or loops), a design that calls for O-glycosylation and PEGylation thereto using a PEG-glycosyl moiety in close proximity to a proline residue benefits from the relative accessibility of the target attachment site for the glycosyl transferase that transfers the glycosyl or glycol-PEG moiety and the potential to accommodate the conjugated glycosyl and/or PEG structure without disruption of protein structure.

For introduction of the threonine residues into the native amino acid sequence of FGF-21, the general methods include Sambrook and Russell, Molecular Cloning, A Laboratory Manual (3rd ed. 2001); Kriegler, Gene Transfer and Expression: A Laboratory Manual (1990); and Ausubel et al., eds., Current Protocols in Molecular Biology (1994).

In a particular embodiment, the native FGF-21 amino acid sequence corresponds to the native amino acid sequence of human FGF-21 depicted in SEQ ID NO: 1.

In a particular embodiment, the mutant FGF-21 peptide comprises the amino acid sequence PT, i.e. a threonine residue C-terminally adjacent to a proline residue. The sequence PT is not present in the native FGF-21 amino acid sequence. Optionally, the mutant FGF-21 peptide comprises at least one amino acid sequence selected from the group consisting of $P^{172}T$ (e.g. SEQ ID NO: 2 or 3), $P^{156}T$ (e.g. SEQ ID NO: 4), $P^5T$ (e.g. SEQ ID NO: 5), $P^{61}T$ (e.g. SEQ ID NO: 6), $P^9T$ (e.g. SEQ ID NO: 7), $P^{50}T$ (e.g. SEQ ID NO: 8), $P^{61}T$ (e.g. SEQ ID NO: 9), $P^{79}T$ (e.g. SEQ ID NO: 10), $P^{91}T$ (e.g. SEQ ID NO: 11), $P^{116}T$ (e.g. SEQ ID NO: 12), $P^{120}T$ (e.g. SEQ ID NO: 13), $P^{125}T$ (e.g. SEQ ID NO: 14), $P^{129}T$ (e.g. SEQ ID NO: 15), $P^{131}T$ (e.g. SEQ ID NO: 16), $P^{134}T$ (e.g. SEQ ID NO: 17), $P^{139}T$ (e.g. SEQ ID NO: 18), $P^{141}T$ (e.g. SEQ ID NO: 19), $P^{144}T$ (e.g. SEQ ID NO: 20), $P^{145}T$ (e.g. SEQ ID NO: 21), $P^{148}T$ (e.g. SEQ ID NO: 22), $P^{150}T$ (e.g. SEQ ID NO: 23), $P^{151}T$ (e.g. SEQ ID NO: 24), $P^{158}T$ (e.g. SEQ ID NO: 25), $P^{159}T$ (e.g. SEQ ID NO: 26), $P^{166}T$ (e.g. SEQ ID NO: 27), $P^{178}T$ (e.g. SEQ ID NO: 28), and combinations thereof, wherein the positions of proline and threonine are based on the native amino acid sequence of FGF-21 as depicted in SEQ ID NO: 1, particularly the mutant FGF-21 peptide comprises at least one amino acid sequence selected from the group consisting of $P^{172}T$, $P^{156}T$, $P^5T$ and combinations thereof, more particularly consisting of $P^{172}T$, $P^{156}T$ and combinations thereof, and even more particularly the mutant FGF-21 peptide comprises the sequence motif $P^{172}T$, based on the amino acid sequence as depicted in SEQ ID NO: 1, wherein the positions of proline and threonine are based on the amino acid sequence as depicted in SEQ ID NO: 1.

In a particular embodiment, the proline residue is located between amino acid 145 and the C-terminus of the mutant FGF-21 peptide, wherein the position of amino acid 145 is based on the amino acid sequence as depicted in SEQ ID NO: 1. As demonstrated by results presented herein, the C-terminus of FGF-21 surprisingly tolerates attachment of PEG and in particular of glycosyl-PEG moieties. This was unexpected since the literature reports that the intact C-terminus is necessary for P-Klotho binding of FGF-21. In a particular embodiment, the mutant FGF-21 peptide comprises the mutations $S^{172}T$ and $R^{176}A$, wherein the positions of the amino acids S and R are based on the amino acid sequence as depicted in SEQ ID NO: 1, particularly the mutant FGF-21 peptide comprises the amino acid sequence as depicted in SEQ ID NO: 2. The mutation $R^{176}A$ has been found beneficial to the protein's overall stability after introducing the O-linked glycosylation site at threonine 173. By this mutation, the relatively large arginine side chain was removed and replaced by the small side chain of alanine. It is assumed that the smaller side chain of alanine interferes less with the voluminous glycosyl-PEG moiety to be attached to thindicae mutated FGF-21 peptide.

In an alternative embodiment, the mutant FGF-21 peptide comprises the mutation $Q^{157}T$, wherein the position of the amino acid Q is based on the amino acid sequence as depicted in SEQ ID NO: 1, particularly the mutant FGF-21 peptide comprises the amino acid sequence as depicted in SEQ ID NO: 4, or the mutation $D^6T$, wherein the position of the amino acid D is based on the amino acid sequence as depicted in SEQ ID NO: 1, particularly the mutant FGF-21 peptide comprises the amino acid sequence as depicted in SEQ ID NO: 5.

In a particular embodiment, the mutant FGF-21 peptide conjugate comprises an amino acid sequence selected from the group consisting of SEQ ID NOs: 2 to 28, more particularly an amino acid sequence selected from the group consisting of SEQ ID NOs: 2 to 5, even more particularly an amino acid sequence selected from the group consisting of SEQ ID NOs: 2 to 4, and most particularly the mutant FGF-21 peptide comprises the amino acid sequence as depicted in SEQ ID NO: 2.

Pharmaceutical Compositions and Methods of Treating

In some embodiments, the pharmaceutical compositions comprise the mutant FGF-21 peptide conjugate and a pharmaceutically acceptable carrier, such as water or a physiologically compatible buffer. The pharmaceutical compositions typically comprise a therapeutically effective or pharmaceutically active amount of the mutant FGF-21 peptide conjugate as active agent.

In some embodiments, the pharmaceutical compositions are suitable for use in a variety of drug delivery systems. Suitable formulations for use in the present invention are found in Remington's Pharmaceutical Sciences, Mack Publishing Company, Philadelphia, Pa., $17^{th}$ ed. (1985). The pharmaceutical compositions are intended for parenteral, intranasal, topical, oral, or local administration, such as by subcutaneous injection, aerosol inhalation, or transdermal adsorption, for prophylactic and/or therapeutic treatment. Commonly, the pharmaceutical compositions are administered parenterally, e.g., subcutaneously or intravenously.

In some embodiments, the invention provides compositions for parenteral administration which comprise the mutant FGF-21 peptide conjugate dissolved or suspended in an acceptable carrier, particularly an aqueous carrier, e.g., water, buffered water, saline, phosphate buffered saline (PBS) and the like. The compositions may also contain detergents such as Tween 20 and Tween 80; stabilizers such as mannitol, sorbitol, sucrose, and trehalose; and preservatives such as EDTA and m-cresol. The compositions may contain pharmaceutically acceptable auxiliary substances as required to approximate physiological conditions, such as pH adjusting and buffering agents, tonicity adjusting agents, wetting agents, detergents and the like.

In some embodiments, the pharmaceutical compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The compositions containing the FGF peptide conjugates can be administered for prophylactic and/or therapeutic treatments, in particular for the treatment of diabetes or diabetes related diseases, particularly for the treatment of diabetes type 2, NASH and metabolic syndrome. In therapeutic applications, compositions are administered to a subject already suffering from a disease or condition related to diabetes, in an amount sufficient to cure or at least partially arrest the symptoms of the disease and its complications. An amount adequate to accomplish this is defined as a "therapeutically effective amount" and usually depends the patient's state of health and weight. Efficacious doses range from 0.1 mg/kg to 6 mg/kg when tested in various animal models of NASH and type 2 diabetes.

In some embodiments, the present invention provides methods for treating a disease and/or a disorder or symptoms thereof which comprise administering a therapeutically effective amount of a compound (a mutant FGF-21 peptide conjugate described herein) or a pharmaceutical composition comprising same to a subject (e.g., a mammal such as a human). Thus, one embodiment is a method for treating a subject suffering from diabetes or a diabetes related disease (e.g., diabetes type 2, NAFLD, NASH or metabolic syndrome) or a symptom thereof. The method includes the step of administering to the mammal an amount of a compound described herein in an amount sufficient to treat the disease or disorder or symptom thereof or a composition comprising same, under conditions such that the disease or disorder is treated.

In some embodiments, the mutant FGF-21 peptide conjugate (e.g., 89Bio-100) is administered to a human subject at a therapeutic dosing regimen of from about 3 mg to about 27 mg once every week. In some embodiments, the mutant FGF-21 peptide conjugate (e.g., 89Bio-100) is administered to a human subject at a therapeutic dosing regimen of from about 18 mg to about 36 mg once every two weeks. In some embodiments, the mutant FGF-21 peptide conjugate (e.g., 89Bio-100) is administered to a human subject at a therapeutic dosing regimen of a single dose at 0.45 mg, 1.2 mg, 3 mg, 9.1 mg, 18.2 mg, 39 mg or 78 mg, or placebo at a 6:2 ratio (7:3 ratio for the 9.1 mg dose). See also Example 1 and Example 4 below.

In some embodiments, the therapeutic dosing regimen comprises a range of 3 mg to 27 mg; a range of 9 mg to 27 mg; a range of 18 mg to 27 mg; a range 3 mg to 9 mg; a range of 9 mg to 18 mg; a range of 18 mg to 27 mg; a range of 18 mg to 27 mg; a range of 3 mg to 18 mg; a range of 18 mg to 36 mg. In some embodiments, the therapeutic dosing regimen comprises a range of 3 mg to 50 mg; a range of 5 mg to 50 mg; a range of 10 mg to 50 mg; a range of 20 mg to 50 mg; a range of 30 mg to 50 mg; or a range of 40 mg to 50 mg; and any whole integer within any of the indicated ranges. In some embodiments, the therapeutic dosing regimen comprises a range of 5 mg to 40 mg; a range of 10 mg to 40 mg; a range of 20 mg to 40 mg; a range of 30 mg to 40 mg; or a range of 35 mg to 40 mg; and any whole integer within any of the indicated ranges. In some embodiments, the therapeutic dosing regimen comprises a range of 5 mg to 30 mg; a range of 10 mg to 30 mg; a range of 20 mg to 30 mg; or a range of 25 mg to 30 mg; and any whole integer within any of the indicated ranges. In some embodiments, the therapeutic dosing regimen comprises a range of 10 mg to 20 mg; or a range of 15 mg to 20 mg; and any whole integer within any of the indicated ranges. In some embodiments, the therapeutic dosing regimen comprises a dose of about 3 mg; about 9 mg; about 18 mg; or about 36 mg. The term "about" as used herein refers to an amount equal to 10% more or 10% less of the particularly indicated amount. For example, about 10 mg refers to a range of 9.0-11 mg. In yet another particular embodiment thereof, the therapeutic dosing regimen comprises a dose of 9.1 ng; about 18.2 mg; or about 39 mg.

The aforementioned therapeutic dosing regimens may be administered to a human in need thereof to treat at least one of diabetes (e.g., diabetes type 2), NAFLD, NASH, or metabolic syndrome. In some embodiments, the aforementioned therapeutic dosing regimens are administered to a human in need thereof to reduce triglyceride levels. In another particular embodiment, the aforementioned therapeutic dosing regimens are administered to a human to reduce triglyceride levels. (see for example, example 1)

The aforementioned therapeutic dosing regimens may also be administered to a human in need thereof to reduce cravings for sugary foods and/or beverages. (see for example, example 2)

In some embodiments, a pharmaceutical composition comprising any one of or at least one of the mutant FGF-21 peptide conjugates described herein and a pharmaceutically acceptable carrier is presented. The mutant FGF-21 peptide conjugate may be present in the pharmaceutical composition in a concentration in a range from 0.1 mg/mL to 50 mg/mL, particularly from 1 mg/mL to 45 mg/mL, more particularly from 10 mg/mL to 40 mg/mL, most particularly in a concentration of 26±4 mg/mL. In a particular embodiment, the pharmaceutical composition further comprises a buffering agent, particularly a Tris buffer. In another embodiment, the buffering agent is present in a concentration from 1 mM to 100 mM, particularly from 2 mM to 75 mM, more particularly from 5 mM to 50 mM, even more particularly from 10 mM to 25 mM, most particularly of 16±2 mM. More particularly, the pH is in the range from 6.0 to 8.5, particularly from 6.5 to 8.0, more particularly from 6.75 to 8.0, and most particularly is 7.5±0.3. In another particular embodiment, the pharmaceutical composition further comprises a salt, particularly an inorganic salt, more particularly NaCl. More particularly, the salt is present in a concentration from 30 mM to 200 mM, particularly from 40 mM to 150 mM, more particularly from 50 mM to 100 mM, most particularly of 56±2 mM. The pharmaceutical composition may further comprise a tonicity modifying agent. Such tonicity modifying agents include, without limitation, glycerol, amino acids, sodium chloride, proteins, sugars and sugar alcohols, particularly the tonicity modifying agent is a sugar, more particularly the tonicity modifying agent is sucrose. In another embodiment, the tonicity modifying agent is present in a concentration of 50 mM to 200 mM, more particularly in a concentration of 100 mM to 175 mM, even more particularly is present in a concentration of 135 mM to 160 mM, and most particularly in a concentration of 150±2 mM. In another embodiment, the pharmaceutical composition further comprises a surfactant, particularly a non-ionic surfactant, wherein the surfactant or non-ionic surfactant is a polysorbate-based non-ionic surfactant, particularly polysorbate 20 or polysorbate 80, more particularly polysorbate 20. In a particular embodiment, the surfactant or non-ionic surfactant is present in a concentration of 0.01 mg/mL to 1 mg/mL, particularly in a concentration of 0.05 to 0.5 mg/mL and more particularly in a concentration of 0.2±0.02 mg/mL.

In an exemplary embodiment, the pharmaceutical composition comprises 0.1 mg/mL to 50 mg/mL of mutant FGF-21 peptide conjugate, 1 mM to 100 mM buffering agent, particularly Tris buffer, 30 mM to 200 mM salt, particularly NaCl, 50 mM to 200 mM tonicity modifying agent, particularly sucrose, and 0.01 mg/mL to 1 mg/mL surfactant or non-ionic surfactant, particularly polysorbate 20, and has a pH of 6.0 to 8.5.

In some embodiments, also encompassed herein is a pharmaceutical container comprising any one of or at least one of a mutant FGF-21 peptide conjugate described herein or a pharmaceutical composition comprising same. Exemplary such pharmaceutical containers include, without limitation, a syringe, vial, infusion bottle, ampoule, carpoule, a syringe equipped with a needle protection system, or a carpoule within an injection pen.

In some embodiments, a method of producing a mutant FGF-21 peptide conjugate described herein is presented, comprising the steps of:

(1) recombinantly producing the mutant FGF-21 peptide in an expression host; and (2) enzymatically attaching to the mutant FGF-21 peptide of step (1) a PEG-glycosyl moiety, wherein the PEG has 20 kDa, thereby forming the mutant FGF-21 peptide conjugate. In a particular embodiment, the expression host is *Escherichia coli*. In another particular embodiment of the method, step (2) comprises a step (2a) of contacting the mutant FGF-21 peptide with a GalNAc donor and a GalNAc transferase under conditions suitable to transfer GalNAc from the GalNAc donor to the threonine at amino acid position 173 of SEQ ID NO: 2. In a still more particular embodiment, the GalNAc donor is UDP-GalNAc. In yet another particular embodiment, the GalNAc transferase is MBP-GalNAcT2. In another particular embodiment of the method, step (2) further comprises a step (2b) of contacting the product of step (1) or of step (2a), if present, with a 20 kDa PEG-Sia donor and a sialyltransferase under conditions suitable to transfer 20 kDa PEG-Sia from the 20 kDa PEG-Sia donor to the threonine residue at amino acid position 173 of SEQ ID NO: 2 or to the GalNAc attached to the threonine residue at amino acid position 173 of SEQ ID NO: 2 if step (2a) is present. In a further particular embodiment of the method, the 20 kDa PEG-Sia donor is 20 kDa PEG-Sia-CMP. In a still more particular embodiment of the method, the sialyltransferase is ST6GalNAc1. In an even more particular embodiment of the method, the 20 kDa PEG-Sia donor comprises the structure

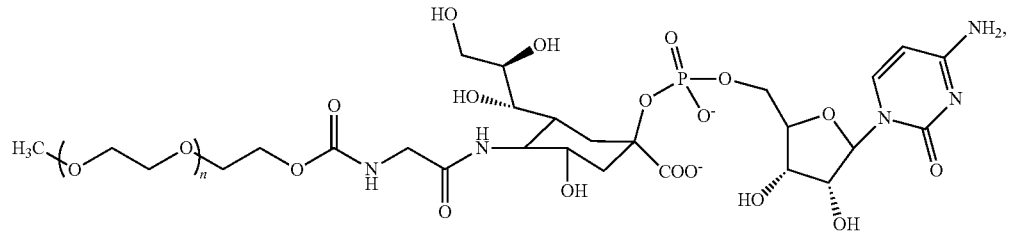

wherein n is an integer selected from 450 to 460.

In another particular embodiment of the method, the method further comprises a step (3), after step (1) and prior to step (2), of purifying the mutant FGF-21 peptide after recombinant production. The method may further comprise a step (4), after step (2), of purifying the mutant FGF-21 peptide conjugate formed in step (2). In a particular embodiment, step (3) comprises subjecting the mutant FGF-21 peptide and/or step (4) comprises subjecting the mutant FGF-21 peptide conjugate to a method selected from the group consisting of ion exchange chromatography, affinity chromatography, filtration and combinations thereof. The step of purifying may comprise one or more steps of ion exchange chromatography, particularly two steps of ion exchange chromatography. In a particular embodiment thereof, the ion exchange chromatography is an anion exchange chromatography, particularly a strong anion exchange chromatography. In a particular embodiment thereof, the anion exchange chromatography employs a member selected from the group consisting of a hydrophilic polyvinyl ether base matrix, polystyrene/divinyl benzene polymer matrix, trimethylammoniumethyl (TEAE), diethylaminoethanol (DEAE), agarose, a quaternary ammonium (Q) strong anion exchange chromatography and combinations thereof. In another particular embodiment thereof, step (3) comprises two anion exchange chromatography steps using a hydrophilic polyvinyl ether base matrix. In another particular embodiment thereof, step (4) comprises two quaternary ammonium (Q) strong anion exchange chromatography steps. In particular embodiment, arginine is added in step (2) and/or, if present, in step (3), particularly at least 400 mM arginine. In another particular embodiment, the method further comprises a step (5), after step (3) and prior to step (2), of endotoxin removal, wherein the product of step (3) is filtered using an endotoxin removal filter.

In some embodiments, also encompassed herein is a mutant FGF-21 peptide conjugate obtainable by any one of the methods described herein.

Method of Treatment

In some embodiments, methods for treating (e.g., controlling, relieving, ameliorating, alleviating, or slowing the progression of) or methods for preventing (e.g., delaying the onset of or reducing the risk of developing) diabetes and related diseases, particularly diabetes type 2, NAFLD, non-alcoholic steatohepatitis (NASH) and/or metabolic syndrome in a subject in need thereof are disclosed.

In some embodiments, a method for treating diabetes and related diseases, particularly diabetes type 2, NAFLD, non-alcoholic steatohepatitis (NASH) and/or metabolic syndrome is presented, the method comprising administering to a subject in need thereof a therapeutically effective amount of a mutant FGF-21 peptide conjugate described herein or a pharmaceutical composition comprising at least one of the mutant FGF-21 peptide conjugates described herein. In a particular embodiment, the subject in need thereof is a human subject.

In some embodiments, the step of administering comprises administering an effective dose of the composition that results in in at least one of the following: reduction of at the level of markers of NASH (e.g. serum markers), reduction of symptoms associated with NASH.

In some embodiments, a method for treating diabetes or a diabetes related disease is disclosed, comprising administering to a subject in need thereof an amount of a mutant FGF-21 peptide conjugate described herein or obtainable by a method described herein or a pharmaceutical composition comprising same. The diabetes or the diabetes related disease may comprise at least one of diabetes type 2, NAFLD, NASH, or metabolic syndrome. In some embodiments, a method for treating NASH is disclosed, comprising administering to a subject in need thereof an amount of a mutant FGF-21 peptide conjugate described herein or obtainable by a method described herein or a pharmaceutical composition comprising same. In some embodiments, a method for treating NAFLD is disclosed, comprising administering to a subject in need thereof an amount of a mutant FGF-21 peptide conjugate described herein or obtainable by a method described herein or a pharmaceutical composition comprising same. In some embodiments, a method for preventing the progression of NASH is disclosed, comprising administering to a subject in need thereof an amount of a mutant FGF-21 peptide conjugate described herein or obtainable by a method described herein or a pharmaceutical composition comprising same. In some embodiments, a method for preventing the progression of NAFLD is disclosed, comprising administering to a subject in need thereof an amount of a mutant FGF-21 peptide conjugate described herein or obtainable by a method described herein or a pharmaceutical composition comprising same. In a particular embodiment, the subject is a human subject. In a more particular embodiment, the administering reduces HbA1C levels, wherein reducing HbA1C levels is indicative of a durable reduction in blood glucose levels over time. A variety of exemplary indicators are known in the art and described herein including, without limitation, a reduction in glucose, insulin, body weight, serum lipids (total cholesterol, LDL, Triglycerides), liver enzymes (ALT, AST), liver weight, relative liver weight (% body weight), NAFLD Activity Score (NAS), fibrosis score (e.g., liver fibrosis), pro-inflammatory cytokines (e.g., IL1β, MCP-1), fibrosis biomarkers (αSMA, Collagen 1 alpha), hepatic cholesterol, hepatic triglycerides, and hepatic fatty acids. Increases in at least one of high molecular weight (HMW) adiponectin or HDL are also indicators of clinical efficacy of compounds and compositions described herein. In some embodiments, the method of treatment of the method for preventing the progression of the disease is assessed by Magnetic resonance imaging—Proton density fat fraction to determine the liver size (e.g. reduction of liver size).

In some embodiments, the biomarkers used to determine the efficacy of the treatment include one or more of the following:
Triglycerides
Non-high density lipoprotein (Non-HDL) cholesterol
High density lipoprotein (HDL-c)
Low density lipoprotein (LDL-c)
Hemoglobin A1c (HbA1c)
Homeostatic Model Assessment for Insulin Resistance (HOMA-IR)
Liver function tests: alanine transaminase (ALT), aspartate transaminase (AST) Adiponectin
N-Terminal Propeptide of Type III Collagen (Pro-C3)
Free fatty acids and Adipo-IR (fasting free fatty acids x fasting insulin)
inflammation marker high-sensitivity C-reactive protein (hs-CRP)
Total cholesterol
OGTT including C-peptide, glucose, and insulin
IGF-1, total
CK-18
Enhanced LiverFibrosis (ELF) panel.

In some embodiments, encompassed herein is any one of the mutant FGF-21 peptide conjugates described herein or a pharmaceutical composition comprising same for use in a method for treating diabetes or a diabetes related disease. The diabetes or the diabetes related disease may comprise at least one of diabetes type 2, NAFLD, NASH, or metabolic syndrome. In a particular embodiment, the diabetes or the diabetes related disease afflicts a human subject. In a more particular embodiment, the use reduces HbA1C levels, wherein reducing HbA1C levels is indicative of a durable reduction in blood glucose levels over time. A variety of exemplary indicators are known in the art and described herein including, without limitation, a reduction in glucose, insulin, body weight, serum lipids (total cholesterol, LDL, Triglycerides), liver enzymes (ALT, AST), liver weight, relative liver weight (% body weight), NAFLD Activity Score (NAS), fibrosis score (e.g., liver fibrosis), pro-inflammatory cytokines (e.g., IL1β, MCP-1), fibrosis biomarkers (αSMA, Collagen 1 alpha), hepatic cholesterol, hepatic triglycerides, and hepatic fatty acids. Increases in at least one of high molecular weight (HMW) adiponectin or HDL are also indicators of clinical efficacy of compounds and compositions described herein.

In some embodiments, use of a mutant FGF-21 peptide conjugate described herein in the preparation of a medicament for use in a method for treating diabetes or a diabetes related disease is presented. The diabetes or the diabetes related disease may comprise at least one of diabetes type 2, NAFLD, NASH, or metabolic syndrome. In a particular embodiment, the diabetes or the diabetes related disease afflicts a human subject. In a more particular embodiment, the use reduces HbA1C levels, wherein reducing HbA1C levels is indicative of a durable reduction in blood glucose levels over time. A variety of exemplary indicators are known in the art and described herein including, without limitation, a reduction in glucose, insulin, body weight, serum lipids (total cholesterol, LDL, Triglycerides), liver enzymes (ALT, AST), liver weight, relative liver weight (% body weight), NAFLD Activity Score (NAS), fibrosis score (e.g., liver fibrosis), pro-inflammatory cytokines (e.g., IL1β, MCP-1), fibrosis biomarkers (uSMA, Collagen 1 alpha), hepatic cholesterol, hepatic triglycerides, and hepatic fatty acids. Increases in at least one of high molecular weight (HMW) adiponectin or HDL are also indicators of clinical efficacy of compounds and compositions described herein.

In some embodiments, a mutant Fibroblast Growth Factor-21 (FGF-21) peptide conjugate is presented comprising
  i) a mutant FGF-21 peptide comprising the amino acid sequence of SEQ ID NO: 2,
  ii) a glycosyl moiety, wherein the glycosyl moiety comprises the structure -GalNAc-Sia-, and
  iii) a 30 kDa polyethylene glycol (PEG),
wherein the mutant FGF-21 peptide is attached to the glycosyl moiety by a covalent bond between a threonine at amino acid position 173 of SEQ ID NO: 2 and a first site of the glycosyl moiety and wherein the glycosyl moiety is attached to the 30 kDa PEG by a covalent bond between a second site of the glycosyl moiety and the 30 kDa PEG. In a particular embodiment, the 30 kDa PEG moiety is attached to the glycosyl moiety by a covalent bond to a linker, wherein the linker comprises at least one amino acid residue. Exemplary amino acids, include: polar, but neutral amino acids (e.g., serine, threonine, cysteine, tyrosine, asparagine, and glutamine) and non-polar amino acids with relatively simple side chains (e.g. glycine, alanine, valine, leucine). In a particular embodiment, the at least one amino acid residue is at least one glycine (Gly). In a still more particular embodiment, the mutant FGF-21 peptide conjugate comprises the structure -GalNAc-Sia-Gly-PEG (30 kDa). A mutant FGF-21 peptide conjugate described herein may comprise a 30 kDa PEG which is a linear or branched PEG. In a more particular embodiment, the 30 kDa PEG is a linear PEG. In a still more particular embodiment, the 30 kDa PEG is a 30 kDa methoxy-PEG. In some embodiments, single or multiple administrations of the compositions can be carried out with dose levels and pattern being selected by the treating physician. In any event, the pharmaceutical compositions should provide a quantity of the mutant FGF-21 peptide conjugate of this invention sufficient for an effective treatment of the subject in need of such treatment.

In the pharmaceutical composition, in some embodiments, the mutant FGF-21 peptide conjugate is present in a concentration in the range from 0.1 mg/mL to 50 mg/mL, particularly from 1 mg/mL to 45 mg/mL, more particularly from 10 mg/mL to 40 mg/mL, most particularly in a concentration of 26±4 mg/mL. In a more particular embodiment, the concentration of the mutant FGF-21 peptide conjugate in a pharmaceutical composition is 33±7 mg/mL or even more particularly 26±4 mg/mL.

All components of the pharmaceutical composition as well as the specific concentrations of the components have carefully selected after testing very many different conditions, compounds and concentrations thereof. Hence, the pharmaceutical composition disclosed herein is not an arbitrary selection of compounds and compound concentrations but a specific and rational selection of conditions which have been found to be most optimal for an aqueous pharmaceutical composition containing the mutant FGF-21 peptide conjugate or mutant FGF-21 peptide according to the invention for use as a medicament.

In some embodiments, the pharmaceutical composition particularly comprises a buffering agent, particularly a phosphate or Tris buffer, more particularly a Tris buffer, e.g. Tris(hydroxymethyl)aminomethane (THAM). Optionally, the buffering agent is present in a concentration from 1 mM to 100 mM, particularly from 2 mM to 75 mM, more particularly from 5 mM to 50 mM, even more particularly from 10 mM to 25 mM, most particularly of 16±2 mM. Tris buffer was selected since solubility of the protein was found to be better than for other buffer systems and it is suitable to keep the pH at pH 7.5. This pH seems the most optimal one for prolonged storage of the PEGylated mutant FGF-21 peptide conjugate. Moreover, probability of Tris crystallization at lower temperatures is lower than that of phosphate based buffering agents.

In some embodiments, the mutant FGF-21 peptide conjugate may undergo precipitation of the pH is below 6.0. Optionally, the pH of the pharmaceutical composition is in the range from 6.0 to 8.5, particularly from 6.5 to 8.0, more particularly from 6.75 to 8.0, even more particularly from 7.0 to 8.0, and most particularly is 7.5±0.3 as lowest fragmentation in SDS-PAGE and least aggregation in SEC was observed if the pH is in the range of 7-8. This pH has also been identified to be optional with respect to viscosity. As the pH of a solution may depend on the temperature of the solution, the pH should particularly be adapted and measured at 25±2° C. The pH is adjusted with HCl. The pharmaceutical composition may further comprise a salt, particularly an inorganic salt, more particularly NaCl. Optionally, the salt is present in a concentration from 30 mM to 200 mM, particularly from 40 mM to 150 mM, more particularly from 50 mM to 100 mM, most particularly of 56±2 mM. The presence of a salt, particularly NaCl, is beneficial to reduce viscosity which is increased in PEG containing samples. For the same reason, it is also beneficial to include sorbitol and/or glycine.

In some embodiments, the pharmaceutical composition may further comprise a tonicity modifying agent. The tonicity modifying agent may be selected from the group consisting of glycerol, amino acids, sodium chloride, proteins, sugars and sugar alcohols. In a particular embodiment, the tonicity modifying agent is a sugar, more particularly the tonicity modifying agent is sucrose. A tonicity modifying agent, in particular sucrose, was found to have an advantageous effect on the pharmaceutical composition as it reduces aggregation of the active agent, namely the mutant FGF-21 peptide (conjugate). The tonicity modifying agent, particularly sucrose, may be present in a concentration of 50 mM to 200 mM, more particularly in a concentration of 100 mM to 175 mM, even more particularly in a concentration of 135 mM to 160 mM, and most particularly in a concentration of 150±2 mM.

Further, the pharmaceutical composition, in some embodiments, may comprise a surfactant, particularly a non-ionic surfactant. The surfactant or non-ionic surfactant particularly is a polysorbate-based non-ionic surfactant, more particularly polysorbate 20 or polysorbate 80, and even more particularly polysorbate 20. A surfactant, in particular polysorbate 20, was found to reduce sub-visible particles below 10 μm and thus seems to have a stabilizing effect on the pharmaceutical composition.

The surfactant or non-ionic surfactant, particularly polysorbate 20 or 80, more particularly polysorbate 20, is optionally present in a concentration of 0.01 mg/mL to 1 mg/mL, particularly in a concentration of 0.05 to 0.5 mg/mL and most particularly in a concentration of 0.2±0.02 mg/mL. Polysorbate 20 or 80, particularly polysorbate 20, were found to stabilize the formulation to aggregation.

In a particular embodiment, a pharmaceutical composition comprises 0.1 to 50 mg/mL, particularly 33±7 mg/mL of mutant FGF-21 peptide conjugate; 1 mM to 100 mM, particularly 20±2 mM, buffering agent, particularly a Tris buffer; 30 mM to 200 mM, particularly 70±2 mM, salt, particularly NaCl; and has a pH of 7.5±0.3 (particularly measured at 25±2° C.

A more particular pharmaceutical composition comprises 0.1 to 50 mg/mL, particularly 26±4 mg/mL of mutant FGF-21 peptide conjugate; 1 mM to 100 mM, particularly 16±2 mM, buffering agent, particularly a Tris buffer; 30 mM to 200 mM, particularly 56±2 mM, salt, particularly NaCl; 50 mM-200 mM tonicity modifying agent, particularly sucrose; and 0.01 to 1 mg/mL, particularly 0.2±0.02 mg/mL, surfactant or non-ionic surfactant, particularly polysorbate 20; and has a pH of 7.5±0.3 (particularly measured at 25±2° C.

In some embodiments, a pharmaceutical container comprising the mutant FGF-21 peptide conjugate of the invention and as described herein or the pharmaceutical composition of the invention and as described herein. In a particular embodiment, the pharmaceutical container is a syringe, vial, infusion bottle, ampoule, carpoule, a syringe equipped with a needle protection system, or a carpoule within an injection pen. In some embodiments, the present invention further provides a method of producing the mutant FGF-21 peptide conjugate of the invention, comprising the steps of:

(1) recombinantly producing the mutant FGF-21 peptide, particularly in an expression host; and
(2) enzymatically attaching to the mutant FGF-21 peptide of step (1) a PEG-glycosyl moiety, wherein the PEG is, for example, a 20 kDa PEG or a 30 kDa PEG, and wherein step (2) is particularly a cell free, in vitro process, thereby forming the mutant FGF-21 peptide conjugate.

In a particular embodiment, the method is as follows: First the mutation which introduces the threonine adjacent to and on the C-terminal side of a proline residue and optionally one or more further mutations are introduced into a nucleic acid sequence encoding for native or mutated FGF-21, such as of human FGF-21 as in SEQ ID NO: 1. The nucleic acid sequence encoding the mutated FGF-21 peptide is the introduced into an expression vector suitable for protein expression in an expression host. Methods for introducing mutations into nucleic acid sequences, such as site-directed mutagenesis, and the incorporation of the mutated nucleic acid sequence into an expression vector are well known to the skilled person (cf. e.g., "A Guide to Methods in the Biomedical Sciences" by R. B. Corley, Springer Science & Business Media, 2006).

After protein expression, optional purification, the PEG residue is attached to the mutant FGF-21 peptide, specifically at the newly introduced threonine residue via at least one glycosyl moiety and optionally via at least one amino acid residue which is present between the PEG and the glycosyl residue.

To obtain high yield expression of a nucleic acid encoding a mutant FGF-21 of the present invention, one typically subclones a polynucleotide encoding the mutant Fibroblast Growth Factor into an expression vector that contains a strong promoter to direct transcription, a transcription/translation terminator and a ribosome binding site for translational initiation. Suitable bacterial promoters are described, e.g., in Sambrook and Russell, supra, and Ausubel et al, supra. Bacterial expression systems for expressing the native or mutant FGF-21 are available in, e.g., *Escherichia coli* (*E. coli*), *Bacillus* sp., *Salmonella*, and *Caulobacter*. Kits for such expression systems are commercially available. Eukaryotic expression systems for mammalian cells, yeast, and insect cells are commercially available. In one embodiment, the eukaryotic expression vector is an adenoviral vector, an adeno-associated vector, or a retroviral vector. In a particular embodiment, the mutant FGF-21 peptide is recombinantly produced in *E. coli* cells, i.e. the expression host is *E. coli*.

An exemplary method of production is described in this paragraph: The mutant FGF-21 peptide is expressed in *E. coli* as inclusion bodies. Cells are recovered from the harvest by centrifugation, disrupted, and inclusion bodies are washed and recovered by centrifugation. Purification of the non-PEGylated mutant FGF-21 peptide begins with solubilizing the mutant FGF-21 peptide from the inclusion bodies and refolding of the peptide. The refolded mutant FGF-21 peptide is filtered and purified by two anion exchange chromatography operations, both utilizing Eshmuno Q chromatography resin and operated in bind and elute mode. If necessary, the purified mutant FGF-21 peptide may be concentrated by ultrafiltration using Pellicon 2 (5 kD MWCO) membranes. The purified mutant FGF-21 peptide is dispensed into sterile PETG bottles and may be stored at ≤70° C.

GlycoPEGylation of mutant FGF-21 peptide may be performed by two enzymatic reactions performed in series or at the same time. This step may be followed by 0.2 μm filtration and two anion exchange chromatography operations, both utilizing Q Sepharose Fast Flow chromatography resin and operated in bind and elute mode. A final concentration step may be performed by ultrafiltration using Pellicon XL Biomax (10 kDa MWCO).

Two principal classes of enzymes are used in the synthesis of carbohydrates, glycosyltransferases (e.g., sialyltransferases, oligosaccharyltransferases, N-acetylglucosaminyltransferases), and glycosidases. The glycosidases are further classified as exoglycosidases (e.g., β-mannosidase, β-glucosidase), and endoglycosidases (e.g., Endo-A, Endo-M). Each of these classes of enzymes has been successfully used synthetically to prepare carbohydrates. For a general review, see, Crout et al., Curr. Opin. Chem. Biol. 2: 98-111 (1998). See also PCT Publication Nos: WO 2003/031464; WO 2005/089102; WO 2006/050247; and WO 2012/016984, the entire content of each of which is incorporated herein by reference.

In a particular embodiment, step (2) comprises a step (2a) of contacting the mutant FGF-21 peptide with a GalNAc donor and a GalNAc transferase under conditions suitable to transfer GalNAc from the GalNAc donor to the at least one threonine residue of the mutant FGF-21 peptide. Conditions for this transfer are described herein. Optionally, the GalNAc donor is UDP-GalNAc and, particularly, the GalNAc transferase is MBP-GalNAcT2.

In a particular embodiment and more particularly in combination with the embodiment of the aforementioned paragraph, step (2) further comprises, particularly in combination with step (2a), a step (2b) of contacting the product of step (2a), if present, or of step (1), with, e.g., a 20 kDa PEG-Sia donor or 30 kDa PEG-Sia donor and a sialyltransferase under conditions suitable to transfer 20 kDa PEG-Sia from the 20 kDa PEG-Sia donor or the 30 kDa PEG-Sia from the 30 kDa PEG-Sia donor to the at least one threonine residue of the mutant FGF-21 peptide, if step (2a) is not present, or to the GalNAc at the mutant FGF-21 peptide, if step (2a) is present. Optionally, the 20 kDa PEG-Sia donor is 20 kDa PEG-Sia-CMP or the 30 kDa PEG-Sia donor is 30 kDa PEG-Sia-CMP and/or the sialyltransferase is ST6GalNAc1. As already explained in general above, the term "20 kDa PEG-Sia" also includes "20 kDa PEG-linker-Sia" and "20 kDa PEG-Gly-Sia" and the term "30 kDa PEG-Sia" also includes "30 kDa PEG-linker-Sia" and "30 kDa PEG-Gly-Sia".

In a more particular embodiment, the 20 kDa PEG-Sia donor comprises the structure

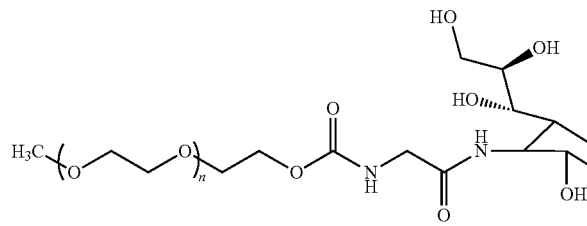
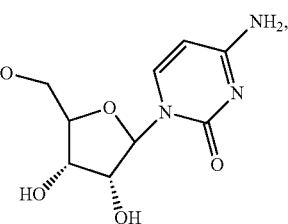

wherein n is an integer selected from 450 to 460, which results in a molecular weight of 20 kDa. This structure includes a Gly linker. The skilled person understands that methods for producing the same are described in PCT Publication No. WO 2003/031464, the entire content of which is incorporated herein by reference.

In some embodiments, After expression and before the glycoPEGylation reaction the mutant FGF-21 peptide may be purified. Hence, optionally, the method further comprises a step (3), after step (1) and prior to step (2), of purifying the mutant FGF-21 peptide after recombinant production. Further, the method may comprise a step (4), after step (2), of purifying the mutant FGF-21 peptide conjugate formed in step (2). In some embodiments, the purification step (3) and/or (4) may comprise subjecting the mutant FGF-21 peptide to a method selected from the group consisting of ion exchange chromatography, affinity chromatography, filtration and combinations thereof. Step (3) and/or step (4) may comprise one or more steps of ion exchange chromatography, affinity chromatography, filtration or combinations thereof.

Step (3) and/or step (4) may particularly comprise subjecting the mutant FGF-21 peptide to one or more steps of ion exchange chromatography, more particularly to at least two steps of ion exchange chromatography, even more particularly anion exchange chromatography. In a more particular embodiment, the mutant FGF-21 peptide is subjected to two anion exchange chromatography steps, more particularly to two strong anion exchange chromatography steps in step (3) and in step (4).

The anion exchange chromatography particularly employs a member selected from the group consisting of a hydrophilic polyvinyl ether base matrix, diethylaminoethanol (DEAE), trimethylammoniumethyl (TEAE), agarose, polystyrene/divinyl benzene polymer matrix, a quaternary ammonium (Q) strong anion exchange chromatography and combinations thereof, even more particularly in step (3) two columns using a hydrophilic polyvinyl ether base matrix are used, highly particularly in step (3) two Eshmuno©-Q columns are used. Eshmuno©-Q resins having ahydrophilic polyvinyl ether base matrix are e.g. available from Merck Millipore, Merck KGaA, Darmstadt, Germany. Source 15Q resins are also of use in the present invention (GE Health Care Life Sciences, Chalfont St Giles, UK). The affinity chromatography may be an anionic anthraquinone dye affinity chromatography and filtration may employ a modified hydrophilic polyethersulfone (PES) membrane. In another embodiment, two weak anion exchange chromatography steps are performed or one strong and one weak anion exchange chromatography step.

In an alternative embodiment, the purification in step (3) is performed as below, optionally in the given order:
1. ion exchange chromatography, particularly anion exchange chromatography,
2. optionally affinity chromatography,
3. optionally ion exchange chromatography, particularly anion exchange chromatography, and 3. filtration.

Exemplary purification is performed in the Example section. In general, the chromatography purification steps are to be performed according to the manufacturer's protocols. Further information can e.g. be taken from "Protein Purification Protocols", Paul Cutler, Springer Science & Business Media, 2004).

In an optional embodiment, the method further comprises a step (4), after step (2), of purifying the mutant FGF-21 peptide conjugate formed in step (2), particularly by ion exchange chromatography, more particularly by strong anion exchange chromatography, even more particularly by quaternary ammonium (Q) strong anion exchange chromatography. In a particular embodiment, two anion exchange chromatography steps are performed in step (4). Q-sepharose is a more particular column material suitable for purifying the mutant FGF-21 peptide conjugate of the present invention in step (4). Q sepharose is e.g. available from GE Healthcare Life Sciences, Chicago, Ill., USA.

In a particular embodiment, arginine is added in steps (2) and (3), particularly at least 400 mM arginine. Arginine is optionally added to inhibit proteases which would otherwise degrade the protein. Hence, arginine helps to prevent protein loss. Finally, endotoxin is removed which may originate from the expression host in an optional step (5), after step (3) and prior to step (2). In this step, the product of step (3) is filtered using an endotoxin removal filter, such as Mustang E, 0.2 micron filter. Further, the mutant FGF-21 peptide conjugate may be sterile filtered.

In some embodiments, provided are the mutant FGF-21 peptide conjugates obtainable by the method described herein.

In some embodiments, the present invention also provides the mutant FGF-21 peptide conjugate of the invention and/or the pharmaceutical composition of the invention for use as a medicament and for use in the treatment of diabetes and related diseases, particularly diabetes type 2, nonalcoholic fatty liver disease (NAFLD), non-alcoholic steatohepatitis (NASH) and/or metabolic syndrome. For example, some embodiments also provide the use of the mutant FGF-21 peptide conjugate of the invention and/or the use of the pharmaceutical composition of the invention for the treatment of diabetes and related diseases, particularly diabetes type 2, NAFLD, NASH and/or metabolic syndrome.

In some embodiments is provided a method of treating diabetes and related diseases, particularly diabetes type 2, NASH, nonalcoholic fatty liver disease (NAFLD), and/or metabolic syndrome comprising administering to a subject in need thereof an amount of the mutant FGF-21 peptide conjugate according to the invention or the pharmaceutical composition according to the invention. In a particular embodiment, the subject is a human subject.

NASH is a chronic liver disease, characterized histologically by hepatic steatosis in ≥5% of hepatocytes, injury (ballooning). It is part of the spectrum of NAFLD that includes NASH, and cirrhosis resultant from fatty liver. NAFLD is a common chronic liver disease in Western countries, which can progress to cirrhosis and is associated with an increased mortality risk in general and an increased cardiovascular disease mortality risk in particular. In North America, the prevalence of NAFLD is estimated at ~24%. NAFLD patients tend to be obese, with insulin resistance and/or type 2 diabetes mellitus (T2DM), dyslipidemia, hypertriglyceridemia, and hypertension, and NAFLD is increasingly recognized as the liver disease component of the metabolic syndrome (MetS) (Chalasani, 2018).

NAFLD is usually asymptomatic, unless progression to cirrhosis has occurred. It is often diagnosed by demonstration of hepatic steatosis on liver imaging (e.g., ultrasound or magnetic resonance imaging (MRI)) in subjects, commonly with features of the metabolic syndrome, in whom no alternative etiology for liver fat accumulation can be identified (e.g., alcoholic liver disease, medications). Validated noninvasive tests for diagnosis of steatohepatitis are not currently available, and a liver biopsy is still needed to diagnose the inflammation and cellular ballooning features of NASH (Torres, 2012).

Current pharmacological treatment of NAFLD has limited efficacy and therefore, there is a pressing need to develop more effective and safe agents for this common and life-threatening disease. Obeticholic acid (OCA), a selective agonist of the farnesoid X receptors, appears to have promise as a therapeutic agent for the management of NAFLD. The Farnesoid X Receptor Ligand Obeticholic Acid in NASH Treatment (FLINT) trial in patients with NASH, revealed that OCA administration is associated with improvements in liver histology, as well as weight loss and reduction in blood pressure. Although its adverse effects on lipid profile and insulin sensitivity are noteworthy, OCA might be considered in selected patients with NAFLD/NASH, particularly those with adequately controlled glucose and lipid levels.

With respect to indicators demonstrating clinical efficacy of compounds and compositions described herein, a variety of exemplary indicators are known in the art and described herein including, without limitation, a reduction in HbA1c, glucose and Insulin, body weight, serum lipids (total cholesterol, LDL, Triglycerides), liver enzymes (ALT, AST), liver weight, relative liver weight (% body weight), NAFLD Activity Score (NAS), fibrosis score (e.g., liver fibrosis), pro-inflammatory cytokines (e.g., IL10, MCP-1), fibrosis biomarkers (αSMA, Collagen 1 alpha), hepatic cholesterol, hepatic triglycerides, and hepatic fatty acids. Increases in at least one of high molecular weight (HMW) adiponectin or HDL are also indicators of clinical efficacy of compounds and compositions described herein. Accordingly, a change (as indicated above) in at least one of the indicators reflects clinical efficacy of a compound or composition described herein.

In a particular embodiment, the therapeutic efficacy of a compound or composition described herein is determined based on a reduction in at least one of serum triglyceride levels or serum insulin levels.

HOMA-IR is, for example, is an indicator of the presence and extent of insulin resistance in a subject. It is an accurate indicator of the dynamic between baseline (fasting) blood sugar and insulin levels responsive thereto. It is referred to as an insulin resistance calculator. For humans, a healthy range is 1.0 (0.5-1.4). Less than 1.0 indicates that a subject is insulin-sensitive, which is ideal; above 1.9 indicates that a subject is exhibiting early insulin resistance; above 2.9 indicates that a subject is exhibiting significant insulin resistance. HOMA-IR blood code calculation is determined as follows: insulin uIU/mL (mU/L) X glucose (mg/dL) =HOMA-IR. The calculation requires U.S. standard units. To convert from international SI units: for insulin: pmol/L to uIU/mL, divide (÷) by 6; for glucose: mmol/L to mg/dL, multiply (X) by 8.

Some embodiments relate to dosage regimen whereby an effective amount of a mutant FGF-21 peptide conjugate described herein or a pharmaceutical composition comprising a therapeutically effective amount of a mutant FGF-21 peptide conjugate is administered to the subject in need thereof. In some embodiments, from about 3 mg to about 27 mg of a mutant FGF-21 peptide conjugate described herein or a pharmaceutical composition comprising from about 3 mg to about 27 mg of a mutant FGF-21 peptide conjugate is administered to the subject in need thereof once a week. In some embodiments, the effective amount of mutant FGF-21 peptide conjugate can be in a range of about 3 mg to about 27 mg; a range of about 9 mg to about 27 mg; a range of about 18 ng to about 27 ng; a range of about 3 mg to about 9 mg; a range of about 9 mg to about 18 mg; a range of about 18 mg to about 27 mg; a range of 3 mg to 18 mg and is administered once a week. For example, the effective amount of mutant FGF-21 peptide conjugate can be about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, 2 about 6 mg, or about 27 mg.

In some embodiments, from about 18 mg to about 36 mg of a mutant FGF-21 peptide conjugate described herein or a pharmaceutical composition comprising from about 18 mg to about 36 mg of a mutant FGF-21 peptide conjugate is administered to the subject in need thereof once every two weeks. For example, the effective amount of mutant FGF-21 peptide conjugate can be about 18 mg, about 19 mg, about 20 mg, about 21 mg, about 22 mg, about 23 mg, about 24 mg, about 25 mg, 2 about 6 mg, about 27 mg, about 28 mg, about 29 mg, about 30 mg, about 31 mg, about 32 mg, about 33 mg, about 34 mg, about 35 mg, or about 36 mg.

In some embodiments, a therapeutically effective amount of a mutant FGF-21 peptide conjugate described herein or a pharmaceutical composition comprising a therapeutically effective amount of a mutant FGF-21 peptide conjugate is administered twice per day, once per day, every two days, three times per week, once per week, once every two weeks, once every three weeks, or once per month.

Long duration efficacy of mutant FGF-21 peptide conjugates described herein is evidenced by the surprisingly long half-life (between about 55 to about 100 hours) determined for these conjugates in animal model systems. Native FGF21 has a short life (~2 hours), limiting the potential to use it as a therapeutic agent. In humans, the effects of pegbelfermin (Pegylated FGF-21 having a half-life of 19-24 hours) showed a lower efficacy in the lipid measurements (% change vs. baseline) when dosed weekly vs daily.

Long duration efficacy of mutant FGF-21 peptide conjugates described herein, in turn, makes it possible to administer the mutant FGF-21 peptide conjugates less frequently, for example one a week or once every two weeks. Accordingly, in a particular embodiment, a mutant FGF-21 peptide conjugate described herein or a composition comprising same is administered to a subject in need thereof at a frequency of equal to or lower than once per week or once per 2 weeks. For example, the mutant FGF-21 peptide conjugate described herein or a composition comprising same may be administered to a subject in need thereof once every 7 days, once every 8 days, once every 9 days, once every 10 days, once every 11 days, once every 12 days, once every 13 days, once every 14 days, once every 15 days, once every 16 days, once every 17 days, once every 18 days, once every 19 days, once every 20 days, once every 21 days, once every 22 days, once every 22 days, once every 23 days, once every 24 days, once every 25 days, once every 26 days, once every 27 days, once every 28 days, once every 29 days, once every 30 days, or once every 31 days.

In an exemplary embodiment, the compounds described herein and compositions comprising same is administered to a subject in need thereof at a frequency of once a week. In an exemplary embodiment, the compounds described herein and compositions comprising same is administered to a subject in need thereof at a frequency of once every two weeks.

In another exemplary therapeutic regimen, compounds described herein and compositions comprising same are following a course of "induction" therapy, which calls for more frequent administration such as twice a week or weekly at the onset of the treatment regimen followed by maintenance therapy, which may involve weekly, once every two weeks or once a month administration. Such regimen is effective in that the initial induction therapy improves the subject's condition to a manageable level that is acceptable with regard to achieving a clinical state that is acceptable for maintenance of the disease/condition. Thereafter, the maintenance therapy is used to preserve the level of wellness at the maintenance level.

Therapeutic efficacy of a compound and/or composition for treating diabetes and related diseases, particularly diabetes type 2, nonalcoholic fatty liver disease (NAFLD), non-alcoholic steatohepatitis (NASH) and/or metabolic syndrome may be evaluated using a variety of parameters and assays known by persons of skill in the art and described herein (see Example 1 and Example 4). Measuring HbA1C is considered a standard assay for measuring glycemic index of a subject over a long duration. It is, therefore, a stable indicator of glycemic index, reflecting glucose levels over the course of approximately the last 3-4 months. Accordingly, a subject who has diabetes (e.g., diabetes type 2) may be defined by the percent HbA1C determined in a suitable assay. For a healthy person without diabetes, the normal range for the hemoglobin A1c level is between 4% and 5.6%. Hemoglobin A1c levels between 5.7% and 6.4% indicate that a person has a higher chance of developing diabetes. Levels of 6.5% or higher indicate that a person has diabetes.

In a particular embodiment, HbA1C is measured with HPLC by using the Glycated hemoglobin test system (BIO-RAD, Hercules, Calif., USA). Blood samples (e.g., 1.0 mL/per time) may be collected from the cephalic or saphenous vein into BD Vacutainer® K2-EDTA tubes. Samples may be stored immediately at 4 degrees C. or maintained on wet ice and analyzed on the same day the blood was collected. HbA1c levels in the blood may be measured by persons skilled in the art with HPLC by using the Glycated hemoglobin test system (BIO-RAD, Hercules, Calif., USA).

With regard to NASH, this condition is currently diagnosed only by biopsy. There are some surrogate biomarkers however, that are considered predictive of NASH, such as liver fat (determined by MRI), liver enzymes (ALT and ALT/AST ratio), and fibrosis biomarkers, such as pro-C3.

EXAMPLES

Example 1: Mutant FGF21-GalNAc-SA-PEG-20 kDa (BIO89-100) Single Ascending Dose Study in Humans Methods: In an embodiment, a total of 58 healthy subjects were treated with subcutaneous (SC) BIO89-100 (7 dose levels) or placebo, in a single-center study to assess safety, tolerability, PK, immunogenicity and exploratory pharmacodynanics. Subjects were randomized to receive a single dose of either BIO89-100 at 0.45 mg, 1.2 mg, 3 mg, 9.1 mg, 18.2 mg, 39 mg or 78 mg, or placebo at a 6:2 ratio (7:3 ratio for the 9.1 mg dose). Subjects were followed for 4 weeks with frequent assessments initially and then weekly from Day 8 through Day 29.

Figure 6A:
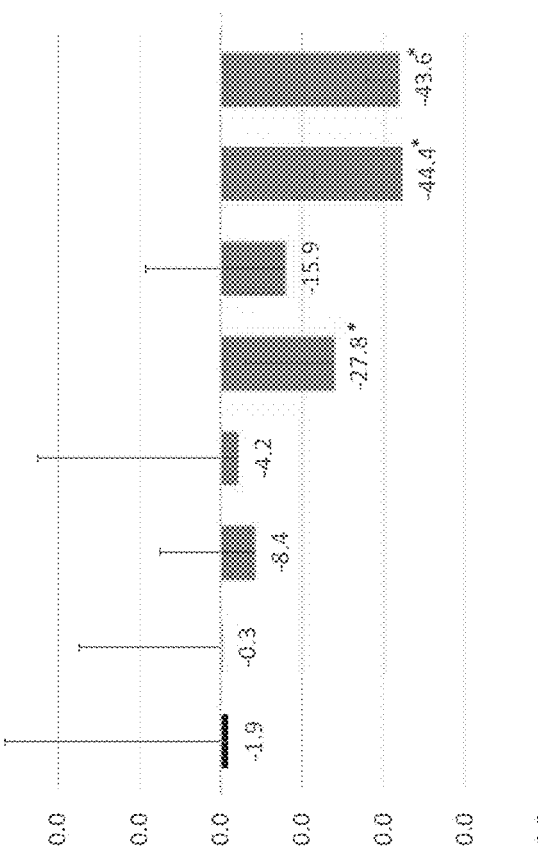
Figure 6B:
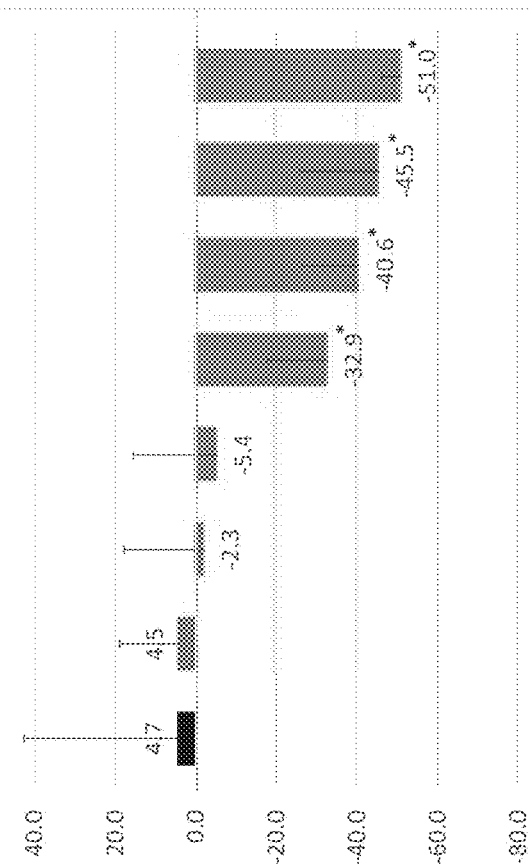
Figure 7:
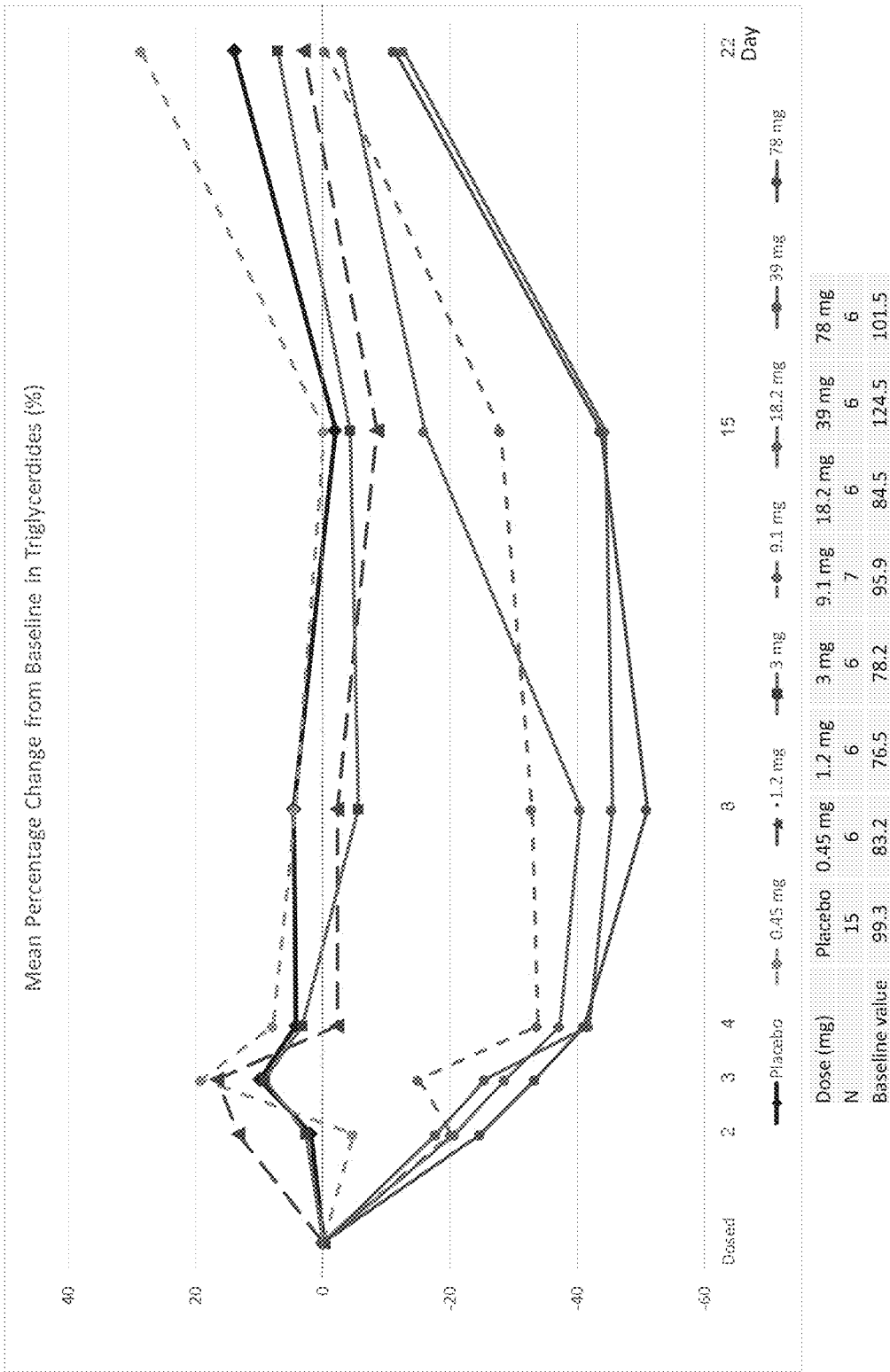
Figures 8A, 8B:
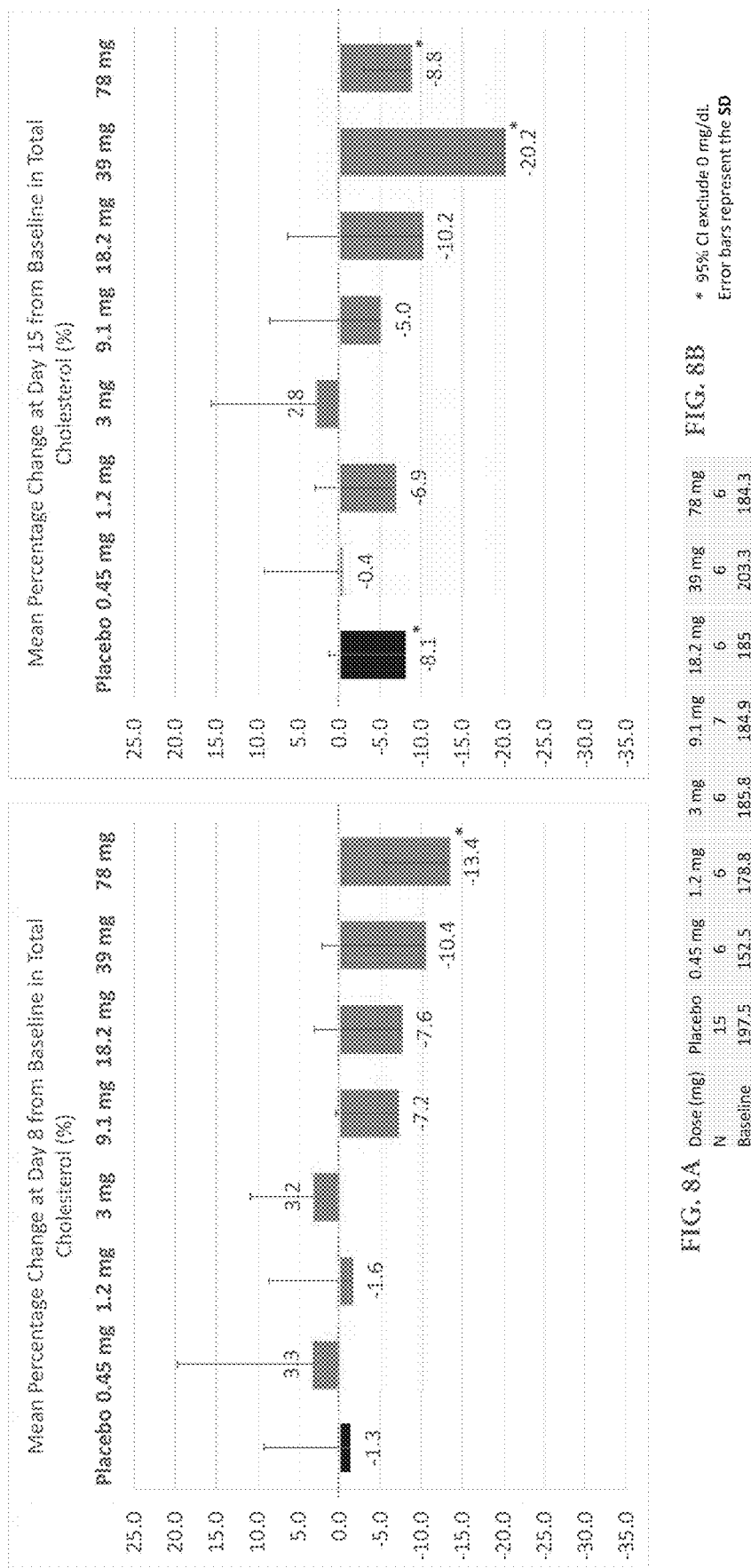
Figures 9A, 9B:
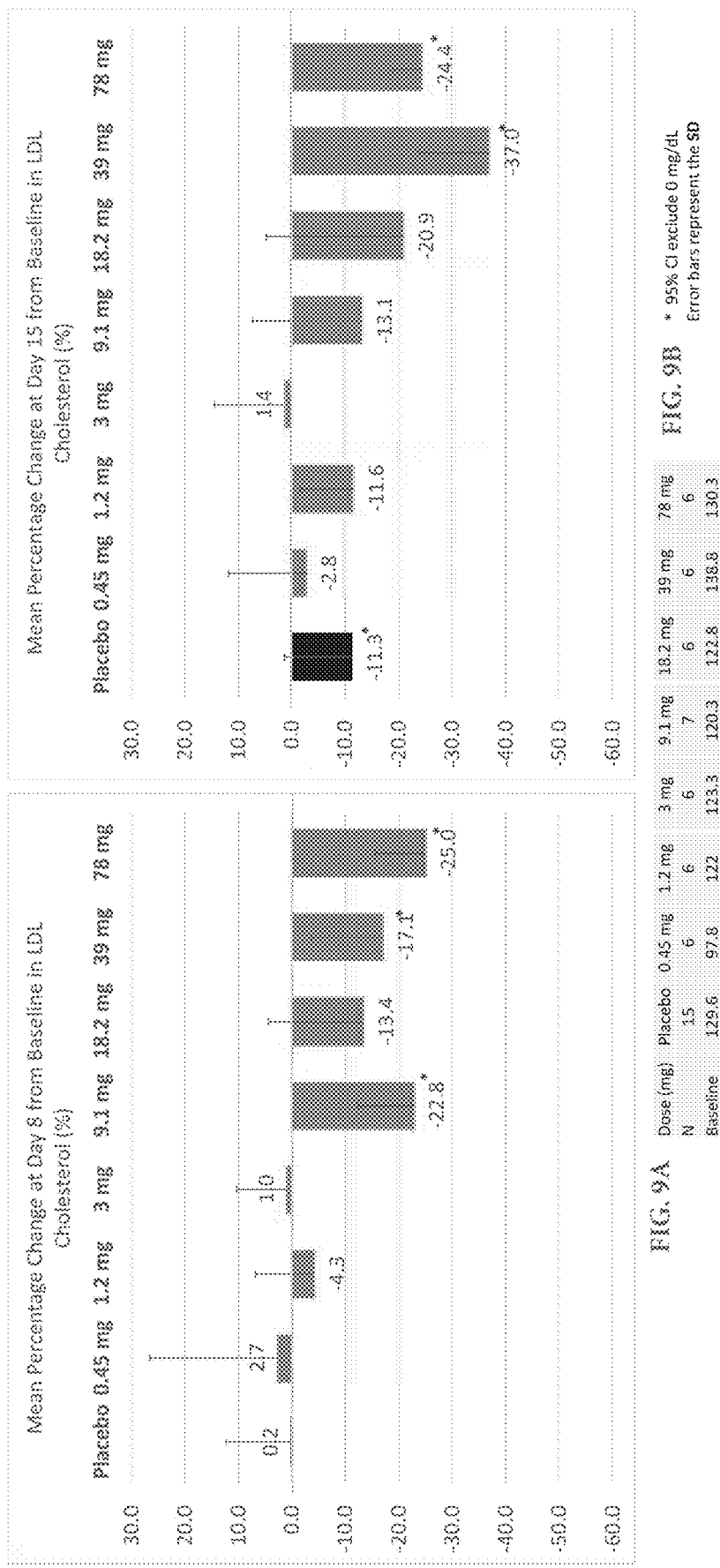
Figures 10A, 10B:
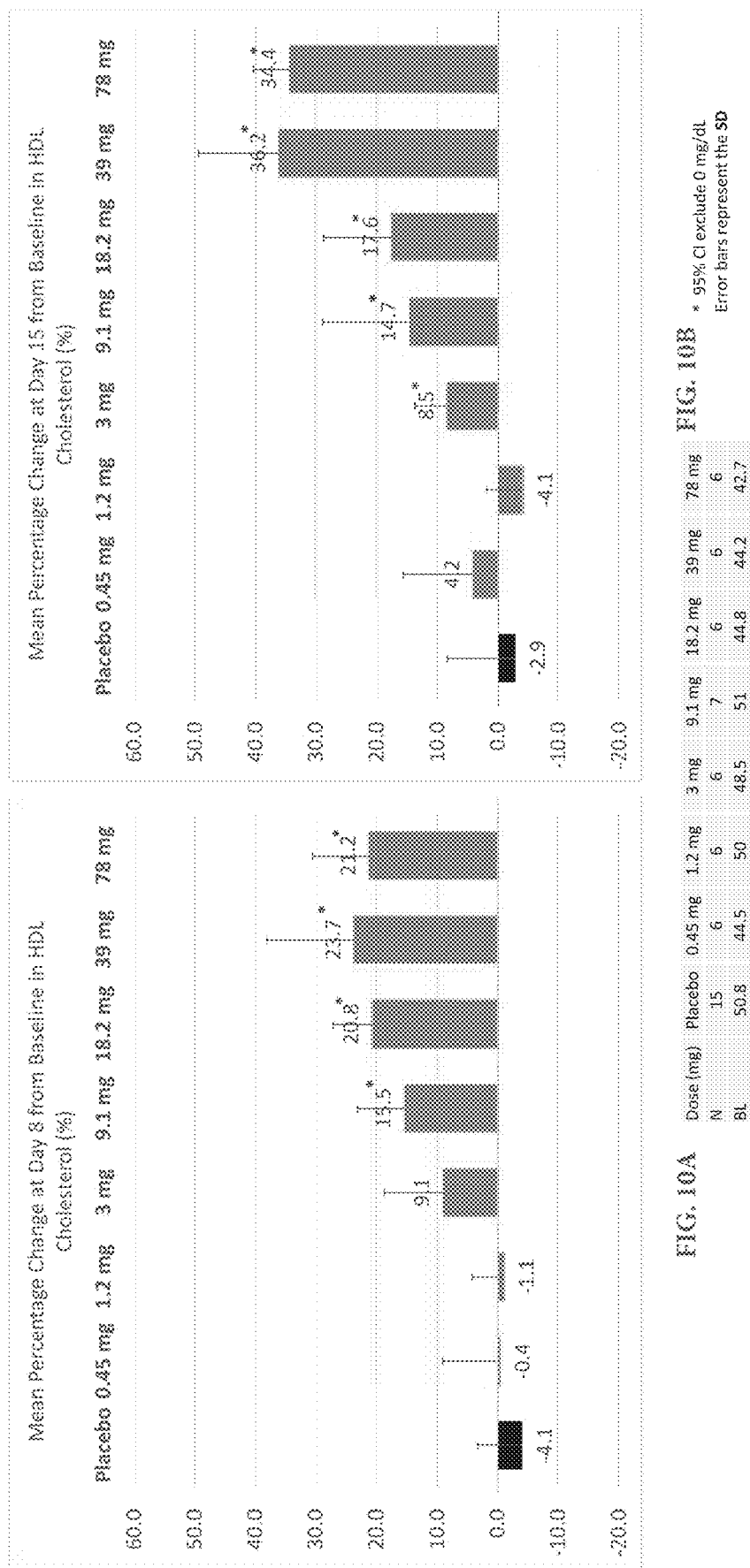

Results: FIGS. 1-14 present results from a single ascending dose (SAD) studies in humans of some embodiments of the present invention. Baseline demographics were similar between pooled BIO89-100 treated subjects (N=43) and pooled placebo (N=15), as were mean baseline laboratory parameters (within normal range). Mean age was 39.3 years, mean BMI was 26.7 kg/m$^2$, and 86% of subjects were male. There were no deaths, SAEs, discontinuations due to AEs or AE-related dose changes. Among subjects who received BIO89-100, the most common treatment-related adverse events, occurring in ≥2 subjects in the pooled BIO89-100 group, were injection site reactions and headache, all reported as mild. No clinically meaningful trends were observed in laboratory or other safety-related parameters. The PK of BIO89-100 was generally dose proportional, with an average elimination half-life ~53-100 hours. At single doses of 9.1 mg and higher, BIO89-100 demonstrated significant improvements versus baseline in key lipid parameters measured at 8 and 15 days following dosing. The mean changes versus baseline included reduction in triglycerides (up to 51%, Table 1), reduction in LDL-C (up to 37%), and increase in HDL-C (up to 36%).

TABLE 1

Serum triglycerides - Mean change from baseline (%) on Day 8 and Day 15

|  | Placebo N = 15 | 9.1 mg N = 7 | 18.2 mg N = 6 | 39 mg N = 6 | 78 mg N = 6 |
|---|---|---|---|---|---|
| Mean at Baseline (BL [SD]; mg/dL) | 99.3 (42.0) | 95.9 (33.4) | 84.5 (30.4) | 124.5 (45.8) | 101.5 (15.8) |
| % change from BL to Day 8 (SD) | 4.7 (38.0) | −32.9 (15.2) | −40.6 (14.2) | −45.5 (19.7) | −51.0 (4.9) |
| % change from BL to Day 15 (SD) | −1.9 (54.9) | −27.8 (21.6) | −15.9 (34.4) | −44.4 (22.4) | −43.6 (7.7) |

Additional assessments:
 Body weight was only assessed at baseline and end of study
  No significant changes noted
  Not informative about potential for body weight reduction
   ALT and AST: baseline values in normal range (mean=21.3 and 20.1 L/L)
  No significant reductions observed Fasting glucose and insulin: baseline values in normal range (mean=88.2 mg/dL and 7.3 uIU/mL)
  No significant reductions observed
  Likely related to FGF21 mechanism of action as insulin sensitizer
SAD Study Summary
 BIO89-100 is well tolerated at single doses up to 78 mg SC
 Incidence of overall adverse events and treatment-related adverse events did not differ notably among treatment groups across dose range
 Exception: Injection site AEs occurred more in high dose groups (39 mg and 78 mg)
 No trends indicative of clinically important adverse effects of BIO89-100 on laboratory or other safety-related clinical parameters were apparent
 PK profiles are generally dose-proportional with T1/2 ranges ~53 to 100 hours
 BIO89-100-related effects on lipid PD parameters were noted at doses 9.1 mg and higher
 Concentration dependent trends observed with key PD parameters up to 39 mg dose without additional benefit in the 78 mg group
 PD effects consistent across lipid parameters and generally consistent within subjects
 Data supports dosing both once a week and once every two weeks
Conclusions: BIO89-100 at single doses up to 78 mg was safe and well tolerated in healthy subjects, with a favorable PK profile, and was associated with significant improvements in triglycerides, LDL and HDL.

Example 2: Weekly Subcutaneous Administration of BIO89-100, a Novel glycoPEGylated-Fibroblast Growth Factor 21 (FGF-21) Analogue, Inhibits Sweetness Preference in Obese Cynomolgus Monkeys Background: BIO89-100, a novel glycoPEGylated analogue of FGF-21, is being developed for the treatment of nonalcoholic steatohepatitis (NASH). FGF-21 regulates carbohydrate and lipid metabolism; FGF-21 and a long acting analogue were shown to regulate sweetness and alcohol preference in mice, and sweetness preference in monkeys. The objective of this study was to assess the effect of BIO89-100 on sweetness preference in obese cynomolgus monkeys.

Methods: Obese cynomolgus monkeys (mean age—12.6 yrs; weight—10.8 kg) were trained on the 2-bottle test prior to dosing. After acclimation for 2 weeks to 2 bottles of drinking water, monkeys were acclimated for 2 additional weeks to having a bottle of drinking water and a bottle of sweet water (3% sucrose). Baseline data was collected after which BIO89-100 (N=3) at a dose of 1 mg/kg or vehicle (N=3) was administered sc weekly (qW) over 3 weeks, followed by 2 weeks wash-out. The preference for sweet vs. non-sweet water was monitored by measuring daily fluid intake. Clinical assessments and laboratory tests were also performed.

Results: Before introducing sweet water, mean water consumption was 235 mL/day. After introduction of sweet water, mean fluid consumption increased significantly to 650 mL/day, consisting almost exclusively of sweet water. After administration of BIO89-100, preference for sweet water markedly decreased within one day and continued to decrease to a point that a negligible amount of sweet water was consumed (mean 40 mL/day). After end of treatment (wash-out), preference for sweet water gradually re-emerged. Control animals preferred sweet water throughout the study period. In BIO89-100-treated monkeys, decreases in body weight (up to −13%), food intake (up to −60%), triglycerides (up to −78%), and alanine transaminase (up to −44%), and an increase in high-density lipoprotein (up to 39%) compared to baseline were observed. Control animals showed no decrease in body weight, food intake or any other change in blood lipids.

Conclusion: Weekly administration of BIO89-100 to obese monkeys resulted in a significant decrease in sweetness preference and in improvements in metabolic and liver-related lab parameters. These results demonstrate that FGF-21 analogues such as BIO89-100 may be used for treatment modality for NASH. Decreased preference for sugar in humans may, furthermore, confer an additional important benefit in NASH patients.

Example 3—Mechanism of Action Via Potent FGF Receptor Agonism

Figure 15:
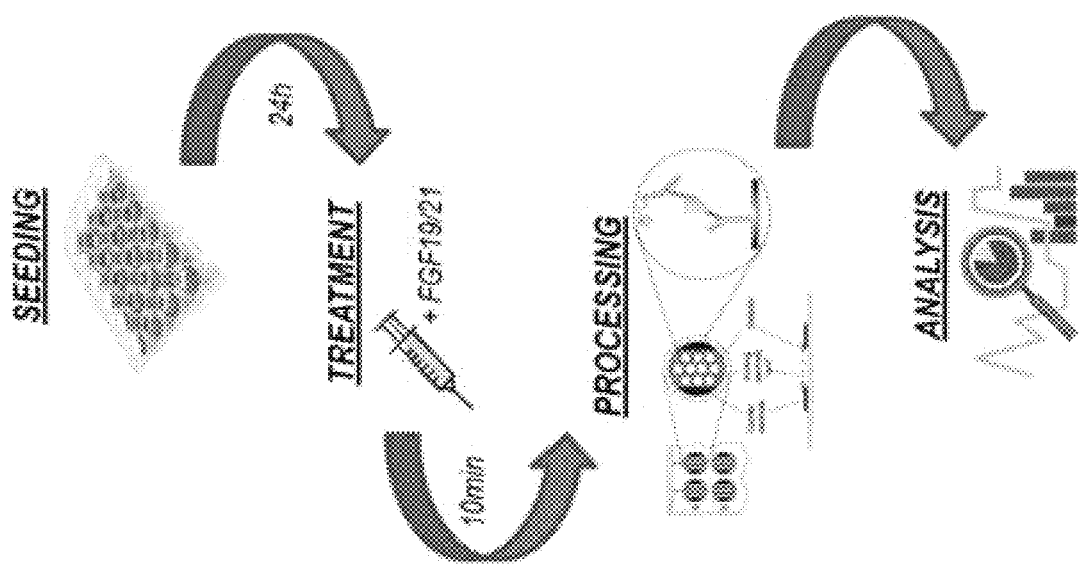
Figures 18A, 18B, 18C, 18D:
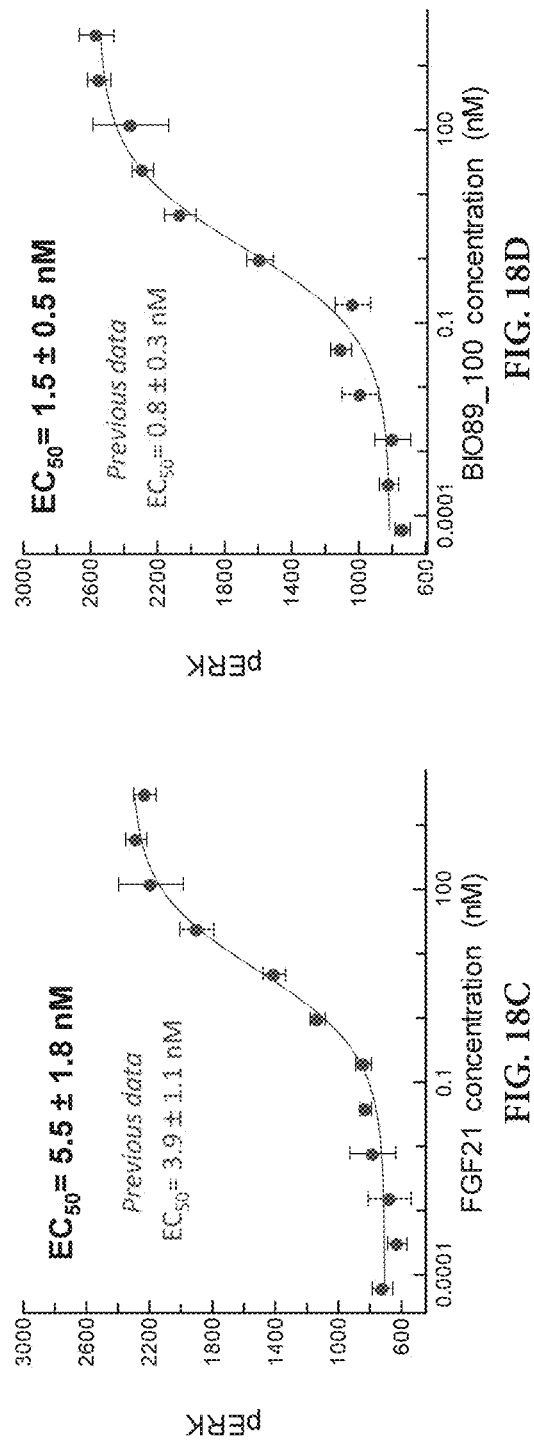
FIGS. 18A and 18C show the results of the pERK functional assay in KLB/FGFR2 expressing cells using FGF-21.
FIGS. 18B and 18D show the results of the pERK functional assay in KLB/FGFR2 expressing cells using BIO89-100 according to some embodiments. Both FGF-21 and and BIO89-100 activate KLB-FGFR2 cells. BIO89-100 showed 3 to 5 fold increase in potency sensitivity over FGF-21 in pERK assay.
Figure 22A:
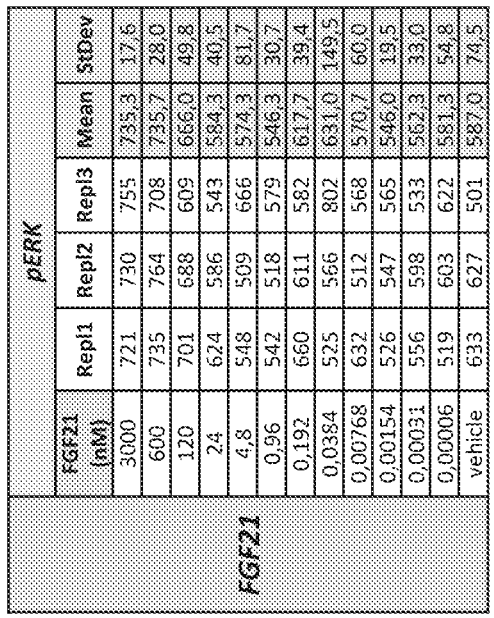
FIGS. 22A and 22C show the results of the pERK functional assay in KLB only expressing cells using FGF-19.
Figure 22B:
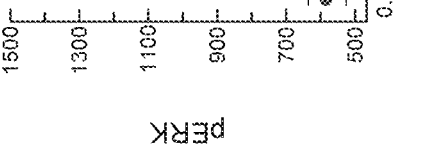
FIGS. 22B and 22D show the results of the pERK functional assay in KLB only expressing cells using FGF-21 according to some embodiments. In KLB expressing cells, FGF-19 and FGF-21 were not active (about 2-fold increase of pERK at 3000 nM).
Figure 22C:
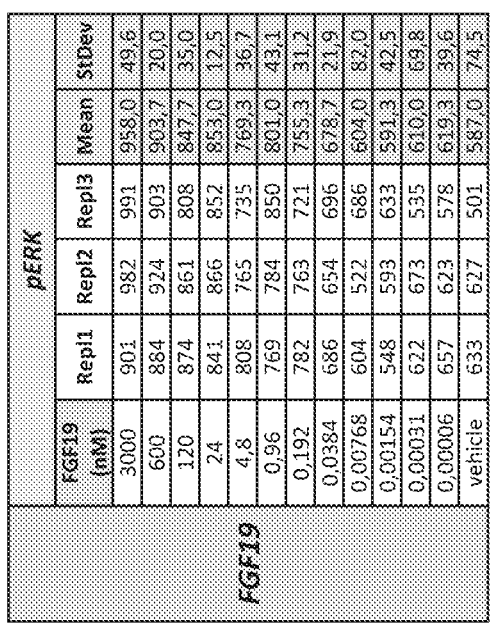
Figure 22D:
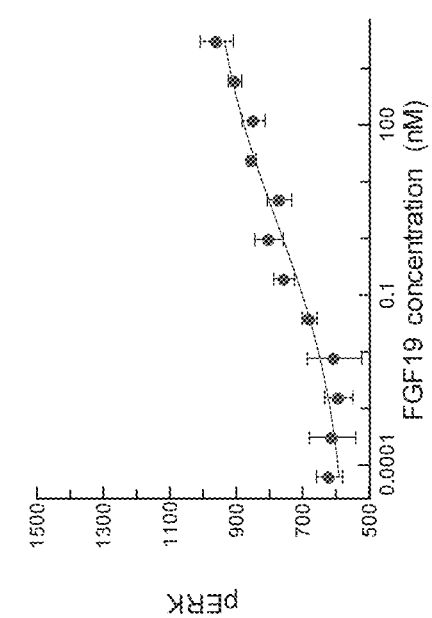
Figures 27A, 27B, 27C, 27D, 27E, 27F:
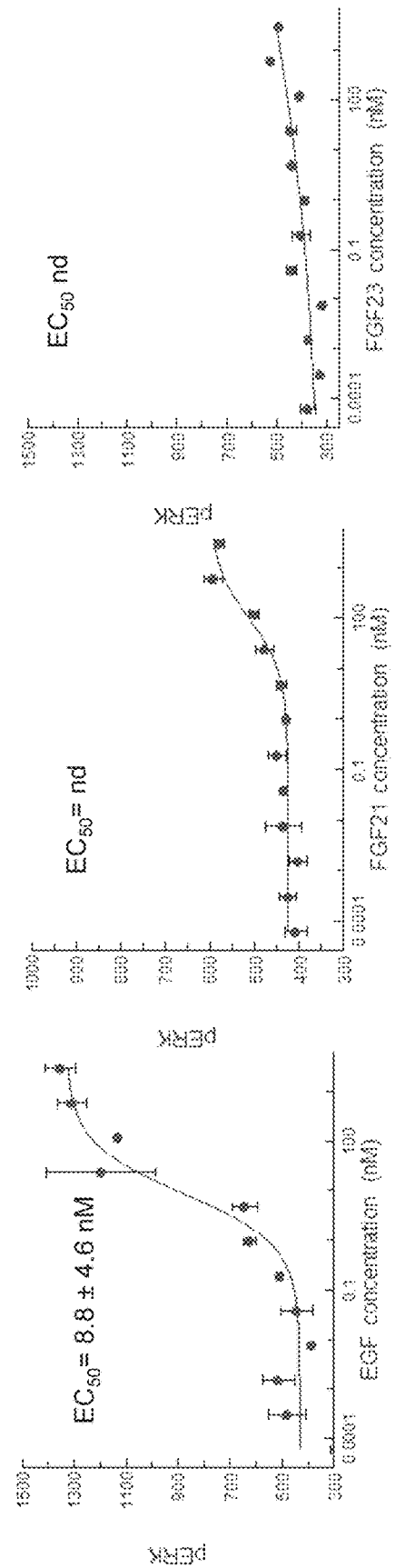
FIGS. 27A and 27D show the results of the pERK functional assay in KLB only expressing cells using EGF.
FIGS. 27B and 27E show the results of the pERK functional assay in KLB only expressing cells using FGF-21.
FIGS. 27C and 27F show the results of the pERK functional assay in KLB only expressing cells using FGF-23.
Figures 28A, 28B, 28C, 28D, 28E, 28F:
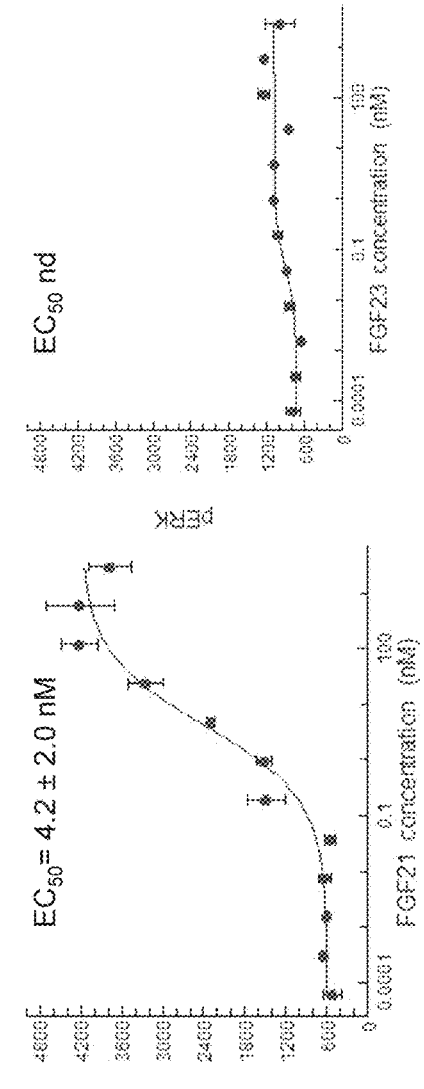
FIGS. 28A and 28D show the results of the pERK functional assay in KLB/FGFR1 expressing cells using EGF.
FIGS. 28B and 28E show the results of the pERK functional assay in KLB/FGFR1 expressing cells using FGF-21.
FIGS. 28C and 28F show the results of the pERK functional assay in in KLB/FGFR1 expressing cells using FGF-23.
Figures 32A, 32B, 32C:
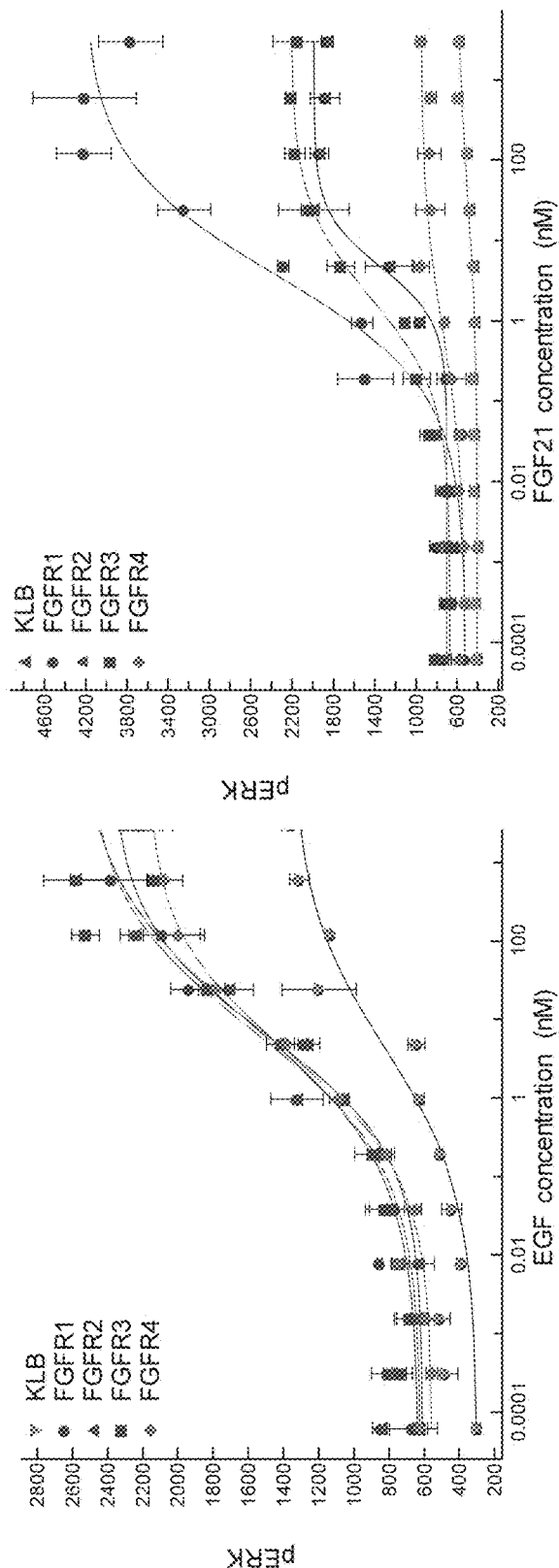
FIGS. 32A-32C provide a summary of the pERK functional assay in KLB only, KLB/FGFR1, KLB/FGFR2, KLB/FGFR3, and KLB/FGFR4 expressing cells.

FIGS. 15-37G present results of the potency of the mutant Fibroblast Growth Factor-21 (FGF-21) peptide conjugate.
PERK Functional Assay:
1. L6 cells expressing KLB/FGFR1 were seeded in a 96-well plate format (104 cells/well) 24 hours before treatment
2. On the day of the assay, cells were starved for 2 hr in serum-free medium, then treated with the ligand (or vehicle alone) at the indicated concentrations and the indicated time points (triplicates)
3. All tubes, plates and pipette tips used for the assay were pre-coated overnight with 1% BSA (in PBS)
4. FGF-21 and BIO89-100 dilutions were made in PBS1× pH7.4 containing 0.1% BSA 5. Following treatment cells were transferred on ice, washed twice in ice-cold PBS and lysed in MSD* lysis buffer, according to Manufacturer's protocol
6. Samples were processed for pERK/ERK levels by Mesoscale Results The data showed that in KLB only and KLB-FGFR4 expressing cells, FGF21 and BIO89-100 were almost non active with only a slight increase of pERK at the highest concentration tested (3,000 nM).

FGF21 and BIO89-100 were highly active in cells expressing FGFR1, FGFR2 and FGFR3.

BIO89-100 was more potent than FGF21 in KLB-FGFR2 and KLB-FGFR1 expressing cells.

BIO89-100 had a comparable potency to FGF21 in KLB-FGFR3 expressing cells.

FGF-19 was highly active in cell expressing FGFR4 but also with FGFR1 and FGFR3.

The negative control, FGF-23, was not active in all cells with no difference between KLB only and the 4 receptors.

The positive control EGF was active with high potency in cells transfected with the 4 receptors Conclusion Preclinical data demonstrates that BIO89-100 has similar activity to native FGF21 at FGF receptors 1c, 2c and 3c, suggesting that BIO89-100 could reproduce the beneficial metabolic benefits of the native hormone, which may translate into clinical benefits for patients with NASH.

Activation of the FGF receptors 1c, 2c and 3c, together with the co-receptor β-klotho, are critical to the signaling of FGF21 and are believed to be responsible for the beneficial metabolic effects observed. In an in vitro study of receptor agonism, BIO89-100 was shown to have activity at very low nanomolar concentrations in cells co-expressing β-klotho and any of FGF receptors 1c, 2c or 3c (FIGS. 15-38). The EC50 (concentration at which one half of the maximal FGF receptor agonist effect is observed) for BIO89-100 was similar across FGF receptors 1c, 2c and 3c and comparable or superior to that of native FGF21 in this functional assay. An EC50 could not be determined for native FGF21 or BIO89-100 at FGF receptor R4.

Example 4

Study BIO89-100-002 is a randomized, double-blind, placebo-controlled, multiple ascending dose (MAD) study to evaluate the safety, tolerability, PK and PD profiles and immunogenicity of BIO89-100 administered SC in approximately 83 subjects with NASH, or with NAFLD who are at a high risk of NASH. This multi-site study consists of 6 cohorts, and evaluates 2 dosing schedules, weekly (QW; Cohorts 1 to 4) and every 2 weeks (Q2W; Cohorts 5 and 6) (Table 1).

There are 2 dose escalation decisions. After Cohort 1 completes the Day 36 visit, subjects can be randomized into Cohorts 2 and 5 (both cohorts to start concurrently). After at least 8 subjects from both Cohort 2 and Cohort 5, including at least 1 subject on placebo in each cohort, complete the Day 36 visit, subjects can be randomized into Cohorts 3, 4 and 6 (all three cohorts to start concurrently).

Cohorts 1 to 4 (weekly regimen): On Day −1, eligible subjects are randomized (as described above) and treated with weekly (QW) SC injection of study intervention starting on Day 1 and continuing through Day 85.

Cohorts 5 and 6 (every 2 weeks regimen): On Day −1, eligible subjects are randomized (as described above) and treated with SC injection of study intervention every 2 weeks (Q2W) starting on Day 1 and continuing through Day 85. Subjects in all cohorts are followed up on Day 92 (1 week post last dose of study intervention) and Day 113, 4 weeks post last dose of study intervention (End of Study visit).

TABLE 2

Dose Escalation Cohorts

| Co-hort | Dose Frequency and Route Level[a] of Administration | Number of Subjects BIO89-100 | Placebo |
|---|---|---|---|
| 1 | 3 mg Weekly (QW), SC to abdomen (1 injection) Days 1, 8, 15, 22, 29, 36, 43, 50, 57, 64, 71, 78 and 85 Total doses (initial 4 weeks +8 week extension): 5 + 8 | 6 | 2 |
| 2 | 9 mg QW, SC to abdomen (1 injection) Days 1, 8, 15, 22, 29, 36, 43, 50, 57, 64, 71, 78 and 85 Total doses (initial 4 weeks + 8 week extension): 5 + 8 | 12 | 3 |
| 3 | 18 mg QW, SC to abdomen (1 injection) Days 1, 8, 15, 22, 29, 36, 43, 50, 57, 64, 71, 78 and 85 Total doses (initial 4 weeks + 8 week extension): 5 + 8 | 14 | 4 |
| 4 | 27 mg QW, SC to abdomen (2 injections) Days 1, 8, 15, 22, 29, 36, 43, 50, 57, 64, 71, 78 and 85 Total doses (initial 4 weeks + 8 week extension): 5 + 8 | 9 | 3 |
| 5 | 18 mg Every 2 weeks (Q2W), SC to abdomen (1 injection) Days 1, 15, 29, 43, 57, 71 and 85. Total doses (initial 4 weeks + 8 week extension): 3 + 4 | 14 | 4 |
| 6 | 36 mg Q2W, SC to abdomen (2 injections) Days 1, 15, 29, 43, 57, 71 and 85. Total doses (initial 4 weeks + 8 week extension): 3 + 4 | 9 | 3 |

[a]The actual doses will be ±5% the mg dose due to technical considerations related to drug withdrawal from the vials into the syringes for injection. This difference is considered negligible for subject exposure.

Change and percentage change from baseline in the following biomarkers/PD parameters:

Anthropomorphic Measurements:
Body weight
Waist circumference
Waist/hip ratio
Laboratory Parameters Triglycerides
Non-high density lipoprotein (Non-HDL) cholesterol
High density lipoprotein (HDL-c)
Low density lipoprotein (LDL-c)
Hemoglobin A1c (HbA1c)
Homeostatic Model Assessment for Insulin Resistance (HOMA-IR)
Liver function tests: alanine transaminase (ALT), aspartate transaminase (AST)
Adiponectin
N-Terminal Propeptide of Type III Collagen (Pro-C3)
Free fatty acids and Adipo-IR (fasting free fatty acids x fasting insulin) inflammation marker high-sensitivity C-reactive protein (hs-CRP)
Total cholesterol
OGTT including C-peptide, glucose, and insulin
IGF-1, total
CK-18
Enhanced LiverFibrosis (ELF) panel
Imaging Measures Magnetic Resonance Imaging—Whole liver Proton Density Fat Fraction (MRI-PDFF)
Liver volume
Abdominal visceral fat
Abdominal subcutaneous fat
Fibroscan CAP score
Fibroscan VCTE score Enhanced LiverFibrosis (ELF) Panel:

The enhanced liver fibrosis (ELF) blood test has recently been recommended by the National Institute for Health and Care Excellence to test for advanced fibrosis in NAFLD. The ELF test involves calculating a score from the concentrations of serum biomarkers: tissue inhibitor of matrix metalloproteinases-1 (TIMP-1), amino-terminal propeptide of procollagen type III (P3NP), and hyaluronic acid (HA).

N-Terminal Propeptide of Type III Collagen (Pro-C3)

N-protease cleaved N-terminal propeptide of type 3 procollagen (P3NP) neo-epitope (Pro-C3) is derived from the synthesis of type 3 collagen. Pro-C3 appears to correlate with liver fibrosis stage, fibrosis regression and response to treatment both as a single test and as part of algorithms Magnetic Resonance Imaging—Whole Liver Proton Density Fat Fraction (MRI-PDFF)

MRI-PDFF is as a noninvasive, quantitative, and accurate measure of liver fat content (imaging-based biomarker) to assess treatment response in NASH clinical studies. This technology enables post-processing of MRI data into parametric map of PDFF (Antaros Medical, Sweden) to provide accurate and quantitative measures of liver fat.

Liver Volume

A dedicated Axial 3 dimensions (3D) T1-weighted scan with or without fat suppression is positioned to cover the entire liver. Analysis is done using a semiautomated software to delineate the outer borders of the liver and the liver volume will be calculated in liters.

Visceral Abdominal Fat (VAT)/Subcutaneous Abdominal Fat (SAT)

A 2 or 3 point gradient echo Dixon imaging is performed in the axial plane centered at the L4-L5 interface covering approximately ±10 cm in the feet-head direction. Water and fat images are reconstructed and the visceral and subcutaneous adipose tissue volumes in the abdominal region are quantified using a semi-automated software giving adipose tissue volume as output in liters.

PDFF

The PDFF is determined using a 6 echo gradient echo pulse sequence covering the liver in the axial plane. Analysis is performed by semi-automatic contouring of the liver in every slice avoiding major vessels and bile ducts. The method applies multi-peak lipid spectral models and simultaneous quantification and correction for T2*. The liver fat value (PDFF) is the mean value of all voxels in the identified volume of interest.

The embodiments of the invention described above are intended to be exemplary only. Those skilled in this art will understand that various modifications of detail may be made to these embodiments, all of which come within the scope of the invention. All publications mentioned herein are hereby incorporated by reference in their entireties. While the foregoing invention has been described in some detail for purposes of clarity and understanding, it will be appreciated by one skilled in the art from a reading of the disclosure that various changes in form and detail can be made without departing from the true scope of the invention in the appended claims.

Specific examples of methods and kits have been described herein for purposes of illustration. These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

The invention claimed is:

1. A method of treating nonalcoholic steatohepatitis (NASH) in a subject in need thereof, comprising:
   administering once a week to the subject in need thereof a pharmaceutical composition comprising from about 3 mg to about 27 mg of a mutant Fibroblast Growth Factor-21 (FGF-21) peptide conjugate and a pharmaceutically acceptable carrier,
   wherein the mutant FGF-21 peptide conjugate comprises
   i) a mutant FGF-21 peptide comprising the amino acid sequence of SEQ ID NO: 2,
   ii) a glycosyl moiety, and
   iii) a 20 kDa polyethylene glycol (PEG), wherein the mutant FGF-21 peptide is attached to the glycosyl moiety by a covalent bond between a threonine at amino acid position 173 of SEQ ID NO: 2 and a first site of the glycosyl moiety and wherein the glycosyl moiety is attached to the 20 kDa PEG by a covalent bond between a second site of the glycosyl moiety and the 20 kDa PEG,
   wherein administration of the pharmaceutical composition results in at least one of:
   a reduction of the liver size as assessed by Magnetic resonance imaging—Proton density fat fraction,
   a reduction of the levels of one or more biomarkers comprising Pro-C3, alanine transaminase (ALT), Enhanced LiverFibrosis (ELF) panel, Adiponectin, CK-18, inflammation marker high-sensitivity C-reactive protein (hs-CRP), Hemoglobin A1c (HbA1c), and Triglycerides, and an increase of the levels of HDL-c.

2. The method of claim 1, wherein the subject is a human subject.

3. The method of claim 1, wherein the pharmaceutical composition is administered sub-subcutaneously.

4. The method of claim 1, wherein the glycosyl moiety comprises at least one of an N-acetylgalactosamine (GalNAc) residue, a galactose (Gal) residue, a sialic acid (Sia) residue, a 5-amine analogue of a Sia residue, a mannose (Man) residue, mannosamine, a glucose (Glc) residue, an N-acetylglucosamine (GlcNAc) residue, a fucose residue, a xylose residue, or a combination thereof.

5. The method of claim 1, wherein the glycosyl moiety comprises at least one N-acetylgalactosamine (GalNAc) residue, at least one galactose (Gal) residue, at least one sialic acid (Sia) residue, or a combination thereof.

6. The method of claim 5, wherein the at least one Sia residue is a nine-carbon carboxylated sugar.

7. The method of claim 6, wherein the at least one Sia residue is N-acetyl-neuraminic acid (2-keto-5-acetamido-3,5-dideoxy-D-glycero-D-galactononulopyranos-1-onic acid (Neu5Ac), N-glycolylneuraminic acid (Neu5Gc), 2-keto-3-deoxy-nonulosonic acid (KDN), or a 9-substituted sialic acid.

8. The method of claim 7, wherein the 9-substituted sialic acid is 9-O-lactyl-Neu5Ac, 9-O-acetyl-Neu5Ac, 9-deoxy-9-fluoro-Neu5Ac, or 9-azido-9-deoxy-Neu5Ac.

9. The method of claim 1, wherein the glycosyl moiety comprises the structure -GalNAc-Sia-.

10. The method of claim 1, wherein the 20 kDa PEG moiety is attached to the glycosyl moiety by a covalent bond to a linker, wherein the linker comprises at least one amino acid residue.

11. The method of claim 10, wherein the at least one amino acid residue is a glycine (Gly).

12. The method of claim 1, wherein the mutant FGF-21 peptide conjugate comprises the structure -GalNAc-Sia-Gly-PEG (20 kDa).

13. The method of claim 1, wherein the mutant FGF-21 peptide conjugate comprises the structure:

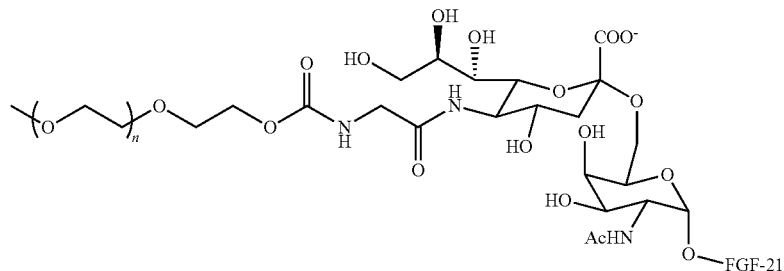

wherein n is an integer selected from 450 to 460.

14. The method of claim 1, wherein the 20 kDa PEG is a linear or branched PEG.

15. The method of claim 1, wherein the 20 kDa PEG is a 20 kDa methoxy-PEG.

16. The method of claim 1, wherein the mutant mutant FGF-21 peptide conjugate displays an equal or higher potency than wild type FGF-21 when tested in vitro in KLB-FGFR1, KLB-FGFR2 and KLB-FGFR3 expressing cells.

17. A method of treating nonalcoholic steatohepatitis (NASH) in a subject in need thereof, comprising:
administering once every two weeks to the subject in need thereof a pharmaceutical composition comprising from about 18 mg to about 36 mg of a mutant Fibroblast Growth Factor-21 (FGF-21) peptide conjugate and a pharmaceutically acceptable carrier,
wherein the mutant FGF-21 peptide conjugate comprises
i) a mutant FGF-21 peptide comprising the amino acid sequence of SEQ ID NO: 2,
ii) a glycosyl moiety, and
iii) a 20 kDa polyethylene glycol (PEG), wherein the mutant FGF-21 peptide is attached to the glycosyl moiety by a covalent bond between a threonine at amino acid position 173 of SEQ ID NO: 2 and a first site of the glycosyl moiety and wherein the glycosyl moiety is attached to the 20 kDa PEG by a covalent bond between a second site of the glycosyl moiety and the 20 kDa PEG,
wherein administration of the pharmaceutical composition results in at least one of:
a reduction of the liver size as assessed by Magnetic resonance imaging—Proton density fat fraction,
a reduction of the levels of one or more biomarkers comprising Pro-C3, alanine transaminase (ALT), Enhanced Liver Fibrosis (ELF) panel, Adiponectin, CK-18, inflammation marker high-sensitivity C-reactive protein (hs-CRP), Hemoglobin A1c (HbA1c), Triglycerides, LDL-c, and
an increase of the levels of HDL-c.

18. The method of claim 17, wherein the subject is a human subject.

19. The method of claim 17, wherein the pharmaceutical composition is administered sub-subcutaneously.

20. The method of claim 17, wherein the glycosyl moiety comprises at least one of an N-acetylgalactosamine (GalNAc) residue, a galactose (Gal) residue, a sialic acid (Sia) residue, a 5-amine analogue of a Sia residue, a mannose (Man) residue, mannosamine, a glucose (Glc) residue, an N-acetylglucosamine (GlcNAc) residue, a fucose residue, a xylose residue, or a combination thereof.

21. The method of claim 17, wherein the glycosyl moiety comprises at least one N-acetylgalactosamine (GalNAc) residue, at least one galactose (Gal) residue, at least one sialic acid (Sia) residue, or a combination thereof.

22. The method of claim 21, wherein the at least one Sia residue is a nine-carbon carboxylated sugar.

23. The method of claim 22 wherein the at least one Sia residue is N-acetyl-neuraminic acid (2-keto-5-acetamido-3,5-dideoxy-D-glycero-D-galactononulopyranos-1-onic acid (Neu5Ac), N-glycolylneuraminic acid (Neu5Gc), 2-keto-3-deoxy-nonulosonic acid (KDN), or a 9-substituted sialic acid.

24. The method of claim 23, wherein the 9-substituted sialic acid is 9-O-lactyl-Neu5Ac, 9-O-acetyl-Neu5Ac, 9-deoxy-9-fluoro-Neu5Ac, or 9-azido-9-deoxy-Neu5Ac.

25. The method of claim 17, wherein the glycosyl moiety comprises the structure -GalNAc-Sia-.

26. The method of claim 17, wherein the 20 kDa PEG moiety is attached to the glycosyl moiety by a covalent bond to a linker, wherein the linker comprises at least one amino acid residue.

27. The method of claim 26, wherein the at least one amino acid residue is a glycine (Gly).

28. The method of claim 17, wherein the mutant FGF-21 peptide conjugate comprises the structure -GalNAc-Sia-Gly-PEG (20 kDa).

29. The method of claim 17, wherein the mutant FGF-21 peptide conjugate comprises the structure:

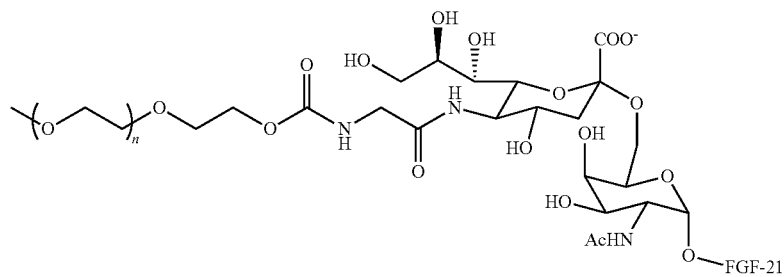

wherein n is an integer selected from 450 to 460.

30. The method of claim 17, wherein the 20 kDa PEG is a linear or branched PEG.

31. The method of claim 17, wherein the 20 kDa PEG is a 20 kDa methoxy-PEG.

32. The method of claim 17, wherein the mutant FGF-21 peptide conjugate displays an equal or higher potency than wild type FGF-21 when tested in vitro in KLB-FGFR1, KLB-FGFR2 and KLB-FGFR3 expressing cells.

* * * * *